(12) United States Patent
Khalili et al.

(10) Patent No.: US 12,251,429 B2
(45) Date of Patent: *Mar. 18, 2025

(54) METHODS AND COMPOSITIONS FOR RNA-GUIDED TREATMENT OF HIV INFECTION

(71) Applicant: Temple University—of the Commonwealth System of Higher Education, Philadelphia, PA (US)

(72) Inventors: Kamel Khalili, Bala Cynwyd, PA (US); Wenhui Hu, Cherry Hill, NJ (US); Yonggang Zhang, Maple Shade, NJ (US)

(73) Assignee: Temple University—of the Commonwealth System of Higher Education, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/017,037

(22) Filed: Sep. 10, 2020

(65) Prior Publication Data

US 2021/0052709 A1 Feb. 25, 2021

Related U.S. Application Data

(63) Continuation of application No. 15/578,372, filed as application No. PCT/US2016/035141 on Jun. 1, 2016, now Pat. No. 11,298,410.

(60) Provisional application No. 62/308,320, filed on Mar. 15, 2016, provisional application No. 62/169,633, filed on Jun. 2, 2015, provisional application No. 62/169,384, filed on Jun. 1, 2015.

(51) Int. Cl.
| | | |
|---|---|---|
| *A61K 38/46* | (2006.01) | |
| *A61K 48/00* | (2006.01) | |
| *A61P 31/18* | (2006.01) | |
| *C12N 9/22* | (2006.01) | |
| *C12N 15/11* | (2006.01) | |
| *C12N 15/113* | (2010.01) | |
| *C12N 15/90* | (2006.01) | |

(52) U.S. Cl.
CPC ............ *A61K 38/465* (2013.01); *A61K 48/00* (2013.01); *A61P 31/18* (2018.01); *C12N 9/22* (2013.01); *C12N 15/11* (2013.01); *C12N 15/1132* (2013.01); *C12N 15/907* (2013.01); *C12N 2310/10* (2013.01); *C12N 2310/20* (2017.05); *C12N 2320/11* (2013.01)

(58) Field of Classification Search
None
See application file for complete search history.

(56) References Cited

U.S. PATENT DOCUMENTS

| | | |
|---|---|---|
| 5,034,506 A | 7/1991 | Summerton et al. |
| 8,697,359 B1 | 4/2014 | Zhang |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 9,023,649 B2 | 5/2015 | Mali et al. |
| 9,068,179 B1 | 6/2015 | Liu et al. |
| 9,074,199 B1 | 7/2015 | Chavez et al. |
| 9,163,284 B2 | 10/2015 | Liu et al. |
| 9,228,207 B2 | 1/2016 | Liu et al. |
| 9,260,723 B2 | 2/2016 | Mali et al. |
| 9,267,135 B2 | 2/2016 | Church et al. |
| 9,322,037 B2 | 4/2016 | Liu et al. |
| 9,340,799 B2 | 5/2016 | Liu et al. |
| 9,340,800 B2 | 5/2016 | Liu et al. |
| 9,388,430 B2 | 7/2016 | Liu et al. |
| 9,526,784 B2 | 12/2016 | Liu et al. |
| 9,587,252 B2 | 3/2017 | Church et al. |
| 9,737,604 B2 | 8/2017 | Liu et al. |
| 9,822,372 B2 | 11/2017 | Zhang et al. |
| 9,840,699 B2 | 12/2017 | Liu et al. |
| 9,840,713 B2 | 12/2017 | Zhang |
| 9,925,248 B2 | 3/2018 | Khalili et al. |
| 9,925,425 B2 | 3/2018 | Ladd et al. |

(Continued)

FOREIGN PATENT DOCUMENTS

| | | |
|---|---|---|
| CN | 103923911 A | 7/2014 |
| CN | 104480144 A | 4/2015 |

(Continued)

OTHER PUBLICATIONS

Scott, "The zinc finger nuclese monopoly" 23(8) Nature Biotechnology 915-918 (Year: 2005).*

(Continued)

*Primary Examiner* — Nancy J Leith

(74) *Attorney, Agent, or Firm* — Nicholas Zachariades; Fox Rothschild LLP

(57) ABSTRACT

Compositions for specifically cleaving target sequences in retroviruses include nucleic acids encoding a Clustered Regularly Interspace Short Palindromic Repeat (CRISPR) associated endonuclease and a guide RNA sequence complementary to one or more target nucleic acid sequences in a retrovirus genome.

1 Claim, 25 Drawing Sheets

Specification includes a Sequence Listing.

(56) References Cited

U.S. PATENT DOCUMENTS

| | | | |
|---|---|---|---|
| 9,970,024 B2 | 5/2018 | Church et al. |
| 9,981,020 B2 | 5/2018 | Khalili et al. |
| 9,999,671 B2 | 6/2018 | Liu et al. |
| 10,077,453 B2 | 9/2018 | Liu et al. |
| 10,100,291 B2 | 10/2018 | Chavez et al. |
| 10,273,501 B2 | 4/2019 | Church et al. |
| 10,329,587 B2 | 6/2019 | Church et al. |
| 10,435,679 B2 | 10/2019 | Chavez et al. |
| 10,435,708 B2 | 10/2019 | Mali et al. |
| 10,465,176 B2 | 11/2019 | Liu et al. |
| 10,508,298 B2 | 12/2019 | Liu et al. |
| 10,563,225 B2 | 2/2020 | Church et al. |
| 10,570,415 B2 | 2/2020 | Doudna et al. |
| 10,577,630 B2 | 3/2020 | Zhang et al. |
| 10,597,679 B2 | 3/2020 | Liu et al. |
| 10,640,789 B2 | 5/2020 | Church et al. |
| 10,682,410 B2 | 6/2020 | Liu et al. |
| 10,683,490 B2 | 6/2020 | Chavez et al. |
| 10,704,062 B2 | 7/2020 | Liu et al. |
| 10,711,285 B2 | 7/2020 | Zhang et al. |
| 10,717,990 B2 | 7/2020 | Mali et al. |
| 10,737,984 B2 | 8/2020 | Schaedler et al. |
| 10,767,194 B2 | 9/2020 | Church et al. |
| 10,781,444 B2 | 9/2020 | Zhang et al. |
| 10,787,684 B2 | 9/2020 | Byrne et al. |
| 10,858,639 B2 | 12/2020 | Liu et al. |
| 10,912,833 B2 | 2/2021 | Liu et al. |
| 10,930,367 B2 | 2/2021 | Zhang et al. |
| 10,946,108 B2 | 3/2021 | Zhang et al. |
| 10,954,548 B2 | 3/2021 | Liu et al. |
| 11,008,588 B2 | 5/2021 | Zhang et al. |
| 11,041,173 B2 | 6/2021 | Zhang et al. |
| 11,053,481 B2 | 7/2021 | Liu et al. |
| 11,060,115 B2 | 7/2021 | Severinov et al. |
| 11,124,782 B2 | 9/2021 | Liu et al. |
| 11,236,359 B2 | 2/2022 | Mali et al. |
| 11,273,209 B2 * | 3/2022 | Khalili | C12N 9/22 |
| 11,286,470 B2 | 3/2022 | Chavez et al. |
| 11,291,710 B2 * | 4/2022 | Khalili | A61P 31/18 |
| 11,299,755 B2 | 4/2022 | Liu et al. |
| 11,306,328 B2 | 4/2022 | Church et al. |
| 11,332,719 B2 | 5/2022 | Zhang et al. |
| 11,359,211 B2 | 6/2022 | Church et al. |
| 11,365,429 B2 | 6/2022 | Church et al. |
| 11,459,585 B2 | 10/2022 | Church et al. |
| 11,491,207 B2 * | 11/2022 | Khalili | C12N 15/00 |
| 11,512,325 B2 | 11/2022 | Church et al. |
| 11,535,863 B2 | 12/2022 | Church et al. |
| 11,578,343 B2 | 2/2023 | Liu et al. |
| 11,597,949 B2 | 3/2023 | Zhang et al. |
| 11,649,469 B2 | 5/2023 | Church et al. |
| 11,920,181 B2 | 3/2024 | Liu et al. |
| 11,981,917 B2 | 5/2024 | Church et al. |
| 12,018,272 B2 | 6/2024 | Church et al. |
| 12,018,275 B2 | 6/2024 | Zhang et al. |
| 2014/0342456 A1 | 11/2014 | Mali et al. |
| 2014/0356956 A1 | 12/2014 | Church et al. |
| 2015/0232833 A1 | 8/2015 | Mali et al. |
| 2015/0232882 A1 | 8/2015 | Zhang et al. |
| 2015/0247150 A1 | 9/2015 | Zhang et al. |
| 2015/0291965 A1 | 10/2015 | Zhang et al. |
| 2016/0040165 A1 | 2/2016 | Howell et al. |
| 2016/0153004 A1 | 6/2016 | Zhang et al. |
| 2016/0281072 A1 | 9/2016 | Zhang |
| 2016/0340662 A1 | 11/2016 | Zhang et al. |
| 2017/0044569 A9 | 2/2017 | Church et al. |
| 2017/0152528 A1 | 6/2017 | Zhang |
| 2017/0198269 A1 | 7/2017 | Zhang et al. |
| 2018/0000970 A1 | 1/2018 | Roehm et al. |
| 2018/0148379 A1 | 5/2018 | Schaedler et al. |
| 2018/0169193 A1 | 6/2018 | Khalili et al. |
| 2018/0169194 A1 | 6/2018 | Khalili et al. |
| 2018/0169195 A1 | 6/2018 | Khalili et al. |
| 2018/0200343 A1 | 7/2018 | Khalili et al. |
| 2018/0207243 A1 | 7/2018 | Khalili et al. |
| 2018/0208914 A1 | 7/2018 | Malcolm et al. |
| 2018/0214521 A1 | 8/2018 | Khalili et al. |
| 2018/0221458 A1 | 8/2018 | Khalili et al. |
| 2018/0228874 A1 | 8/2018 | Khalili et al. |
| 2018/0228875 A1 | 8/2018 | Khalili et al. |
| 2018/0228876 A1 | 8/2018 | Khalili et al. |
| 2018/0236041 A1 | 8/2018 | Khalili et al. |
| 2018/0236042 A1 | 8/2018 | Khalili et al. |
| 2018/0236043 A1 | 8/2018 | Khalili et al. |
| 2018/0236044 A1 | 8/2018 | Khalili et al. |
| 2018/0236045 A1 | 8/2018 | Khalili et al. |
| 2018/0236046 A1 | 8/2018 | Khalili et al. |
| 2018/0236103 A1 | 8/2018 | Friedland et al. |
| 2018/0296649 A1 | 10/2018 | Khalili et al. |
| 2018/0303915 A1 | 10/2018 | Khalili et al. |
| 2018/0327756 A1 | 11/2018 | Zhang et al. |
| 2018/0355375 A1 | 12/2018 | Zhang et al. |
| 2019/0017058 A1 | 1/2019 | Zhang et al. |
| 2019/0032057 A1 | 1/2019 | Khalili et al. |
| 2019/0083656 A1 | 3/2019 | Khalili et al. |
| 2019/0085326 A1 | 3/2019 | Khalili et al. |
| 2019/0093091 A1 | 3/2019 | Khalili et al. |
| 2019/0093092 A1 | 3/2019 | Khalili et al. |
| 2019/0153476 A1 | 5/2019 | Zhang |
| 2019/0225963 A1 | 7/2019 | Khalili et al. |
| 2019/0247470 A1 | 8/2019 | Khalili et al. |
| 2019/0256844 A1 | 8/2019 | Khalili et al. |
| 2019/0365862 A1 | 12/2019 | Khalili et al. |
| 2019/0367910 A1 | 12/2019 | Khalili et al. |
| 2019/0367924 A1 | 12/2019 | Khalili et al. |
| 2019/0390204 A1 | 12/2019 | Zhang et al. |
| 2020/0032278 A1 | 1/2020 | Zhang et al. |
| 2020/0063147 A1 | 2/2020 | Zhang et al. |
| 2020/0080094 A1 | 3/2020 | Zhang et al. |
| 2020/0140865 A1 | 5/2020 | Khalili et al. |
| 2020/0165601 A1 | 5/2020 | Zhang et al. |
| 2020/0282025 A1 | 9/2020 | Khalili |
| 2020/0299732 A1 | 9/2020 | Church et al. |
| 2020/0308599 A1 | 10/2020 | Church et al. |
| 2020/0318123 A1 | 10/2020 | Zhang |
| 2020/0323984 A1 | 10/2020 | Liu et al. |
| 2020/0354742 A1 | 11/2020 | Zhang et al. |
| 2020/0392487 A1 | 12/2020 | Khalili et al. |
| 2021/0052709 A1 | 2/2021 | Khalili et al. |
| 2021/0079407 A1 | 3/2021 | Zhang |
| 2021/0108196 A1 | 4/2021 | Zhang et al. |
| 2021/0147879 A1 | 5/2021 | Byrne et al. |
| 2021/0214698 A1 | 7/2021 | Liu et al. |
| 2021/0222193 A1 | 7/2021 | Church et al. |
| 2021/0269831 A1 | 9/2021 | Zhang et al. |
| 2021/0292794 A1 | 9/2021 | Zhang et al. |
| 2021/0315994 A1 | 10/2021 | Liu et al. |
| 2021/0361779 A1 | 11/2021 | Zhang et al. |
| 2021/0366572 A1 | 11/2021 | Zhang et al. |
| 2022/0119785 A1 | 4/2022 | Liu et al. |
| 2022/0135985 A1 | 5/2022 | Zhang et al. |
| 2022/0235382 A1 | 7/2022 | Church et al. |
| 2022/0380811 A1 | 12/2022 | Church et al. |
| 2023/0056852 A1 | 2/2023 | Liu et al. |
| 2023/0058176 A1 | 2/2023 | Liu et al. |
| 2023/0257781 A1 | 8/2023 | Church et al. |
| 2023/0279443 A1 | 9/2023 | Liu et al. |
| 2023/0340505 A1 | 10/2023 | Zhang |
| 2023/0374527 A1 | 11/2023 | Zhang |
| 2023/0374550 A1 | 11/2023 | Zhang et al. |
| 2023/0399662 A1 | 12/2023 | Zhang |
| 2024/0035048 A1 | 2/2024 | Zhang |
| 2024/0117365 A1 | 4/2024 | Zhang |
| 2024/0175057 A1 | 5/2024 | Church et al. |
| 2024/0182913 A1 | 6/2024 | Zhang |
| 2024/0209359 A1 | 6/2024 | Zhang et al. |

FOREIGN PATENT DOCUMENTS

| | | |
|---|---|---|
| CN | 104726449 | 6/2015 |
| WO | 2014165349 A1 | 10/2014 |

(56) References Cited

FOREIGN PATENT DOCUMENTS

| WO | 2015031775 A1 | 3/2015 |
|---|---|---|
| WO | 2016196539 A2 | 12/2016 |

OTHER PUBLICATIONS

Mussolino et al., "Tale nucleases: tailored genome engineering made easy" 23 Current Opinion in Biotechnology 644-650 (Year: 2012).*
Qu et al., "Zinc finger nuclease: a new approach for excising HIV-1 proviral DNA from infected human T cells" 41 Molecular Biology Reports 5819-5827 (Year: 2014).*
Gaj et al., "ZFN, TALEN, and CRISPR/Cas-based method for genome editing" 31(7) Trends in Biotechnology 397-405 (Year: 2013).*
Bassett et al. (Jan. 2014) "CRISPR/Cas9 and Genome Editing in *Drosophila*", Journal of Genetics and Genomics, 41(1):7-19.
Brinkman et al. (Dec. 2014) "Easy Quantitative Assessment of Genome Editing by Sequence Trace Decomposition", Nucleic Acids Research, e168, 42(22):08 pages.
Carrington et al. (Dec. 2015) "CRISPR-STAT: an easy and reliable PCR-based method to evaluate target-specific sgRNA activity", Nucleic Acids Research, e157, 43(22):08 pages.
Christensen et al. (1998) "A Novel Class of Oligonucleotide Analogues Containing 2'-O,3'-C-Linked [3.2.0] Bicycloarabinonucleoside Monomers: Synthesis, Thermal Affinity Studies, and Molecular Modeling", Journal of the American Chemical Society, 120(22):5458-5463.
Dahlem et al. (Aug. 16, 2012) "Simple Methods for Generating and Detecting Locus-Specific Mutations Induced with TALENs in the Zebrafish Genome", PLoS One, 8(8):15 pages.
Dampier et al. (Oct. 2014) "HIV Excision Utilizing CRISPR/Cas9 Technology: Attacking the Proviral Quasispecies in Reservoirs to Achieve a Cure", MOJ Immunology, 1(4):10 pages.
De Mesmaeker et al. (Sep. 1995) "Antisense Oligonucleotides", Accounts of Chemical Research, 28 (9):366-374.
Doench et al. (Dec. 2014) "Rational Design of Highly Active sgRNAs for CRISPR-Cas9-Mediated Gene Inactivation", Nature Biotechnology, 32(12):17 pages.
Ebina et al. (Aug. 26, 2013) "Harnessing the CRISPR/Cas9 System to Disrupt Latent HIV-1 Provirus", Scientific Reports, 3(2510):1-7.
Felgner et al. (1989) "Cationic Liposome-Mediated Transfection", Bethesda Research Laboratories Focus, 11 (2):21-25.
Freier et al. (1997) "The Ups and Downs of Nucleic Acid Duplex Stability: Structure-Stability Studies on Chemically-Modified DNA:RNA Duplexes", Nucleic Acids Research, 25(22):4429-4443.
Frock et al. (Feb. 2015) "Genome-Wide Detection of DNA Double-Stranded Breaks Induced by Engineered Nucleases", Nature Biotechnology, 33(2):11 pages.
Gagnon et al.(Aug. 2014) "Efficient Mutagenesis by Cas9 ProteinMediated Oligonucleotide Insertion and Large-Scale Assessment of Single-Guide RNAs", PLoS ONE, 9(5):8 pages.
Gebeyehu et al. (Jun. 11, 1987) "Novel Biotinylated Nucleotide-Analogs for Labeling and Colorimetric Detection of DNA", Nucleic Acids Research, 15(11):4513-4534.
Güell et al. (Oct. 15, 2014) "Genome Editing Assessment Using CRISPR Genome Analyzer (CRISPR-GA)", Bioinformatics, 30(20):2968-2970.
Herdewin Piet, (Jul. 8, 2000) "Heterocyclic Modifications of Oligonucleotides and Antisense Technology", Antisense and Nucleic Acid Drug Development, 10(4):297-310.
Hu et al. (Jan. 1, 2015) "Generation of a Stable Packaging Cell Line Producing High-Titer PPT-Deleted Integration-Deficient Lentiviral Vectors", Molecular Therapy—Methods & Clinical Development, 2(15025):10 pages.
Jadlowsky et al. (Jun. 2014) "Negative Elongation Factor Is Required for the Maintenance of Proviral Latency but Does Not Induce Promoter-Proximal Pausing of RNA Polymerase II on the HIV Long Terminal Repeat", Molecular and Cellular Biology, 34(11):1911-1928.
Kabanov et al. (Jan. 1, 1990) "A New Class of Antivirals: Antisense Oligonucleotides Combined with a Hydrophobic Substituent Effectively Inhibit Influenza Virus Reproduction and Synthesis of Virus-Specific Proteins in MDCK Cells", FEBS Letters, 259(2):327-330.
Kaminski et al. (Aug. 2016) "Excision of HIV-1 DNA by Gene Editing: A Proof-of-Concept in Vivo Study", Gene Therapy, 23(8-9):13 pages.
Khalili et al. (Jun. 2015) "Genome Editing Strategies: Potential Tools for Eradicating HIV-1/AIDS", Journal of NeuroVirology, 21(3):310-321.
Kim et al. (2014) "Genotyping with CRISPR-Cas-derived RNA-guided endonucleases", Nature Communications, 5 (3157):08 pages.
Kopp et al. (Mar. 1992) "Progressive Glomerulosclerosis and Enhanced Renal Accumulation of Basement Membrane Components in Mice Transgenic for Human Immunodeficiency Virus Type 1 Genes", PNAS, 89 (5):1577-1581.
Kornberg et al. (1980) "DNA Replication", San Francisco: W. H. Freeman and Co., 75-77.
Letsinger et al. (1989) "Cholesteryl-Conjugated Oligonucleotides: Synthesis, Properties, and Activity as Inhibitors of Replication of Human Immunodeficiency Virus in Cell Culture", Proceedings of the National Academy of Sciences, Sep. 1, 1986(17):6553-6556.
Liao et al. (Mar. 10, 2015) "Use of the CRISPR/Cas9 System as an Intracellular Defense against HIV-1 Infection in Human Cells", Nature Communications, 6(6413):10 pages.
Liu et al. (Nov. 15, 2015) "Crispr-Era: A Comprehensive Design Tool for CRISPR-Mediated Gene Editing, Repression and Activation", Bioinformatics, 31(22):3676-3678.
Liu et al. (Oct. 2014) "Integrase-Deficient Lentivirus: Opportunities and Challenges for Human Gene Therapy", Current Gene Therapy, 14(5):352-364.
Madabhushi et al. (Jun. 18, 2015) "Activity-Induced DNA Breaks Govern the Expression of Neuronal Early-Response Genes", Cell, 161(7):1592-1605.
Mali et al. (Sep. 2013) "CAS9 Transcriptional Activators for Target Specificity Screening and Paired Nickases for Cooperative Genome Engineering", Nature Biotechnology, 31(9):17 pages.
Manjunath et al. (Nov. 14, 2013) "Newer Gene Editing Technologies toward HIV Gene Therapy", Viruses, 5 (11):2748-2766.
Mannino et al. (Jul. 1, 1988) "Liposome Mediated Gene Transfer", BioTechniques, 6(7):682-690.
Manoharan M. (Dec. 10, 1999) "2'-Carbohydrate Modifications in Antisense Oligonucleotide Therapy: Importance of Conformation, Configuration and Conjugation", Biochimica et Biophysica Acta—Gene Structure and Expression, 1489(1):117-130.
Manoharan et al. (Oct. 28, 1992) "Chemical Modifications to Improve Uptake and Bioavailability of Antisense Oligonucleotides", Annals of the New York Academy of Sciences banner, Antisense Strategies, 660(1):306-309.
Manoharan et al. (Apr. 21, 1994) "Cholic Acid-Oligonucleotide Conjugates for Antisense Applications", Bioorganic & Medicinal Chemistry Letters, 4(8):1053-1060.
Manoharan et al. (Dec. 1993) "Introduction of a Lipophilic Thioether Tether in the Minor Groove of Nucleic Acids for Antisense Applications", Bioorganic & Medicinal Chemistry Letters, 3(12):2765-2770.
Manoharan et al. (May 22, 1995) "Lipidic Nucleic Acids", Tetrahedron Letters, 36(21):3651-3654.
Manoharan et al. (1995) "Oligonucleotide Conjugates: Alteration of the Pharmacokinetic Properties of Antisense Agents", Nucleosides and Nucleotides, 14(3-5):969-973.
Maurer et al. (1989) "Cationic Liposome-Mediated Transfection of Primary Cultures of Rat Pituitary Cells", Focus, 11 (2):25-27.
Nielsen et al. (Dec. 6, 1991) "Sequence-Selective Recognition of DNA by Strand Displacement with a Thymine-Substituted Polyamide", Science, 254(5037):1497-1500.
Oberhauser et al. (Feb. 11, 1992) "Effective Incorporation of 2'-O-Methyl-Oligoribonucleotides into Liposomes and Enhanced Cell Association through Modification with Thiocholesterol", Nucleic Acids Research, 20(3):533-538.

(56) References Cited

OTHER PUBLICATIONS

Peng et al. (Oct. 2015) "CRISPR/Cas9-based tools for targeted genome editing and replication control of HBV", Virologica Sinica, 30(5):317-325.
Qiu P et al. (Apr. 2004) "Mutation Detection using Surveyor Nuclease", Biotechniques, 36(4):702-707.
Ramanan et al. (Dec. 2015) "CRISPR/Cas9 cleavage of viral DNA efficiently suppresses hepatitis B virus", Scientific Reports, 5:09 pages.
Ran et al. (Sep. 12, 2013) "Double Nicking by RNA-Guided CRISPR Cas9 for Enhanced Genome Editing Specificity", Cell, 154(6):1380-1389.
Ran et al. (Apr. 9, 2015) "In Vivo Genome Editing Using *Staphylococcus aureus* Cas9", Nature, 520:28 pages.
Saison-Behmoaras et al. (1991) "Short Modified Antisense Oligonucleotides Directed Against Ha-ras Point Mutation Induce Selective Cleavage of the mRNA and Inhibit T24 Cells Proliferation", EMBO Journal, 10(5):1111-1118.
Sander et al. (Aug. 5, 2011) "Targeted Gene Disruption in Somatic Zebrafish Cells Using Engineered TALENs", Nature Biotechnology, 29(8):6 pages.
Sanghvi et al. (1993) "Antisense Research and Applications", Stanley T. Crooke, Bernard Lebleu eds., CRC Press, Boca Raton, 276-278.
Scheit Karlh., (1980) "Nucleotide Analogs—Synthesis and Biological Function", FEBS Letters, 122(2):01 page.
Shea et al. (Jul. 11, 1990) "Synthesis, Hybridization Properties and Antiviral Activity of Lipid-Oligodeoxynucleotide Conjugates", Nucleic Acids Research, 18(13):3777-3783.
Smith et al. (Jul. 2014) "Whole-Genome Sequencing Analysis Reveals High Specificity of CRISPR/Cas9 and TALEN-Based Genome Editing in Human iPSCs", Cell Stem Cell, 15(1):3 pages.
Song et al. (Oct. 2015) "Visualization and Quantification of Simian Immunodeficiency Virus-Infected Cells using Non-Invasive Molecular Imaging", Journal of General Virology, 96:3131-3142.
Stone et al. (May 2013) "Targeted Gene Disruption to Cure HIV", Current Opinion in HIV and AIDS, 8(3):12 pages.
Svinarchuk et al.(1993) "Inhibition of HIV Proliferation in MT-4 Cells by Antisense Oligonucleotide Conjugated to Lipophilic Groups", Biochimie, 75(1-2):49-54.
Toulme Jean-Jacques, (Jan. 1, 2001) "New Candidates for True Antisense", Nature Biotechnology, 19 (1):17-18.
Tsai et al. (Jun. 2014) "Dimeric CRISPR RNA-Guided FokI Nucleases for Highly Specific Genome Editing", Nature Biotechnology, 32(6):569-576.
Uhlmann E. (Mar. 2000) "Recent Advances in Medicinal Chemistry of Antisense Oligonucleotides", Current Opinion in Drug Discovery & Development, 3(2):203-213.
Veres et al. (Jul. 3, 2014) "Low Incidence of Off-Target Mutations in Individual CRISPR-Cas9 and TALEN Targeted Human Stem Cell Clones Detected by Whole-Genome Sequencing", Cell Stem Cell, 15:27-30.
Wang et al. (Dec. 26, 2014) "Gene Disruption via Lentiviral Vectors Expressing Cas9 and Single Guided RNA Renders Cells Resistant to HIV-1 Infection", PLoS One, e115987, 9(12):26 pages.
Wyvekens et al. (Jul. 2015) "Dimeric CRISPR RNA-Guided FokI-dCas9 Nucleases Directed by Truncated gRNAs for Highly Specific Genome Editing", Human Gene Therapy, 26(7):425-431.
Yang et al. (Nov. 26, 2014) "Targeted and Genome-Wide Sequencing Reveal Single Nucleotide Variations Impacting Specificity of Cas9 in Human Stem Cells", Nature Communications, 5(5507):06 pages.
Yu et al. (Jun. 5, 2014) "A PCR Based Protocol for Detecting Indel Mutations Induced by TALENs and CRISPR/Cas9 in Zebrafish", PLoS ONE, e98282, 9(6):07 pages.
Yuen et al. (Mar. 2015) "CRISPR/Cas9-Mediated Genome Editing of Epstein-Barr Virus in Human Cells", Journal of General Virology, 96(Pt. 3):626-636.
Zuckermann et al. (2015) "Somatic CRISPR/Cas9-Mediated Tumour Suppressor Disruption Enables Versatile Brain Tumour Modelling", Nature Communications, 6(7391):09 pages.
Wei et al. (2014) "Application of CRISPR/Cas9 System for Gene Regulation", Acta Veterinaria et Zootechnica Sinica, 45(9):1387-1392.
Hu et al., "RNA-Directed Gene Editing Specifically Eradicates Latent and Prevents New HIV-1 Infection," Proceedings of the National Academy of Sciences, 111:31, pp. 114612-11466, 2014.
Wigdahl, "HIV Excision Utilizing CRISPR/Cas9 Technology: Attacking the proviral Quasispecies in Reservoirs to Achieve a Cure," MOJ Immunology, 1:4, pp. 1-10, 2015.
Boerner, et al., "AAV Vector-Mediated CRISPR attaches on Proviral HIV-1 Dna for Purging of Cellular Reservoirs," Molecular Therapy, vol. 23:1, 1 pages 2015.
Supplementary European Search Report from EP Application No. 16804274, dated Dec. 13, 2018, pp. 1-3.
Saayman et al., The Therapeutic Application of CRISPR/Cas9 Technologies for HIV. Expert Opin Biol Ther ePub Apr. 12, 2015, vol. 15 No. 6 pp. 819-830. Especially entire article (review).
International Search Report issued in corresponding International Application No. PCT/US2016/035141, Dec. 28, 2016, 6 pages.
Written Opinion of the International Searching Authority issued in corresponding International Application No. PCT/US2016/035141, Dec. 28, 2016, 7 pages.
Sorek et al., "CRISPR-Mediated Adaptive Immune Systems in Bacteria and Archaea", 82 Annual Review of Biochemistry, pp. 237-266, 2013.
Hu et al., "RNA-Directed Gene Editing Specifically Eradicates Latent and Prevents New HIV-1 Infection," 111:31, Proceedings of the National Academy of Sciences, 11461-11466, Aug. 5, 2014.
Koonin et al., "Diversity, Classification and Evolution of CRISPR-Cas Systems," 37 Current Opinion in Microbiology, pp. 67-78, 2017.
Brander et al., "Lack of Strong Immune Selection Pressure by the Immunodominant, HLA-A*0201-Restricted Cytotoxic T Lymphocyte Response in Chronic Human Immunodeficiency Virus-1 Infection," Journal of Clinical Investigation, 101:11, pp. 2559-2566, 1998.
Chang et al., (2013) Genome Editing with RNA-Guided Cas9 nuclease in zebrafish embryos, Cell Research 23: 465-472.
Cong et al., (2013) Multiplex Genome Engineering Using CRISPR/Cas Systems, Science 3;339(6121): 819-823.
Esvelt et al., (2013) Orthogonal Cas9 proteins for RNA-guided gene regulation and editing, Author manuscript, Published in final edited form as: Nature Methods 10(11):1116-1121.
Gilbert et al., (2013) CRISPR-mediated modular RNA-guided regulation of transcription in eukaryotes, Cell Research, 154:442-451.
Horvath et al., (2010) CRISPR/Cas, the immune system of bacteria and archaea, Science, 327: 167-170.
Hsu et al., (2013) DNA targeting specificity of RNA-guided Cas9 nucleases, Nature Biotechnology, 31, 827-832.
Hwang et al., (2013) Efficient In Vivo Genome Editing Using RNA-Guided Nucleases, Author manuscript, Published in final edited form as: "Efficient genome editing in zebrafish using a CRISPR-Cas system," Nature Biotechnology, 31(3): 227-229.
Jiang et al., (2015) CRISPR-Cas: New Tools for Genetic Manipulations from Bacterial Immunity Systems, Annu Rev Microbiol. 2015:69:209-28.
Jinek et al., (2012) A programmable dual RNA-guided DNA endonuclease in adaptive bacterial immunity, Science 337 (6089): 816-821.
Jinek et al., (2013) RNA-programmed genome editing in human cells, eLife, 2(e0047): 1-9.
Kleinstiver et al., (2016) High fidelity CRISPR-Cas9 nucleases with no detectable genome-wide off-target effects Author manuscript, Published in final edited form as: Nature, 529 (7587): 490-495.
Lin et al., (2014) The CRISPR/Cas9 system facilitates clearance of the intrahepatic HBV templates in vivo, Molecular Therapy—Nucleic Acids (2014), 3: e186, pp. 1-7.

(56) References Cited

OTHER PUBLICATIONS

Maggio et al., (2014) Adenoviral Vector Delivery of RNA-Guided CRISPR/Cas9 Nuclease Complexes Induces Targeted Mutagenesis in a Diverse Array of Human Cells, Scientific Reports, vol. 4, No. 5105.
Mali et al., (2013) RNA-guided human genome engineering via Cas9, Science, 339(6121): 823-826.
Ramalingam et al., (2013) A CRISPR way to engineer the human genome, Genome Biology, 14(107).
Schiffer et al., (2012) Targeted DNA mutagenesis for the cure of chronic viral infections, Journal of Virology 86(17): 8920-8936.
Silva et al., (2011) Meganucleases and Other Tools for Targeted Genome Editing: Perspectives and Challenges for Gene Therapy, Curr Gene Ther 11(1): 11-27.
Wang et al., (Mar. 2016) CRISPR-Cas9 can inhibit HIV-1 Replication but NHEJ repair facilitates virus escape, Molecular therapy, 24(3): 522-526.
Xie et al., (2014) sgRNAcas9: a software package for designing CRISPR sgRNA and evaluating potential off-target cleavage sites, PLOS One 9.6 (2014): e100448.
Yin et al., (2016) Functional Screening of Guide RNAs targeting the regulatory and structural HIV-1 viral genome for a cure of AIDS, AIDS, 30(8): 1163-1174.

\* cited by examiner

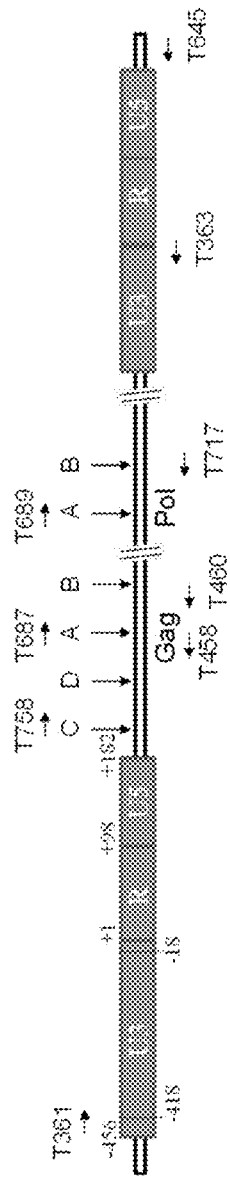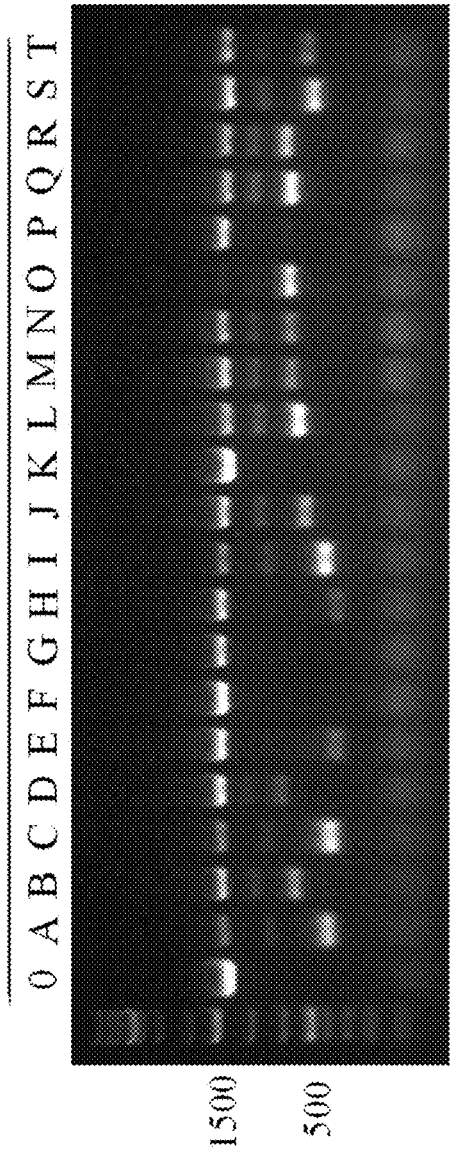
FIG. 3A

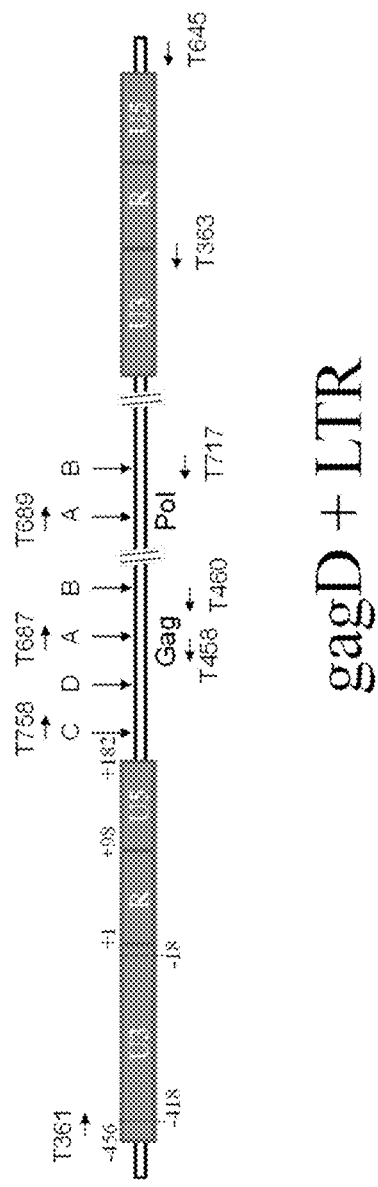
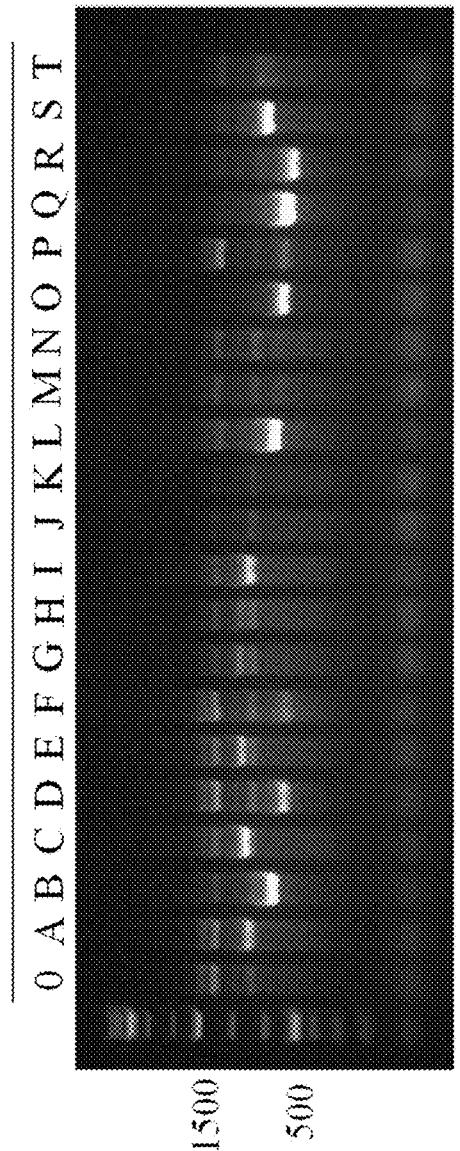
FIG. 3B

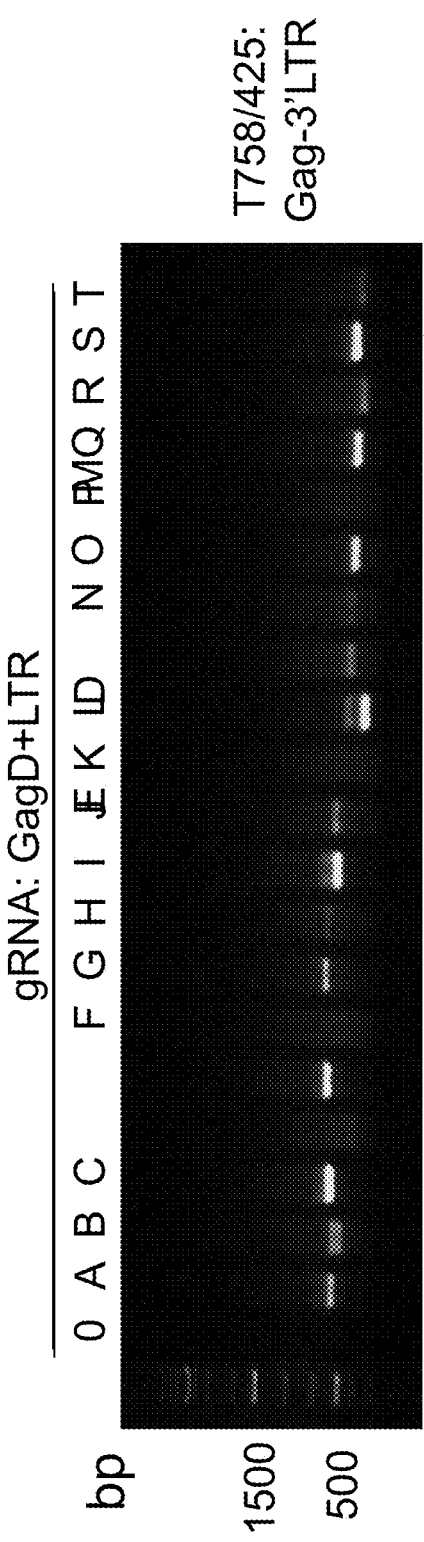
FIG. 3F
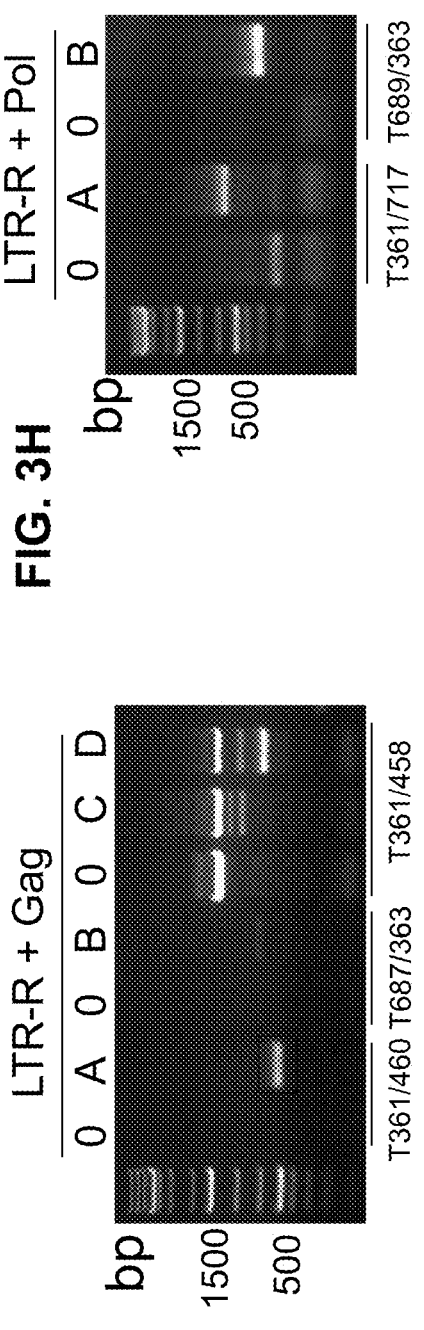
FIG. 3G
FIG. 3H

FIG 5C SEQ ID NO: 65

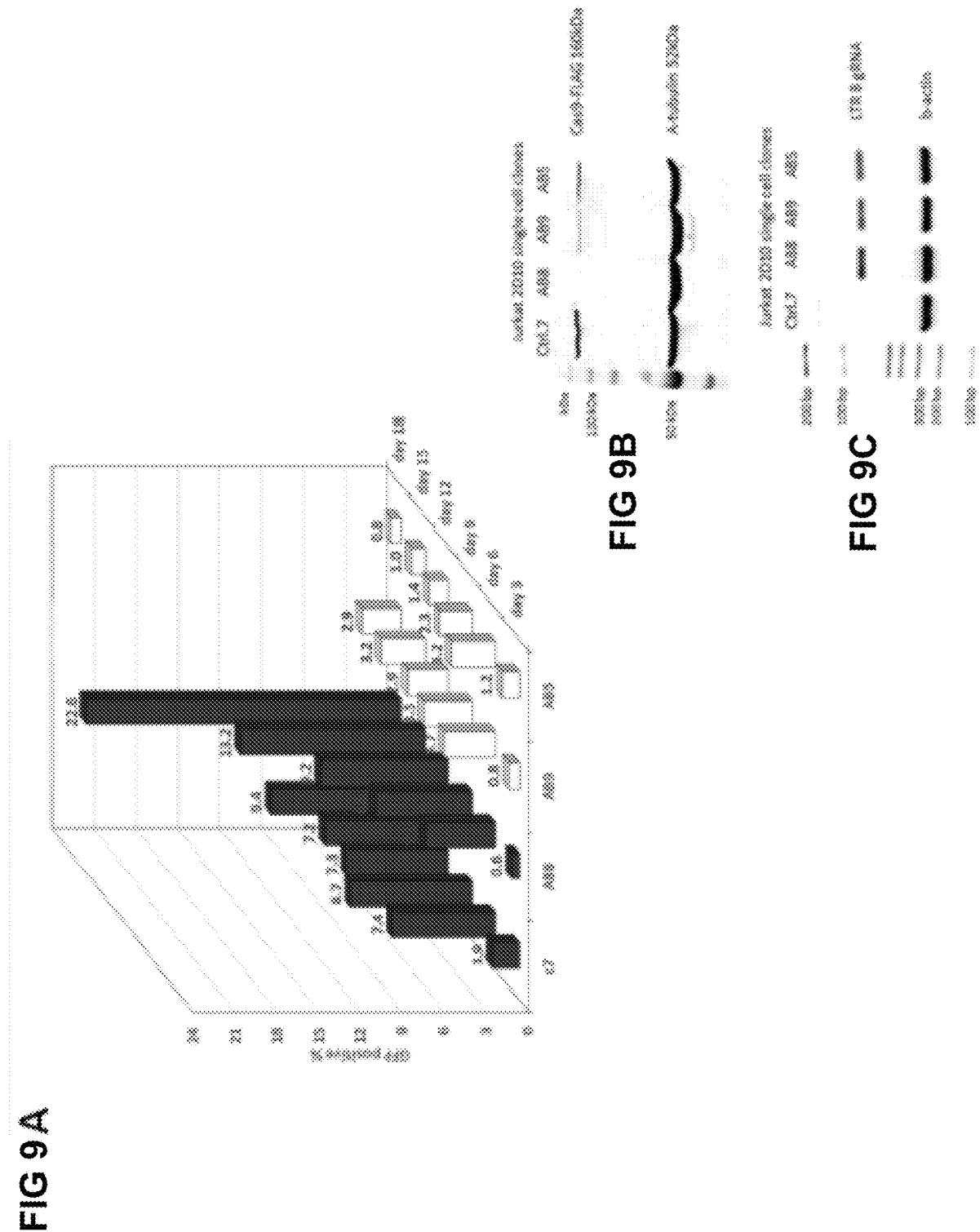

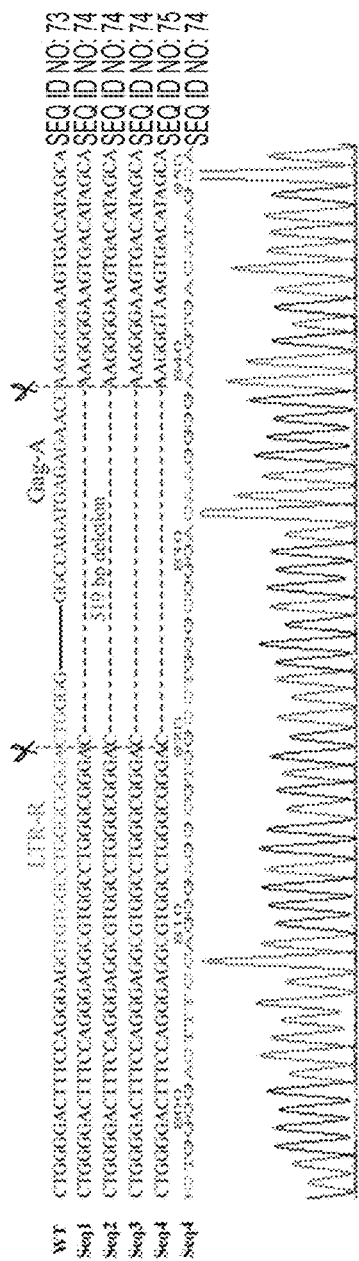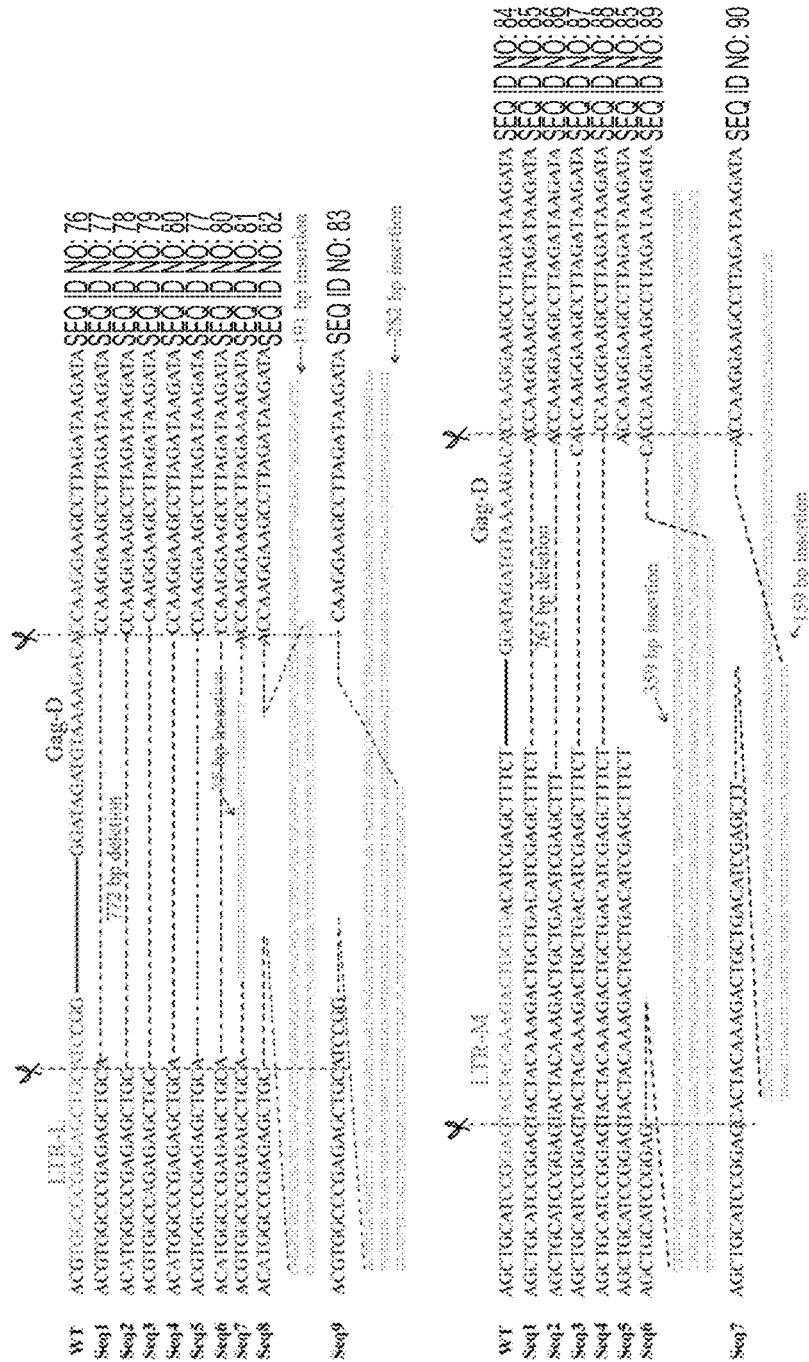
FIG. 12A
FIG. 12B
FIG. 12C

METHODS AND COMPOSITIONS FOR RNA-GUIDED TREATMENT OF HIV INFECTION

CROSS-REFERENCE TO RELATED APPLICATIONS

This application is a continuation of U.S. application Ser. No. 15/578,372, filed Nov. 30, 2017, which is a National Stage pursuant to 35 U.S.C. § 371, of International Application No. PCT/US2016/035141, filed Jun. 1, 2016, which claims the benefit of U.S. Provisional Patent Application No. 62/308,320, filed on Mar. 15, 2016, U.S. Provisional Patent Application No. 62/169,633, filed on Jun. 2, 2015 and to U.S. Provisional Patent Application No. 62/169,384, filed Jun. 1, 2015. The entire contents of the preceding patent applications are hereby incorporated by reference herein.

STATEMENT REGARDING FEDERALLY SPONSORED RESEARCH

This invention was made with government support under under P30 MH092177, R01MH093271, and R01 NS087971 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on May 19, 2020, is named 062851-504N01US_SL.txt and is 23,361 bytes in size.

FIELD OF THE INVENTION

The present invention relates to compositions and methods to specifically cleave target sequences in retroviruses, for example human immunodeficiency virus (HIV). The compositions, which can include nucleic acids encoding a Clustered Regularly Interspace Short Palindromic Repeat (CRISPR) associated endonuclease and a guide RNA sequence complementary to a target sequence in a human immunodeficiency virus, can be administered to a subject having or at risk for contracting an HIV infection.

BACKGROUND

For more than three decades since the discovery of HIV-1, AIDS remains a major public health problem affecting greater than 35.3 million people worldwide. AIDS remains incurable due to the permanent integration of HIV-1 into the host genome. Current therapy (highly active antiretroviral therapy or HAART) for controlling HIV-1 infection and impeding AIDS development profoundly reduces viral replication in cells that support HIV-1 infection and reduces plasma viremia to a minimal level. But HAART fails to suppress low level viral genome expression and replication in tissues and fails to target the latently-infected cells, for example, resting memory T cells, brain macrophages, microglia, and astrocytes, gut-associated lymphoid cells, that serve as a reservoir for HIV-1. Persistent HIV-1 infection is also linked to co-morbidities including heart and renal diseases, osteopenia, and neurological disorders. There is a continuing need for curative therapeutic strategies that target persistent viral reservoirs.

Current therapy for controlling HIV-1 infection and preventing AIDS progression has dramatically decreased viral replication in cells susceptible to HIV-1 infection, but it does not eliminate the low level of viral replication in latently infected cells which contain integrated copies of HIV-1 proviral DNA. There is an urgent need for the development of for curative therapeutic strategies that target persistent viral reservoirs, including strategies for eradicating proviral DNA from the host cell genome.

In recent years, several novel systems for eradicating endogenous genes have been developed including homing endonucleases (HE), zinc finger nucleases (ZFN), transcription activator-like effector nucleases (TALEN) and CRISPR-associated system 9 (Cas9) proteins.

In the CRISPR (Clustered Regularly Interspace Short Palindromic Repeat) method, gene editing complexes are assembled, including a Cas9 nuclease and a guide RNA (gRNA) complementary to a target a viral DNA sequence. The gRNA directs the Cas9 nuclease to engage and cleave viral DNA strands containing the target sequence. The Cas9/gRNA gene editing complex introduces one or more mutations into the viral DNA.

The feasibility of genetically disrupting the integrated HIV-1 provirus using HE to target the conserved viral protein sequences has been reported. ZFNs targeting HIV-1 host co-receptor CCR5 gene have entered phase 2 clinical trials for the treatment of HIV/AIDS. TALEN has been experimentally shown to effectively cleave CCR5 at the expected site. Cas9/gRNA editing complexes have been also used to disrupt HIV-1 entry co-receptors (CCR5, CXCR4) and proviral structural proteins (Manjunath et al., *Viruses*, 14; 5(11):2748-2766 (2013); Stone et al., *Curr. Opin. HIV AIDS.* 8(3):217-223 (2013); Wang et al., *PLoS One.* 26; 9(12):e115987 (2014)). However, CCR5 is not the unique receptor for HIV-1 infection and has many other cellular functions as well.

SUMMARY

The present invention provides compositions and methods relating to treatment and prevention of retroviral infections, especially the human immunodeficiency virus HIV. The compositions and methods attack proviral HIV that has been integrated into the genome of host cells.

Specifically, the present invention provides compositions including a nucleic acid sequence encoding a CRISPR-associated endonuclease, and one or more isolated nucleic acid sequences encoding gRNAs, wherein each gRNA is complementary to a target sequence in a retroviral genome. In a preferred embodiment, two gRNAs are included in the composition, with each gRNA directing a Cas endonuclease to a different target site in integrated retroviral DNA HIV DNA. The DNA extending between the cut sites is deleted, resulting in the excision of part or all of the HIV genome. The most effective combinations of gRNAs include pairs in which one gRNA targets a site in the LTR region and the other, targets a site in a structural gene such as gag or pol; and pairs in which both gRNAs target sites in the LTR.

The present invention also provides a method of inactivating a retrovirus in a mammalian cell by exposing the cell to a composition including one or more isolated nucleic acids encoding a gene editing complex. The gene editing complex includes a CRISPR-associated endonuclease and one or more gRNAs, wherein each gRNA is complementary to a target sequence in the retrovirus.

The present invention further provides a pharmaceutical composition for the inactivation of integrated retroviral proviral DNA in a mammalian subject. The composition includes an isolated nucleic acid sequence encoding a Cas endonuclease, and at least one isolated nucleic acid sequence encoding at least one gRNA complementary to a target sequence in a proviral retroviral DNA, such as HIV DNA. Pairs of gRNAs targeting different sites in the retroviral genome are preferred. The isolated nucleic acid sequences are included in at least one expression vector.

The present invention still further provides a method of treating a mammalian subject infected with a retrovirus, e.g. HIV. The method includes the steps of determining that a mammalian subject is infected with HIV, administering an effective amount of the previously stated pharmaceutical composition, and treating the mammalian subject for HIV infection.

The present invention also provides a method of treatment to reduce the risk of a retrovirus (e.g. HIV) infection in a mammalian subject at risk for infection. The method includes the steps of determining that a mammalian subject is at risk of HIV infection, administering an effective amount of the previously stated pharmaceutical composition, and reducing the risk of HIV infection in a mammalian subject.

The present invention further provides a kit for the treatment or prophylaxis of HIV infection. The kit includes a measured amount of a composition comprising at least one isolated nucleic acid sequence encoding a CRISPR-associated endonuclease, and at least one nucleic acid sequence encoding one or more gRNAs, wherein the gRNAs are complementary to target sites in HIV. Alternatively, the kit can include one or more vectors encoding the nucleic acids. The kit can also contain packaging material, a package insert with instructions for use, a sterile fluid, a syringe, and/or a sterile container.

Figure 3C:
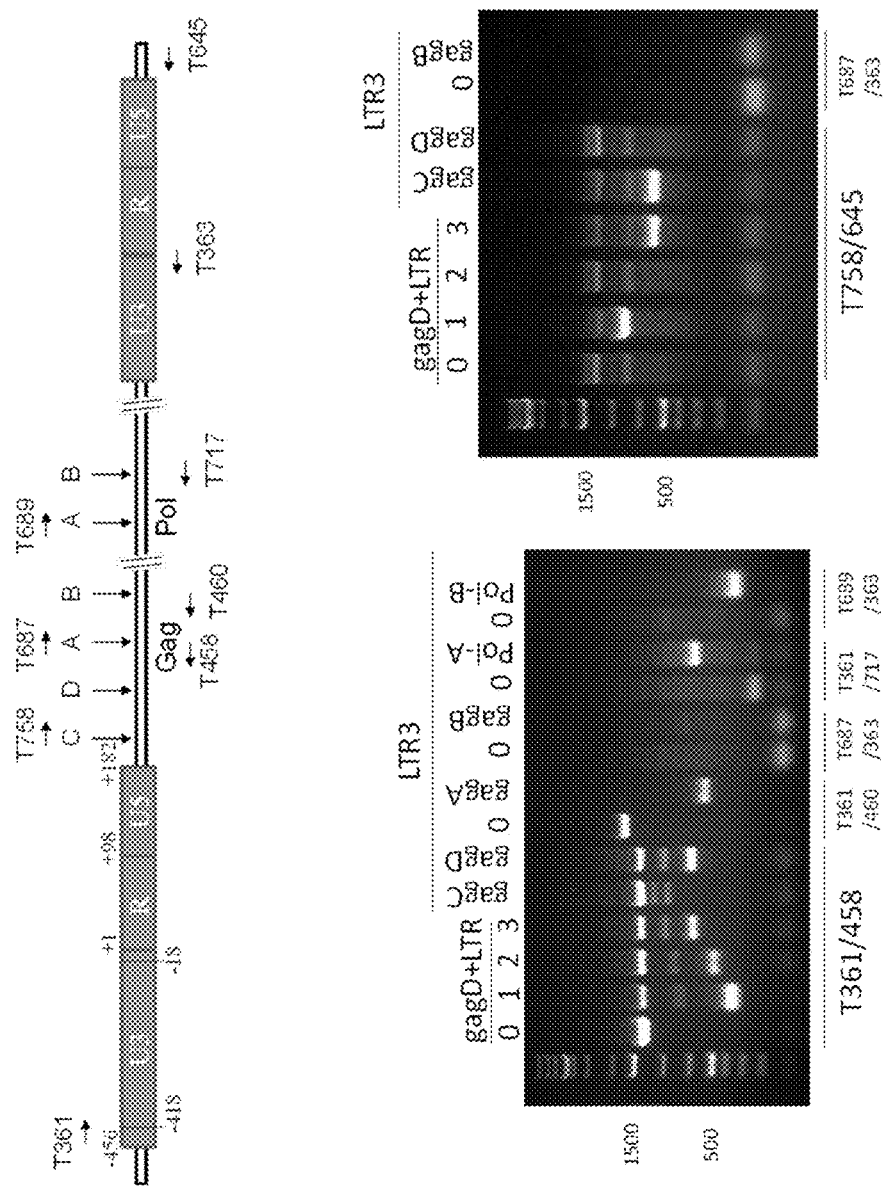
FIG. 3C shows that PCR genotyping verified the eradication of HIV-1 DNA between LTR-3 targeting site and Gag or Pol targeting sites. Top panel: Location of PCR primers. Bottom panel: GagD paired with LTR-1, 2, 3 or LTR-3 sgRNA paired with various sgRNAs targeting Gag or Pol. HEK293T cells were cotransfected with EcoHIV-eLuc reporter, pLV-EF1a-spCas9-T2A-RFP and indicated gRNA expression vectors. After 2 days, the cells were lysated with 50 mM NaOH at 95° C. for 10 minutes and neutralized with 1 M Tris-HCl. The crude extracts were directly used for PCR using Terra PCR Direct Polymerase Mix (Clontech) and the PCR primers covering the sequences between 5'-LTR and 5'-genome sequence (left panel) or the 3'-genome sequence and 3'-LTR (right panel)
Figure 3D:
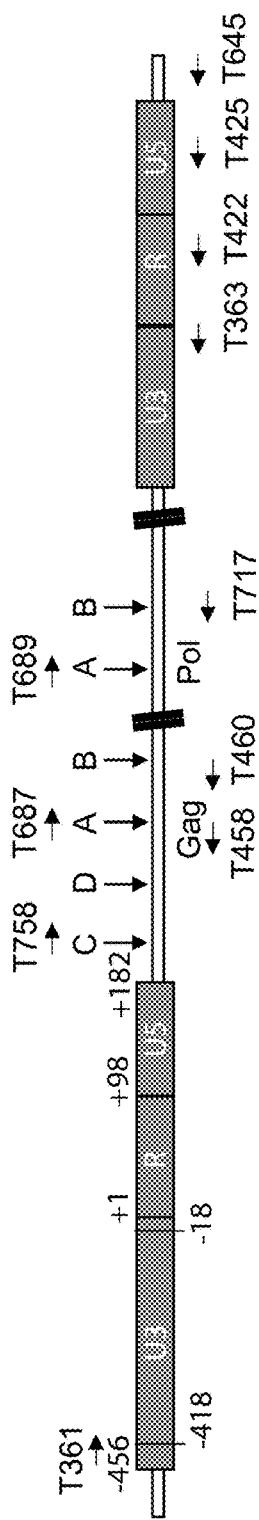
FIG. 3A shows that PCR genotyping verified the eradication of HIV-1 DNA between 5'-LTR targeting sites and Gag-D cutting site. Top panel: Location of PCR primers. Bottom panel: GagD sgRNA paired with various sgRNAs targeting LTR. HEK293T cells were cotransfected with EcoHIV-eLuc reporter, pLV-EF1a-spCas9-T2A-RFP and indicated gRNA expression vectors. After 2 days, the cells were lysated with 50 mM NaOH at 95° C. for 10 minutes and neutralized with 1 M Tris-HCl. The crude extracts were directly used for PCR using Terra PCR Direct Polymerase Mix (Clontech) and the PCR primers T361/T458 covering 5'-LTR and 5'-partial Gag (1364 bp), which produce 1.35 kb fragment in the control sample transfected with empty sgRNA expression vector.
FIG. 3B shows that PCR genotyping verified the eradication of HIV-1 DNA between 3'-LTR targeting sites and Gag-D cutting site. Top panel: Location of PCR primers. Bottom panel: GagD sgRNA paired with various sgRNAs targeting LTR. HEK293T cells were cotransfected with EcoHIV-eLuc reporter, pLV-EF1a-spCas9-T2A-RFP and indicated gRNA expression vectors. After 2 days, the cells were lysated with 50 mM NaOH at 95° C. for 10 minutes and neutralized with 1 M Tris-HCl. The crude extracts were directly used for PCR using Terra PCR Direct Polymerase Mix (Clontech) and the PCR primers T758 (nucleotide 796-817)/T645 (targeting the vector sequence after 3'LTR) covering 3'-LTR and entire HIV-1 genome except for partial 5' Gag sequence, which produces the predicted fragment of 9.5 kb undetectable by the regular PCR condition in the control sample transfected with empty sgRNA expression vector.
Figure 3E:
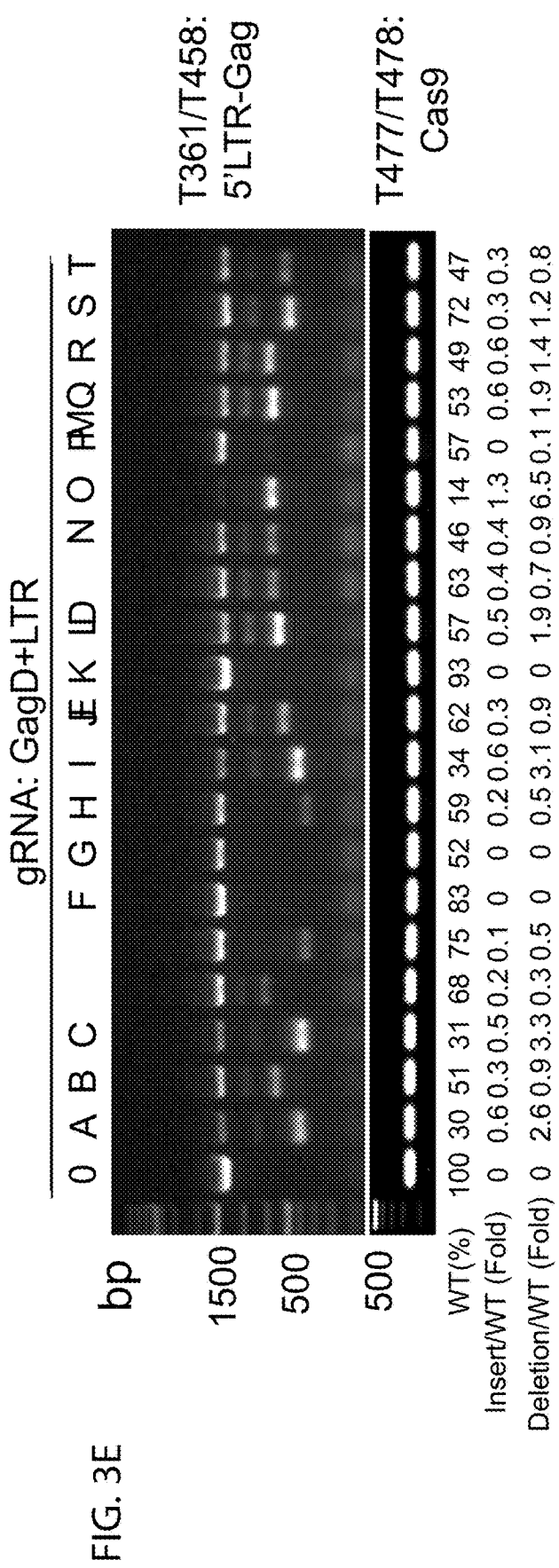
Figure 3I:
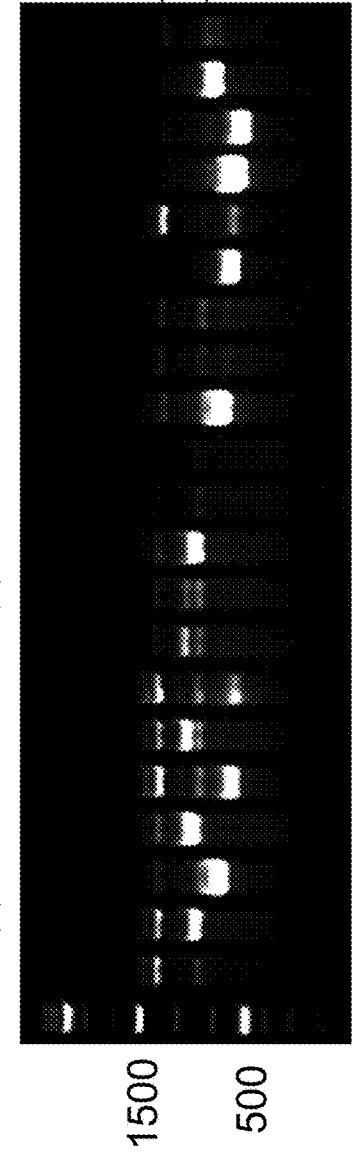
Figure 3J:
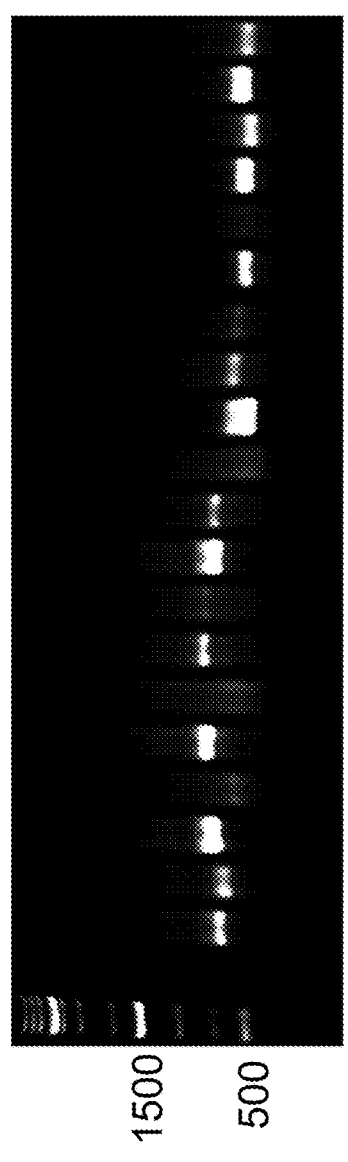
Figure 4:
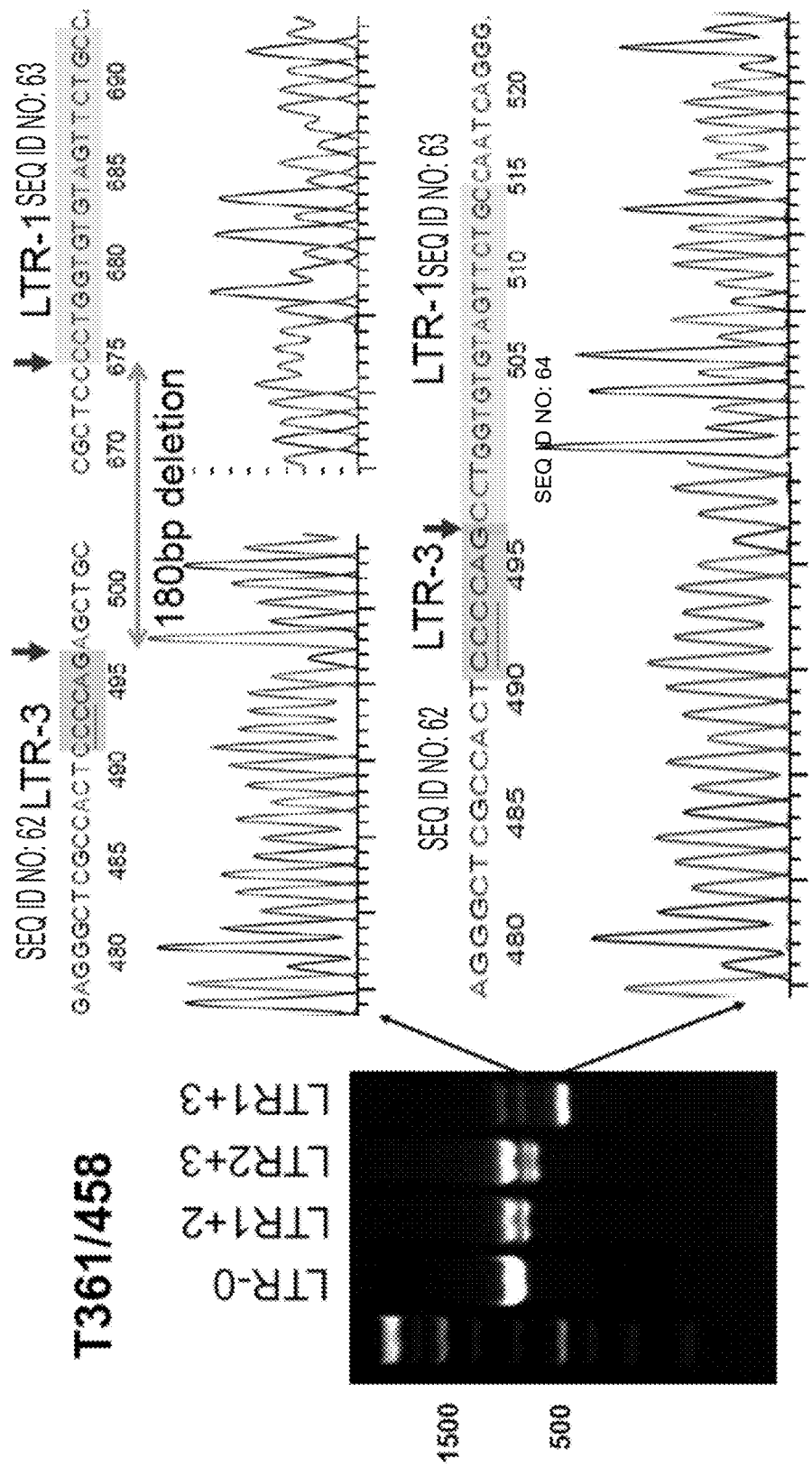
Figures 5A, 5B:
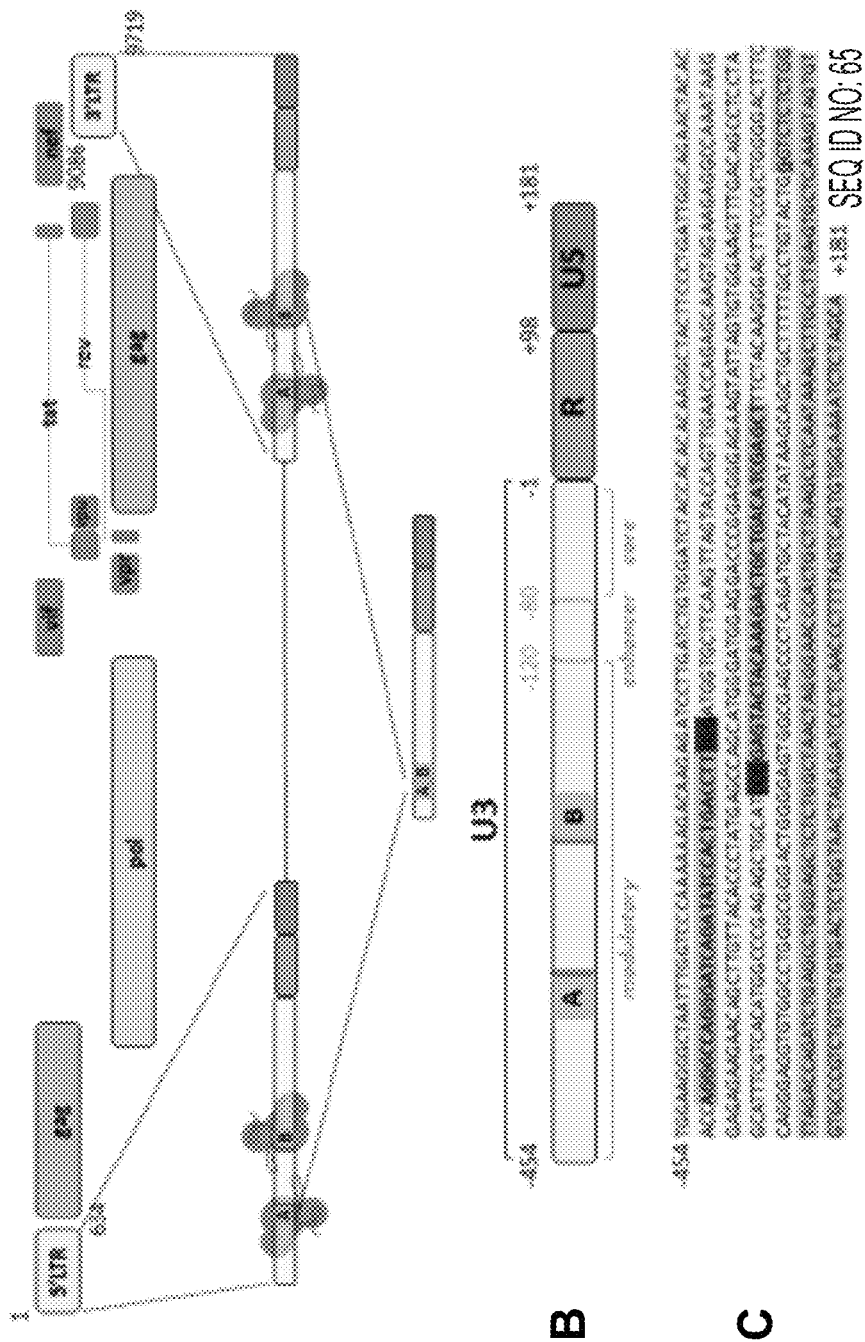
Figure 6A:
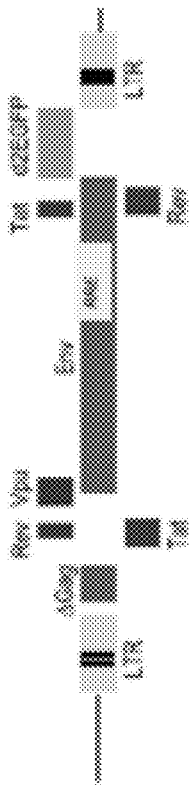
Figure 6B:
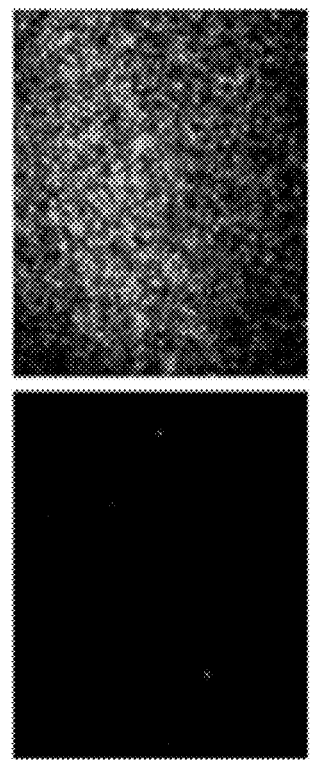
Figure 6C:
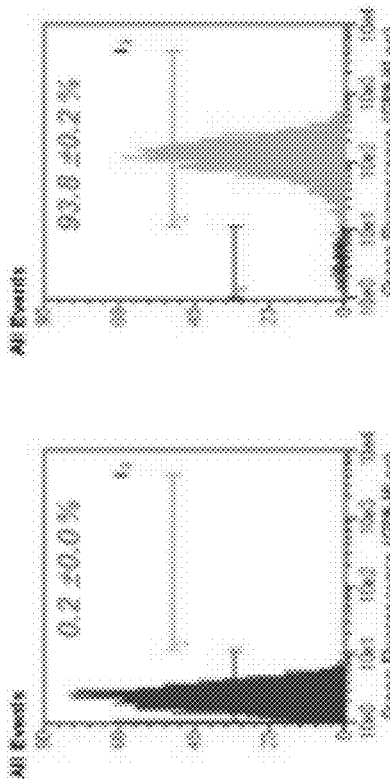
Figure 7A:
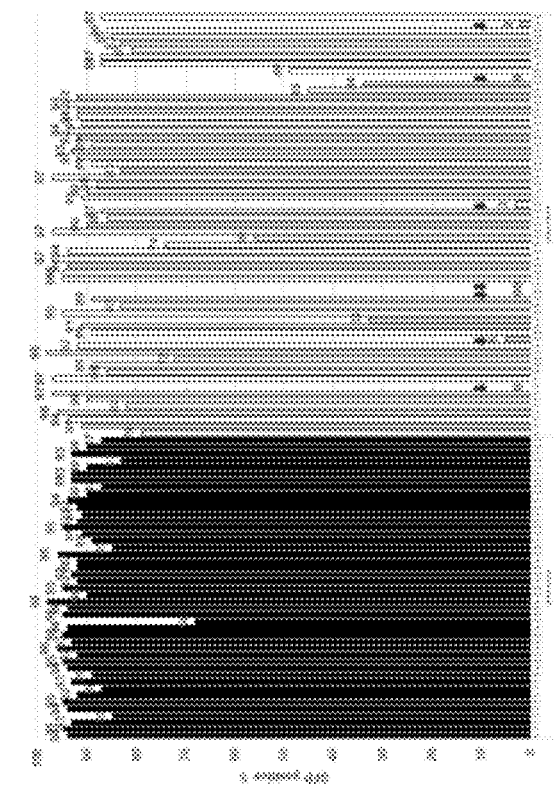
Figure 7B:
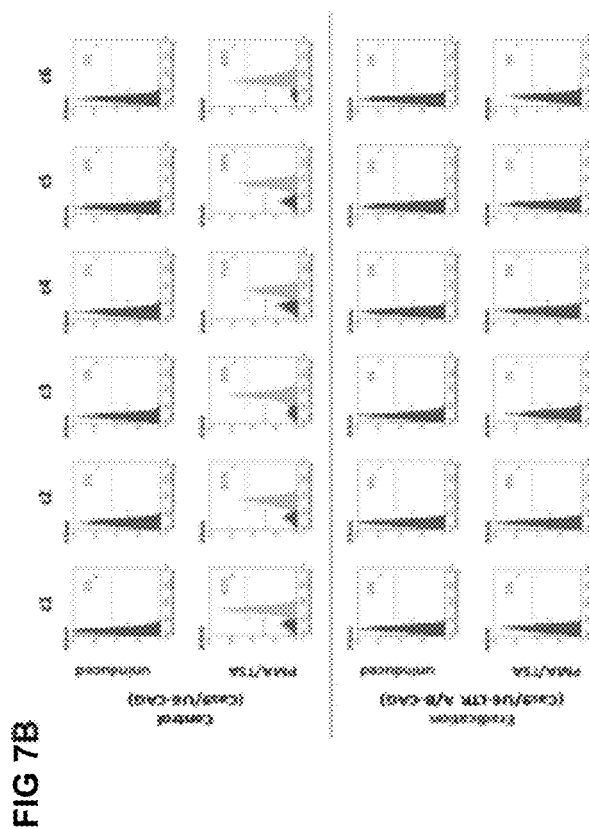
Figure 7C:
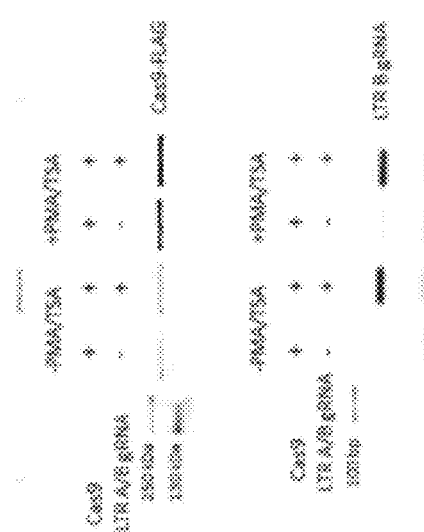
Figures 8A, 8B:
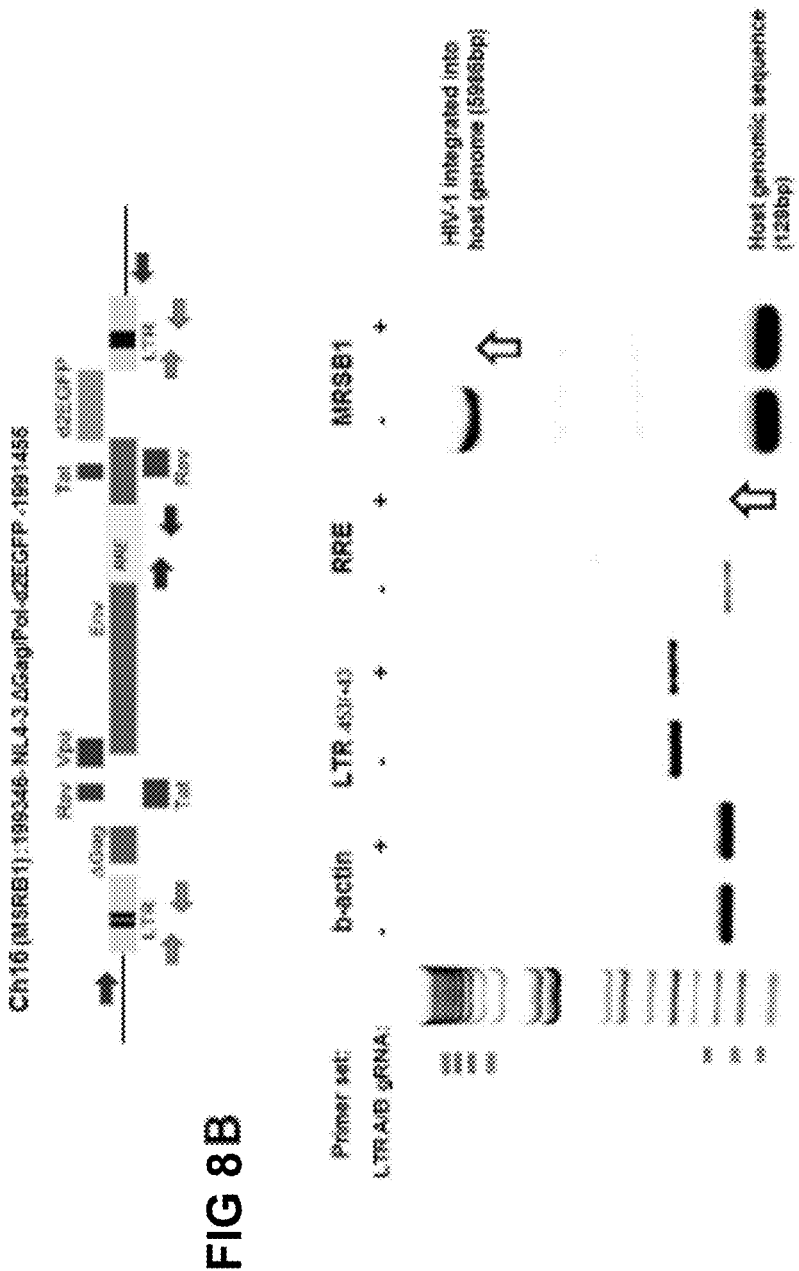
Figure 8C:
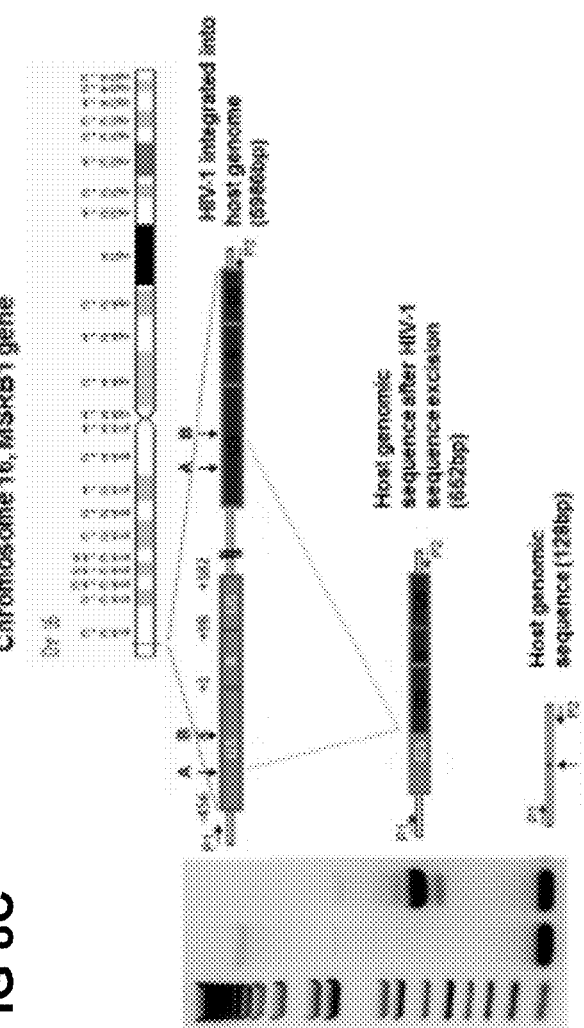
Figure 8D:
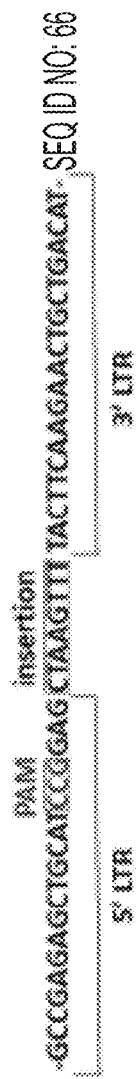
Figure 10A:
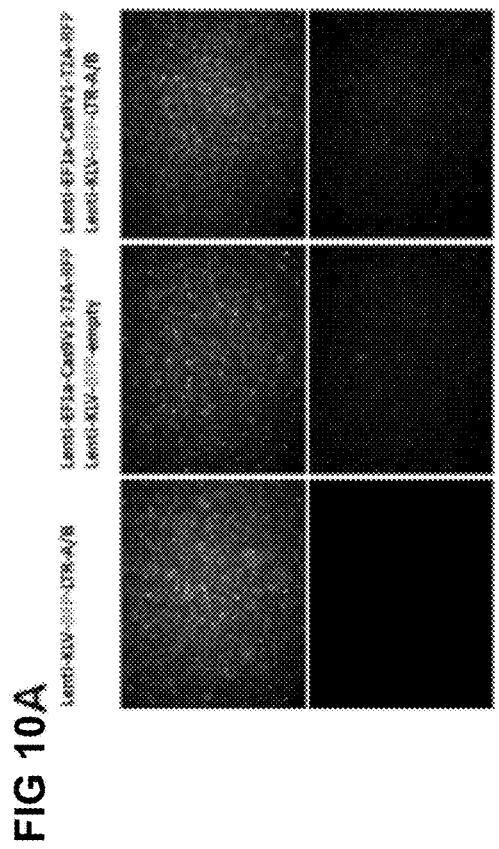
Figure 10B:
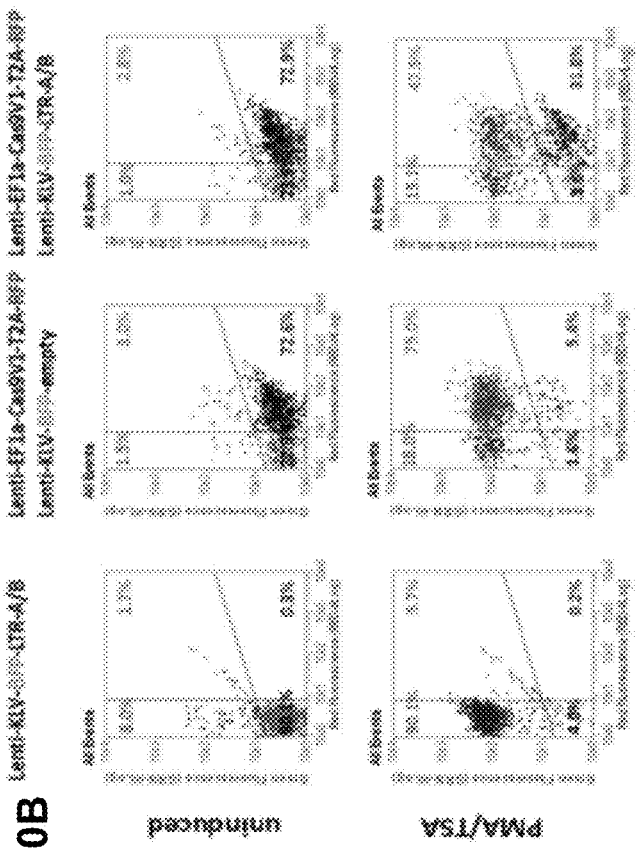
Figure 11D:
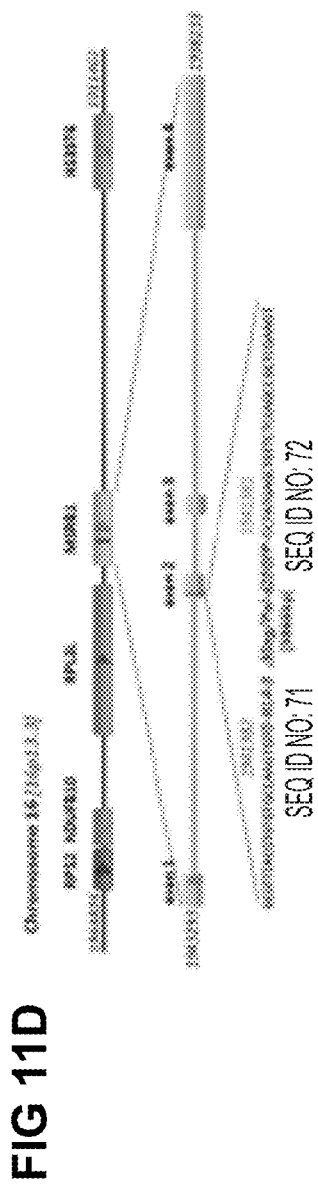
Figure 11E:
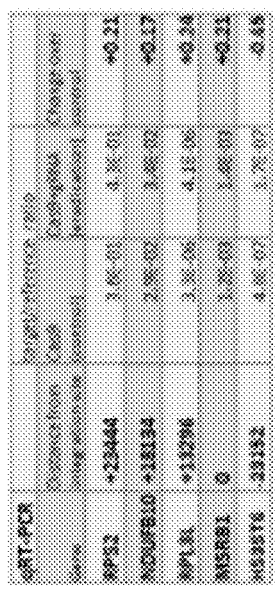
Figures 13A, 13B, 13C, 13D, 13E:
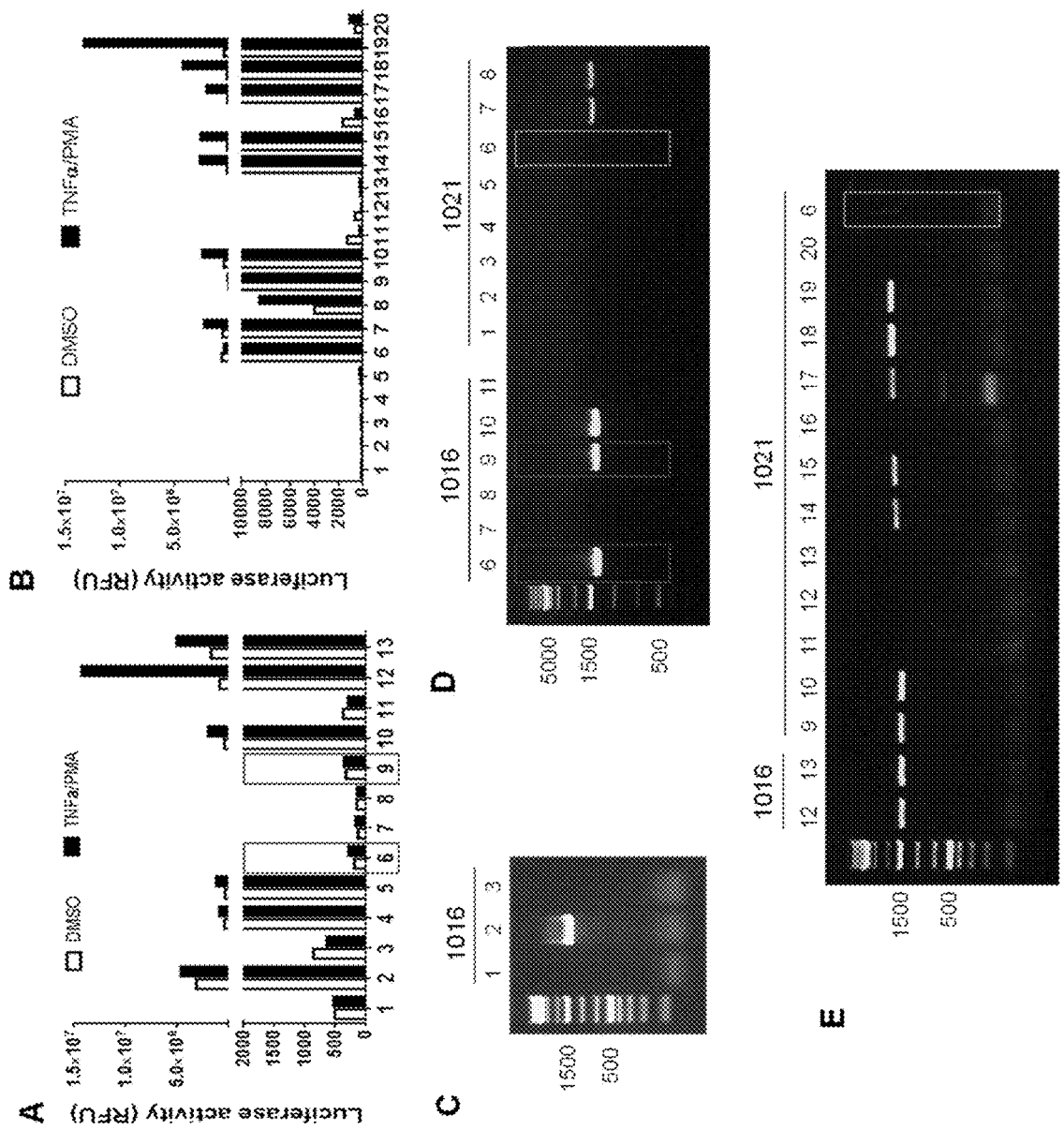
Figures 14A, 14B, 14C, 14D:
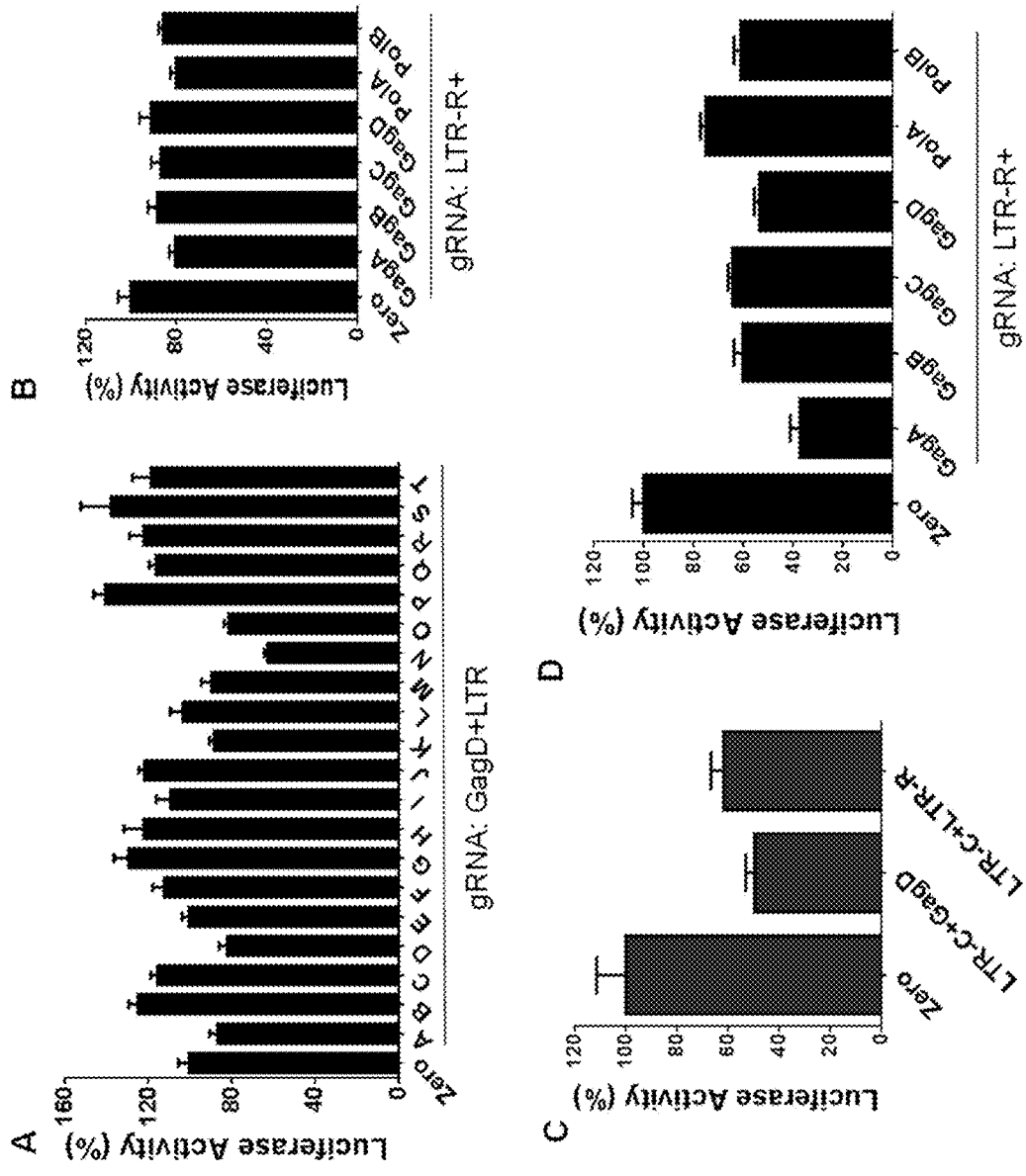

FIG. 3D shows a diagram of the location of PCR primers and Gag/Pol gRNA targeting sites used in the validation of effective gRNAs by PCR genotyping;

FIGS. 3E, 3F are blots showing the results of GagD paired with various LTR-gRNAs;

FIGS. 3G, 3H are blots showing the results of LTR-R paired with various gRNAs targeting Gag and Pol. Deletion of 5'LTR-Gag or Gag-3'LTR was detected. The band density of wild-type (WT), deletion and insertion was quantified with NIH Image J program. The number under the gel indicates WT band change (%) related to the empty gRNA control after normalization with Cas9 PCR product using Cas9 specific primers T477/T478, as well as fold changes in the insertion and deletion bands compared with WT band. The dramatic changes induced by corresponding gRNA were highlighted as boxes. The boxes indicate the selected samples for TA-cloning and Sanger sequencing;

FIGS. 3I, 3J show the further validation of effective gRNAs by Direct-PCR genotyping with additional PCR primers covering the structural region and the 3'-LTR. FIG. 3I shows the forward primer (T758) on the 5'-upstream of the gRNA GagD pairs with the reverse primer (T645) on the vector downstream of 3'-end LTR. FIG. 3J shows the forward primer (T758) on the 5'-upstream of the gRNA GagD pairs with the reverse primer (T422) on the R region of 3'-end LTR. The arrows indicate non-specific bands (ns);

FIG. 4 shows that representative TA-cloning and Sanger sequencing confirmed 296 bp deletion between LTR-1 (SEQ ID NO: 63) and LTR-3 (SEQ ID NO: 62) and 180 bp additional insertion between the two cut sites. Sample preparation and Direct PCR were performed as described in FIG. 3A. The PCR fragments after cut were extracted for TA cloning and Sanger sequence (SEQ ID NO: 64). Red arrows point the predicted cut sites at the third nucleotide from PAM. Underlined red shows the PAM sequence;

FIG. 5A shows a schematic representation of the HIV-1 genome, including a strategy and predicted result of successful targeting of viral LTR sequences (flanking integrated provirus) with Cas9/gRNA complexes;

FIG. 5B shows a detailed structure of the LTR;

FIG. 5C shows the sequence of target sites and their location in the LTR (SEQ ID NO: 65);

FIG. 6A shows a diagram of the Jurkat 2D10 reporter cell line, including a depiction of the integrated HIV-1 reporter sequence;

FIG. 6B shows fluorescence micrographs depicting PMA/TSA induced reactivation of latent proviral sequences;

FIG. 6C shows flow cytometry histograms representing PMA/TSA induced reactivation of latent proviral sequences;

FIG. 7A shows the results of a single cell clone screen;

FIG. 7B shows confirmation of best clones, according to flow cytometric analysis of clones obtained in the single cell clone screen;

FIG. 7C shows exemplary Western blots for FLAG-Cas9 (top panel) and RT-PCR agarose gel electrophoresis (bottom panel), for gRNA expression;

FIG. 8A shows the location of primers used in the PCR analysis of eradication of HIV-1 proviral genome from host DNA. The primers were specific for proviral Env gene sequence motif (RRE), genomic sequences flanking integrated reporter provirus (chromosome 16, MSRB1 gene), LTR and control b-actin gene;

FIG. 8B shows an agarose gel picture of PCR reactions, with arrows pointing to sites of bands missing due to eradication of HIV-1 sequences;

FIG. 8C shows long range PCR data under conditions optimized for shorter products, allowing detection of proviral lariat sequences at the integration site;

FIG. 8D shows sequencing results of proviral lariat (SEQ ID NO: 66);

FIG. 9A shows fluorescence analysis of Jurkat 2D10 single cell clones which had been infected with HIV-1 NL-4-3-EGFP-P2A-Nef reporter virus, with infection progression monitored for 18 days, in the form of fluorescence analysis;

FIG. 9B shows a Western blot showing Cas9-FLAG expression in tested clones;

FIG. 9C shows an agarose gel picture of reverse transcription PCR for gRNA expression in selected clones;

FIG. 10A shows fluorescence micrographs of Jurkat 2D10 cells transduced with lentiviruses expressing RFP-Cas9 and/or LTR A/B' gRNAs;

FIG. 10B shows flow cytometric analysis of RFP-Cas9 and/or LTR A/B' gRNAs expression and viral reactivation after induction with PMA/TSA;

Figures 11A, 11B, 11C:
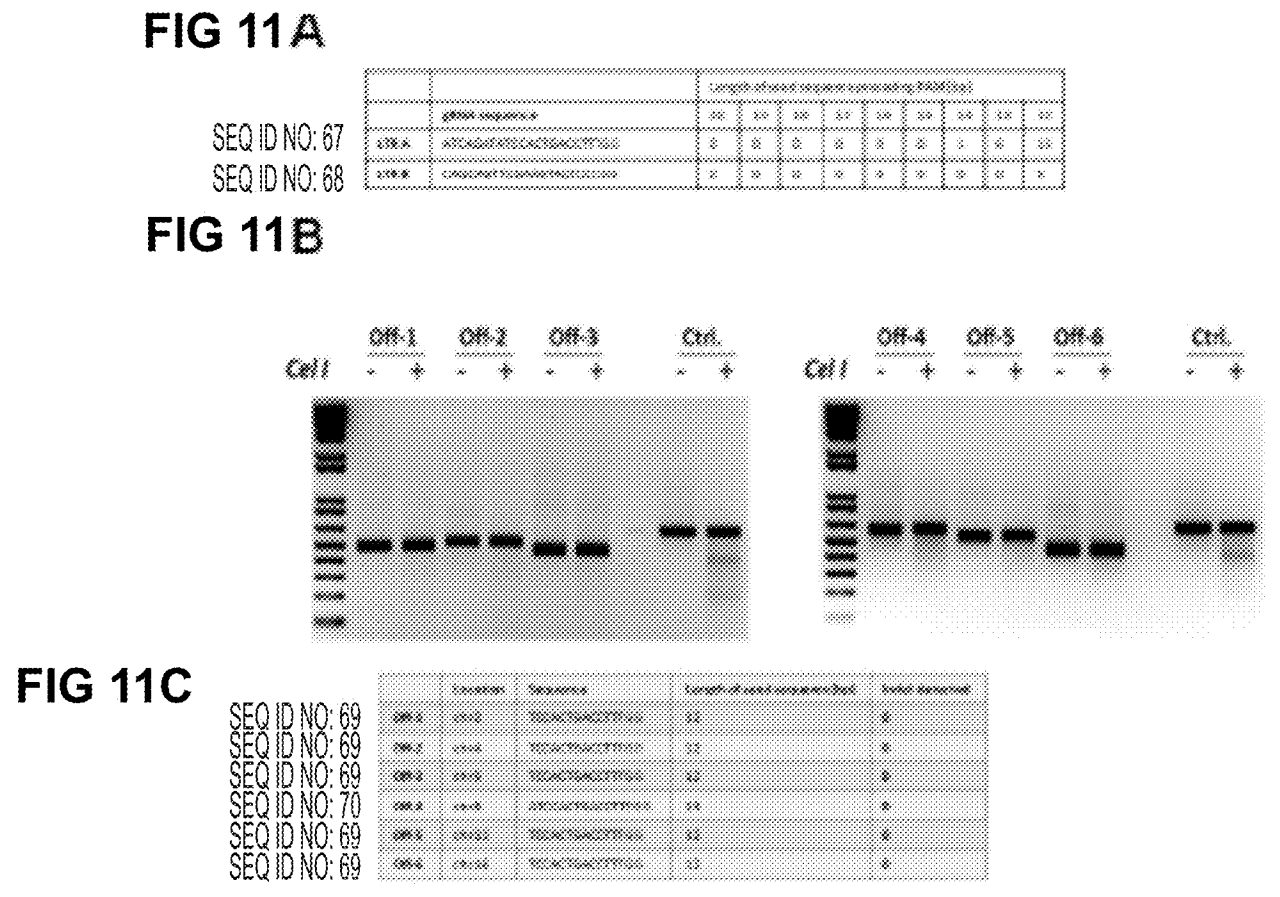

FIG. 11A shows the sequences of LTR A (SEQ ID NO: 67) and LTR B' (SEQ ID NO: 68);

FIG. 11B shows Surveyor assay analysis of off-target indels after expression of Cas9 and LTR A/B';

FIG. 11C shows the results of Sanger sequencing analysis of off-target indels (SEQ ID NOS 69, 69, 69, 70, 69, and 69, respectively, in order of appearance);

FIG. 11D shows the location of the HIV-1 reporter integration site in the second exon of the MSRB1 gene in chromosome 16, and neighboring genes (SEQ ID NOS 71 and 72, respectively, in order of appearance);

FIG. 11E shows the results of qRT-PCR comparison of expression of neighboring genes in control and Cas9/LTR AB' expressing cells;

FIGS. 12A-12C show a diagram of the TA-cloning and Sanger sequencing of representative samples confirmed the deletion of predicted fragments between corresponding gRNA target sites (FIGS. 12A-12C) and various additional insertions (FIGS. 12B, 12C). The PAM sequences are highlighted and the scissors indicate the third nucleotide from PAM. The arrow points the junction site after cleavage and ligation (FIG. 12A discloses SEQ ID NOS 73, 74, 74, 74, 75, and 74, respectively, in order of appearance; FIG. 12B discloses SEQ ID NOS 76-80, 77, and 80-83, respectively, in order of appearance; and FIG. 12C discloses SEQ ID NOS 84-88, 85, 89, and 90, respectively, in order of appearance;

FIGS. 13A-13E show the establishment of EcoHIV-firefly-luciferase stable HEK293T cell line. The EcoHIV-eLuc virus was collected at 48 h after cotransfection of HEK293T cells in one well of 6-well plate with 3 µg of pEcoHIV-eLuc plasmid and 1 µg of VSV-G plasmid. Equal volume of viral supernatant (250 µl) was added to HEK293T cells ($2\times10^4$/well) in a 12-well plate. After 48 h, the eLuc luciferase activity measured with ONE-Glo luciferase assay (Promega) showed $10^5$-fold higher than that in the control HEK293T cells without virus treatment. Then the single cells were cultured in four 96-well plates at limiting dilution. After 2-3 weeks, the surviving cell colonies were isolated and tested for eLuc reporter activity (FIGS. 13A, 13B) by ONE-Glo luciferase assay and the validation of EcoHIV-eLuc transgene by Direct-PCR genotyping (FIGS. 13C-13E) with primer T361 (5'-gatctgtggatctaccacacaca-3'(SEQ ID NO: 58)) and T458 (5'-cccactgtgtttagcatggtatt-3' (SEQ ID NO: 59)). Half of the single cell-derived 13 clones in the first round of experiment (FIG. 13A, coded as 1016) and half of the 20 clones in the second round (FIG. 13B, 1021) showed various degrees of constitutive eLuc activity. Only two of them (1016-11 and 1021-19) were significantly responsive to stimulation with TNFα (10 ng/ml) and PMA (10 ng/ml). All the eLuc-expressing clones contained the transgene (FIGS. 13C-13E) except for the clone 1021-6 (green square), which may lose the Gag sequence during integration but still transcribe eLuc via alternative splicing. Two clones (1016-6 and 1016-9) contained the transgene but showed no eLuc activity even after treatment with latency-reversing agents such as TNFα/PMA and others (red square in FIGS. 13A and 13D). Thus those clones with eLuc activity were selected and maintained for further studies. Some of these clones cannot be passaged probably due to the continuous generation of toxic viral proteins and some clones were resistant to transfection, even with lipofectamine transfection kit; and, FIGS. 14A-14D show results from the efficiency screening of gRNAs using EcoHIV-firefly-luciferase stable HEK293T cell line. FIGS. 14A, 14B: The EcoHIV-eLuc stable expressing clone was further infected with pCW-Cas9-puromycin lentivirus at 10 MOI and selected with puromycin (1 µg/ml) for 2 weeks. Cells were transfected with indicated gRNA-expressing vectors. After 2 days, ONE-Glo luciferase assay was performed. FIGS. 14C, 14D: The EcoHIV-eLuc stable expressing cells were cotransfected with indicated gRNA-expressing vectors and pLV-EF1α-spCas9-T2A-RFP vector. Luciferase activity was measured with ONE-Glo luciferase assay after 48 h. Data represent mean±SEM of 4 independent transfections with percentage changes in eLuc activity as compared with the empty gRNA Zero group.

DETAILED DESCRIPTION

The present invention is based, in part, on the discovery that integrated human immunodeficiency virus (HIV) genome can be eliminated from HIV infected cells by using the RNA-guided Clustered Regularly Interspace Short Palindromic Repeat (CRISPR)-Cas 9 nuclease system (Cas9/gRNA) in single and multiplex configurations.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used. It is also to be understood that the terminology used herein is for the purpose of describing particular embodiments only, and is not intended to be limiting.

All genes, gene names, and gene products disclosed herein are intended to correspond to homologs from any species for which the compositions and methods disclosed herein are applicable. It is understood that when a gene or gene product from a particular species is disclosed, this disclosure is intended to be exemplary only, and is not to be interpreted as a limitation unless the context in which it appears clearly indicates. Thus, for example, for the genes or gene products disclosed herein, are intended to encompass homologous and/or orthologous genes and gene products from other species.

The articles "a" and "an" are used herein to refer to one or to more than one (i.e., to at least one) of the grammatical object of the article. By way of example, "an element" means one element or more than one element. Thus, recitation of "a cell", for example, includes a plurality of the cells of the same type. Furthermore, to the extent that the terms "including", "includes", "having", "has", "with", or variants thereof are used in either the detailed description and/or the claims, such terms are intended to be inclusive in a manner similar to the term "comprising."

As used herein, the terms "comprising," "comprise" or "comprised," and variations thereof, in reference to defined or described elements of an item, composition, apparatus, method, process, system, etc. are meant to be inclusive or open ended, permitting additional elements, thereby indicating that the defined or described item, composition, apparatus, method, process, system, etc. includes those specified elements—or, as appropriate, equivalents thereof—and that other elements can be included and still fall within the scope/definition of the defined item, composition, apparatus, method, process, system, etc.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods. Alternatively, particularly with respect to biological systems or processes, the term can mean within an order of magnitude within 5-fold, and also within 2-fold, of a value. Where particular values are described in the application and claims, unless otherwise stated the term "about" meaning within an acceptable error range for the particular value should be assumed.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

An "effective amount" or "therapeutically effective amount" of a compound is that amount of compound which is sufficient to provide a beneficial effect to the subject to which the compound is administered. An "effective amount" of a delivery vehicle is that amount sufficient to effectively bind or deliver a compound.

The term "eradication" of virus, e.g. HIV, as used herein, means that that virus is unable to replicate, the genome is deleted, fragmented, degraded, genetically inactivated, or any other physical, biological, chemical or structural manifestation, that prevents the virus from being transmissible or infecting any other cell or subject resulting in the clearance of the virus in vivo. In some cases, fragments of the viral genome may be detectable, however, the virus is incapable of replication, or infection etc.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared× 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The terms "patient," "subject," "individual," and the like are used interchangeably herein, and refer to any animal or cells thereof whether in vitro or in situ, amenable to the methods described herein. In certain non-limiting embodiments, the patient, subject or individual is a human.

"Parenteral" administration of a composition includes, e.g., subcutaneous (s.c.), intravenous (i.v.), intramuscular (i.m.), or intrasternal injection, or infusion techniques.

As used herein, the terms "polynucleotide", "nucleic acid sequence" and "gene" are used interchangeably throughout the specification and include complementary DNA (cDNA), linear or circular oligomers or polymers of natural and/or modified monomers or linkages, including deoxyribonucleosides, ribonucleosides, substituted and alpha-anomeric forms thereof, peptide nucleic acids (PNA), locked nucleic acids (LNA), phosphorothioate, methylphosphonate, and the like. The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. Polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means. The nucleic acid sequences may be "chimeric," that is, composed of different regions. In the context of this invention "chimeric" compounds are oligonucleotides, which contain two or more chemical regions, for example, DNA region(s), RNA region(s), PNA region(s) etc. Each chemical region is made up of at least one monomer unit, i.e., a nucleotide. These sequences typically comprise at least one region wherein the sequence is modified in order to exhibit one or more desired properties.

"Analogs" in reference to nucleosides includes synthetic nucleosides having modified base moieties and/or modified sugar moieties, e.g., described generally by Scheit, Nucleotide Analogs, John Wiley, New York, 1980; Freier & Altmann, *Nucl. Acid. Res.*, 1997, 25(22), 4429-4443, Toulmé, J. J., *Nature Biotechnology* 19:17-18 (2001); Manoharan M., *Biochemica et Biophysica Acta* 1489:117-139 (1999); Freier S. M., Nucleic Acid Research, 25:4429-4443 (1997), Uhlman, E., *Drug Discovery & Development*, 3: 203-213 (2000), Herdewin P., *Antisense & Nucleic Acid Drug Dev.*, 10:297-310 (2000)); 2'-O, 3'-C-linked [3.2.0]bicycloarabinonucleosides (see e.g. N. K Christiensen, et al., *J. Am. Chem. Soc.*, 120: 5458-5463 (1998). Such analogs include synthetic nucleosides designed to enhance binding properties, e.g., duplex or triplex stability, specificity, or the like.

The term "variant," when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Thus, for example, the terms oligopeptide, protein, and enzyme are included within the definition of polypeptide or peptide, whether produced using recombinant techniques, chemical or enzymatic synthesis, or be naturally occurring. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins. This term also includes polypeptides that have been modified or derivatized, such as by glycosylation, acetylation, phosphorylation, and the likeamong others. The polypeptides include natural peptides, recombinant peptides, synthetic peptides, or a combination thereof.

As used herein, "variant" of polypeptides refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological activity may be found using computer programs well known in the art, for example, LASERGENE software (DNASTAR).

A "therapeutic" treatment is a treatment administered to a subject who exhibits signs of pathology, for the purpose of diminishing or eliminating those signs.

The phrase "therapeutically effective amount," as used herein, refers to an amount that is sufficient or effective to prevent or treat (delay or prevent the onset of, prevent the progression of, inhibit, decrease or reverse) a disease or condition, including alleviating symptoms of such diseases.

"Treatment" is an intervention performed with the intention of preventing the development or altering the pathology or symptoms of a disorder. Accordingly, "treatment" refers to both therapeutic treatment and prophylactic or preventative measures. "Treatment" may also be specified as palliative care. Those in need of treatment include those already with the disorder as well as those in which the disorder is to be prevented. Accordingly, "treating" or "treatment" of a state, disorder or condition includes: (1) preventing or delaying the appearance of clinical symptoms of the state, disorder or condition developing in a human or other mammal that may be afflicted with or predisposed to the state, disorder or condition but does not yet experience or display clinical or subclinical symptoms of the state, disorder or condition; (2) inhibiting the state, disorder or condition, i.e., arresting, reducing or delaying the development of the disease or a relapse thereof (in case of maintenance treatment) or at least one clinical or subclinical symptom thereof; or (3) relieving the disease, i.e., causing regression of the state, disorder or condition or at least one of its clinical or subclinical symptoms. The benefit to an individual to be treated is either statistically significant or at least perceptible to the patient or to the physician.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Where any amino acid sequence is specifically referred to by a Swiss Prot. or GENBANK Accession number, the sequence is incorporated herein by reference. Information associated with the accession number, such as identification of signal peptide, extracellular domain, transmembrane domain, promoter sequence and translation start, is also incorporated herein in its entirety by reference.

CRISPR Nuclease Compositions

The application of Cas9 technology in eradicating HIV-1 reservoir, particularly targeting LTR, has been shown to be a promising strategy for treating and possibly curing AIDS. Hu, et al., *PNAS* 2014, 111:114616, disclosed that stable transfection of human cell cultures with plasmids expressing Cas9/gRNAs targeted to sites in the HIV-1 LTR successfully eradicated part and/or the entire HIV-1 genome without compromising host cell function. The targeted sites were termed LTR-A. LTR-B, LTR-C, and LTR-D. The targeting of two different sites in the LTR was particularly effective at producing the deletions sufficiently extensive to constitute the excision of all or substantially all of the proviral DNA sequence. The pre-existence of Cas9/gRNAs in cells also prevented new HIV-1 infection.

HIV and other retroviruses are highly mutable, so there is a need for a broader spectrum of Cas9/gRNA reagents and methods for targeting the integrated HIV genome. Of particular use would be Cas9/gRNA reagents that effectively target the structural genes of HIV, such as gag and pol.

Accordingly, embodiments of the invention are directed to compositions and methods for the treatment and eradication of highly mutable and/or latent viruses from a host cell in vitro or in vivo. Methods of the invention may be used to remove viral or other foreign genetic material from a host organism, without interfering with the integrity of the host's genetic material. A nuclease may be used to target viral nucleic acid, thereby interfering with viral replication or transcription or even excising the viral genetic material from the host genome. The nuclease may be specifically targeted to remove only the viral nucleic acid without acting on host material either when the viral nucleic acid exists as a particle within the cell or when it is integrated into the host genome. Targeting the viral nucleic acid can be done using a sequence-specific moiety such as a guide RNA that targets viral genomic material for destruction by the nuclease and does not target the host cell genome. In some embodiments, a CRISPR/Cas nuclease and guide RNA (gRNA) that together target and selectively edit or destroy viral genomic material is used. The CRISPR (clustered regularly interspaced short palindromic repeats) is a naturally-occurring element of the bacterial immune system that protects bacteria from phage infection. The guide RNA localizes the CRISPR/Cas complex to a viral target sequence. Binding of the complex localizes the Cas endonuclease to the viral genomic target sequence causing breaks in the viral genome. Other nuclease systems can be used including, for example, zinc finger nucleases, transcription activator-like effector nucleases (TALENs), meganucleases, or any other system that can be used to degrade or interfere with viral nucleic acid without interfering with the regular function of the host's genetic material.

The compositions embodied herein, can be used to target viral nucleic acid in any form or at any stage in the viral life cycle. The targeted viral nucleic acid may be present in the host cell as independent particles. In a preferred embodiment, the viral infection is latent and the viral nucleic acid is integrated into the host genome. Any suitable viral nucleic acid may be targeted for cleavage and digestion.

Figures 1A, 1B, 1C, 1D:
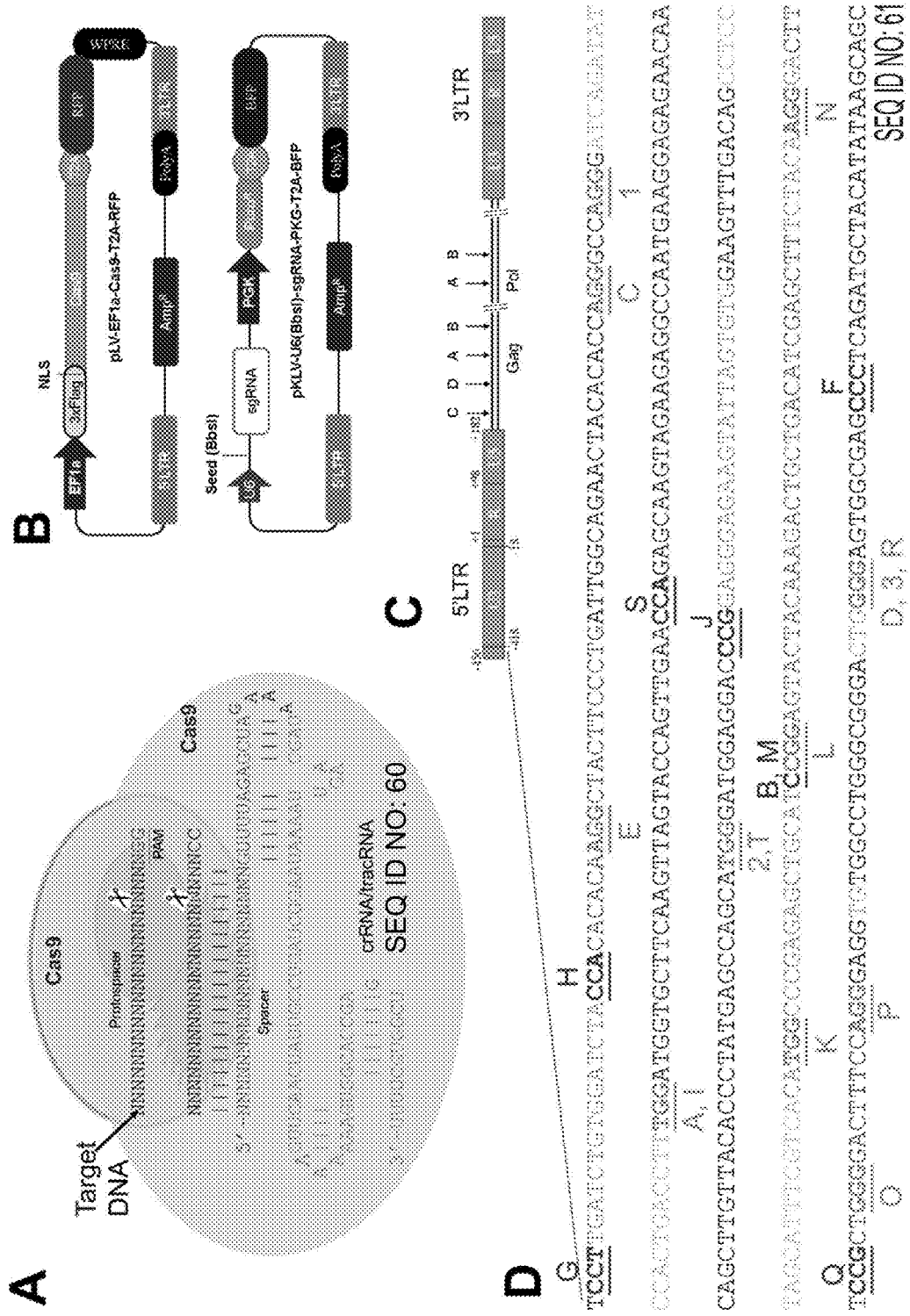
FIG. 1A shows a diagram of *Streptococcus pyogenes* Cas9 (SpCas9), single guide RNA (sgRNA) and protospacer adjacent motif (PAM), showing the cutting site at the third nucleotide of both strand DNA from the PAM NGG or NAG and sequence of sgRNA. The sgRNA is composed of the CRISPR RNA (crRNA) containing 20 bp spacer (seed or target sequence) and 12 bp, the stem loop (GAAA) and the trasactivation cRNA (tracRNA) (SEQ ID NO: 60)
FIG. 1B shows a map diagram for spCas9 expressing lentiviral vector (top) and sgRNA expressing lentiviral vector (bottom). The lentiviral reporter vector (top) was purchased from Biosettia, expressing 3×Flag for immunodetection, reporter red fluorescent protein (RFP) for easy tittering and FACS analysis, and T2A peptide for self-cleavage to prevent the potential effect of RFP on Cas9 function. The sgRNA expressing lentiviral vector was modified from Addgene vector (#50946) showing BbsI cloning site and antibiotic selection marker Puromycin and reporter blue fluorescent protein (BFP) for easy tittering and FACS analysis.
FIG. 1C shows a diagram of the HIV-1 genome, showing selected gRNAs targeting HIV-1 LTR, Gag (A-D) and Pol (A, B) regions.
FIG. 1D shows a detailed diagram of sgRNAs targeting 400 bp within U3 region of HIV-1 LTR (SEQ ID NO: 61). The seed sequences with green PAM (underlined bold) at the sense strand, and red PAM (underlined bold) at the antisense strand, were labeled as indicated. Most of them can be also paired for Cas9 nickase and RNA-guided FokI nuclease (RFN), which can reduce up to 1500-fold potential off-target effects. Selection of the 400 bp region was based on its absence in all the currently-used lentiviral vectors that are used for the gene and sgRNA delivery. Such selection will prevent the self-cleavage of the lentiviral vectors by the Cas9/gRNA.
Figure 1E:
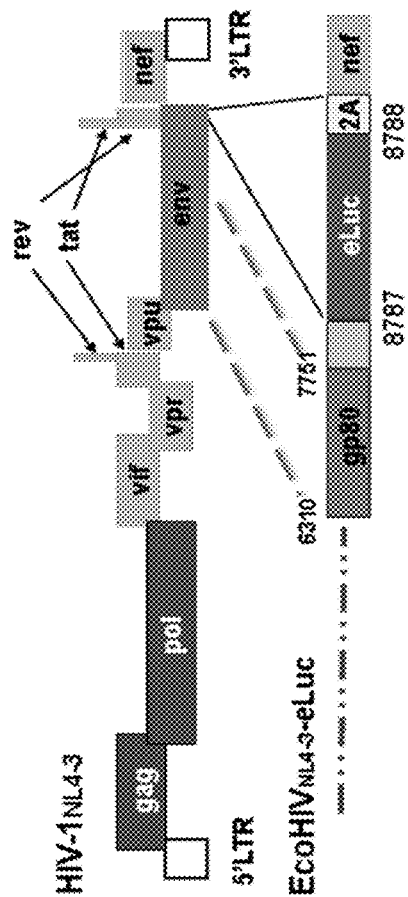
FIG. 1E shows a diagram of EcoHIV reporter vector containing enhanced firefly luciferase (eLuc) derived from human HIV-1$_{NL4-3}$ vector. The eLuc gene was inserted between Env and Nef with a self-cleaving 2A peptide before Nef, while the gp120 of HIV-1 was replaced with gp80 from the ecotropic murine leukemia virus.

CRISPR/Cas Systems: The CRISPR-Cas system includes a gene editing complex comprising a CRISPR-associated nuclease, e.g., Cas9, and a guide RNA complementary to a target sequence situated on a DNA strand, such as a target sequence in proviral DNA integrated into a mammalian genome. An exemplary gene editing complex is shown in FIG. 1A. The gene editing complex can cleave the DNA within the target sequence. This cleavage can in turn cause the introduction of various mutations into the proviral DNA, resulting in inactivation of HIV provirus. The mechanism by which such mutations inactivate the provirus can vary. For example, the mutation can affect proviral replication, and viral gene expression. The mutations may be located in regulatory sequences or structural gene sequences and result in defective production of HIV. The mutation can comprise a deletion. The size of the deletion can vary from a single nucleotide base pair to about 10,000 base pairs. In some embodiments, the deletion can include all or substantially all of the integrated retroviral nucleic acid sequence. In some embodiments the deletion can include the entire integrated retroviral nucleic acid sequence. The mutation can comprise an insertion, that is, the addition of one or more nucleotide base pairs to the pro-viral sequence. The size of the inserted sequence also may vary, for example from about one base pair to about 300 nucleotide base pairs. The mutation can comprise a point mutation, that is, the replacement of a single nucleotide with another nucleotide. Useful point mutations are those that have functional consequences, for example, mutations that result in the conversion of an amino acid codon into a termination codon or that result in the production of a nonfunctional protein.

In general, CRISPR/Cas proteins comprise at least one RNA recognition and/or RNA binding domain. RNA recognition and/or RNA binding domains interact with guide RNAs. CRISPR/Cas proteins can also comprise nuclease domains (i.e., DNase or RNase domains), DNA binding domains, helicase domains, RNase domains, protein-protein interaction domains, dimerization domains, as well as other domains.

In embodiments, the CRISPR/Cas-like protein can be a wild type CRISPR/Cas protein, a modified CRISPR/Cas protein, or a fragment of a wild type or modified CRISPR/Cas protein. The CRISPR/Cas-like protein can be modified to increase nucleic acid binding affinity and/or specificity, alter an enzymatic activity, and/or change another property of the protein. For example, nuclease (i.e., DNase, RNase) domains of the CRISPR/Cas-like protein can be modified, deleted, or inactivated. Alternatively, the CRISPR/Cas-like protein can be truncated to remove domains that are not essential for the function of the fusion protein. The CRISPR/Cas-like protein can also be truncated or modified to optimize the activity of the effector domain of the fusion protein.

In embodiments, the CRISPR/Cas system can be a type I, a type II, or a type III system. Non-limiting examples of suitable CRISPR/Cas proteins include Cas3, Cas4, Cas5, Cas5e (or CasD), Cash, Cas6e, Cas6f, Cas7, Cas8a1, Cas8a2, Cas8b, Cas8c, Cas9, Cas10, Cas10d, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, and Cu1966.

In one embodiment, the RNA-guided endonuclease is derived from a type II CRISPR/Cas system. In other embodiments, the RNA-guided endonuclease is derived from a Cas9 protein. The Cas9 protein can be from *Streptococcus pyogenes, Streptococcus thermophilus, Streptococcus* sp., *Nocardiopsis dassonvillei, Streptomyces pristinaespiralis, Streptomyces viridochromogenes, Streptomyces viridochromogenes, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales* bacterium, *Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus,* or *Acaryochloris marina.*

In some embodiments, the CRISPR/Cas-like protein can be derived from a wild type Cas9 protein or fragment thereof. In other embodiments, the CRISPR/Cas-like protein can be derived from modified Cas9 protein. For example, the amino acid sequence of the Cas9 protein can be modified to alter one or more properties (e.g., nuclease activity, affinity, stability, etc.) of the protein. Alternatively, domains of the Cas9 protein not involved in RNA-guided cleavage can be eliminated from the protein such that the modified Cas9 protein is smaller than the wild type Cas9 protein.

An exemplary and preferred CRISPR-associated endonuclease is a Cas9 nuclease. The Cas9 nuclease can have a nucleotide sequence identical to the wild type *Streptococcus pyrogenes* sequence. In some embodiments, the CRISPR-associated endonuclease can be a sequence from other species, for example other *Streptococcus* species, such as *thermophilus; Pseudomonas aeruginosa, Escherichia coli*, or other sequenced bacteria genomes and archaea, or other prokaryotic microorganisms. Alternatively, the wild type *Streptococcus* pyrogenes Cas9 sequence can be modified. The nucleic acid sequence can be codon optimized for efficient expression in mammalian cells, i.e., "humanized." A humanized Cas9 nuclease sequence can be for example, the Cas9 nuclease sequence encoded by any of the expression vectors listed in Genbank accession numbers KM099231.1 GI:669193757; KM099232.1 GI:669193761; or KM099233.1 GI:669193765. Alternatively, the Cas9 nuclease sequence can be for example, the sequence contained within a commercially available vector such as PX330 or PX260 from Addgene (Cambridge, MA). In some embodiments, the Cas9 endonuclease can have an amino acid sequence that is a variant or a fragment of any of the Cas9 endonuclease sequences of Genbank accession numbers KM099231.1 GI:669193757; KM099232.1 GI:669193761; or KM099233.1 GI:669193765 or Cas9 amino acid sequence of PX330 or PX260 (Addgene, Cambridge, MA). The Cas9 nucleotide sequence can be modified to encode biologically active variants of Cas9, and these variants can have or can include, for example, an amino acid sequence that differs from a wild type Cas9 by virtue of containing one or more mutations (e.g., an addition, deletion, or substitution mutation or a combination of such mutations). One or more of the substitution mutations can be a substitution (e.g., a conservative amino acid substitution). For example, a biologically active variant of a Cas9 polypeptide can have an amino acid sequence with at least or about 50% sequence identity (e.g., at least or about 50%, 55%, 60%, 65%, 70%, 75%, 80%, 85%, 90%, 95%, 97%, 98%, or 99% sequence identity) to a wild type Cas9 polypeptide. Conservative amino acid substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine. The amino acid residues in the Cas9 amino acid sequence can be non-naturally occurring amino acid residues. Naturally occurring amino acid residues include those naturally encoded by the genetic code as well as non-standard amino acids (e.g., amino acids having the D-configuration instead of the L-configuration). The present peptides can also include amino acid residues that are modified versions of standard residues (e.g. pyrrolysine can be used in place of lysine and selenocysteine can be used in place of cysteine). Non-naturally occurring amino acid residues are those that have not been found in nature, but that conform to the basic formula of an amino acid and can be incorporated into a peptide. These include D-alloisoleucine(2R,3S)-2-amino-3-methylpentanoic acid and L-cyclopentyl glycine (S)-2-amino-2-cyclopentyl acetic acid. For other examples, one can consult textbooks or the worldwide web (a site currently maintained by the California Institute of Technology displays structures of non-natural amino acids that have been successfully incorporated into functional proteins).

The Cas9 nuclease sequence can be a mutated sequence. For example, the Cas9 nuclease can be mutated in the conserved HNH and RuvC domains, which are involved in strand specific cleavage. For example, an aspartate-to-alanine (D10A) mutation in the RuvC catalytic domain allows the Cas9 nickase mutant (Cas9n) to nick rather than cleave DNA to yield single-stranded breaks, and the subsequent preferential repair through HDR can potentially decrease the frequency of unwanted indel mutations from off-target double-stranded breaks.

The present invention incorporates several advances over the Cas9/gRNA system disclosed in Hu, et al, *PNAS* 2014, 111:114616. In experiments disclosed in the Examples, additional highly specific target sequences were identified both within the HIV-1 LTR and within the structural genes of HIV-1. These target sequences (also referred to as target "sites"), were efficiently edited by Cas9/gRNA, causing inactivation of viral gene expression and replication in latently-infected mammalian cells. Certain of these additional Cas9/gRNA constructs, and combinations thereof, were found to cause excision of all or part of integrated HIV proviral DNA from the host cell genome. Pairs of constructs with one member directed toward an LTR target site, and the other member toward a structural gene target site, were particularly effective at producing excision or eradication of the HIV genome. This is the first demonstration that a combined attack on an LTR site and structural gene can produce excision of the intervening stretch of integrated HIV DNA. The present invention thus greatly broadens the spectrum of Cas9/gRNA compositions that are available to target integrated HIV DNA in host cells.

Accordingly, the invention features compositions for use in inactivating a proviral DNA integrated into a host cell, including an isolated nucleic acid sequence encoding a CRISPR-associated endonuclease and one or more isolated nucleic acid sequences encoding one or more gRNAs complementary to a target sequence in HIV or another retrovirus.

A gRNA includes a mature crRNA that contains about 20 base pairs (bp) of unique target sequence (called spacer) and a trans-activated small RNA (tracrRNA) that serves as a guide for ribonuclease III-aided processing of pre-crRNA. The crRNA:tracrRNA duplex directs Cas9 to target DNA via complementary base pairing between the spacer on the crRNA and the complementary sequence (called protospacer) on the target DNA. Cas9 recognizes a trinucleotide (NGG) protospacer adjacent motif (PAM) to specify the cut site (the 3rd nucleotide from PAM). In the present invention, the crRNA and tracrRNA can be expressed separately or engineered into an artificial fusion gRNA via a synthetic stem loop (AGAAAU) to mimic the natural crRNA/tracrRNA duplex. Such gRNA can be synthesized or in vitro transcribed for direct RNA transfection or expressed from U6 or H1-promoted RNA expression vector.

In the compositions of the present invention, each gRNA includes a sequence that is complementary to a target sequence in a retrovirus. The exemplary target retrovirus is HIV, but the compositions of the present invention are also useful for targeting other retroviruses, such as HIV-2 and simian immunodeficiency virus (SIV)-1.

Some of the exemplary gRNAs of the present invention are complimentary to target sequences in the long terminal repeat (LTR) regions of HIV. The LTRs are subdivided into U3, R and U5 regions. The configuration of the U1, R, U5 regions of HIV-1 is shown in FIG. 3A. LTRs contain all of the required signals for gene expression, and are involved in the integration of a provirus into the genome of a host cell. For example, the basal or core promoter, a core enhancer and a modulatory region is found within U3 while the transactivation response element is found within R. In HIV-1, the U5 region includes several sub-regions, for example, TAR or trans-acting responsive element, which is involved in transcriptional activation; Poly A, which is involved in dimerization and genome packaging; PBS or primer binding site; Psi or the packaging signal; DIS or dimer initiation site. Accordingly, in some embodiments a gRNA target sequence comprises one or more target sequences in an LTR region of an HIV proviral DNA and one or more targets in a structural gene and/or non-structural gene of the HIV proviral DNA. In other embodiments, a gRNA target sequence comprises one or more target sequences in an LTR region of an HIV proviral DNA and one or more targets in a structural gene. In another embodiment, a gRNA target sequence comprises one or more target sequences in an LTR region of an HIV proviral DNA and one or more targets in a non-structural gene of the HIV proviral DNA. In yet another embodiment, a gRNA target sequence comprises one or more target sequences in an HIV proviral a structural gene and one or more targets in a non-structural gene of the HIV proviral DNA. In yet another embodiment, a gRNA target sequence comprises one or more target sequences in an HIV proviral a non-coding gene and one or more targets in a coding gene of the HIV proviral DNA. In yet another embodiment a gRNA target nucleic acid sequence comprises one or more target nucleic acid sequences in a first gene and one or more target nucleic acid sequences in a second gene; or, one or more target nucleic acid sequences in a first gene and one or more target nucleic acid sequences in a third gene; or, one or more target nucleic acid sequences in a first gene and one or more target nucleic acid sequences in a second gene and one or more target nucleic acid sequences in a third gene; or, one or more target nucleic acid sequences in a second gene and one or more target nucleic acid sequences in a third gene or fourth gene; or, any combinations thereof. As can be seen, any combination of target nucleic acid sequences can be used and are only limited by the imagination of one of ordinary skill in the art.

In experimental results disclosed in the Examples certain sequences within the U3, R, and U5 regions of the LTR were found to be useful target sequences. The gRNAs complementary to these target sequences are indicated in FIGS. 1D and 3A of Example 2, FIG. 11A of Example 3 and Table 1 of Example 4. They include LTR 1, LTR 2, LTR 3, LTR A, LTR B, LTR B', LTR C, LTR D, LTR E, LTR F, LTR G, LTR H, LTR I, LTR J, LTR K, LTR L, LTR M, LTR N, LTR O, LTR P, LTR Q, LTR R, LTR S, AND LTR T. The sequences of these gRNAs are shown in FIGS. 11A, 12A, 12B and 12C. The compositions of the present invention include these exemplary gRNAs, but are not limited to them, and can include gRNAs complimentary to any suitable target site in the HIV LTRs.

Some of the exemplary gRNAs of the present invention target sequences in the protein coding genome of HIV. Sequences within the gene encoding the structural protein gag were found to be useful target sequences. gRNAs complementary to these target sequences include Gag A, Gag B, Gag C, and Gag D. Their target sites in the HIV-1 genome are indicated in FIG. 3A, and their nucleic acid sequences are shown in Table 1. Useful target sequences were also found within the gene encoding the structural protein pol. gRNAs complementary to these target sequences include Pol A and Pol B. Their target sites in the HIV-1 genome are indicated in FIG. 3A, and their nucleic acid sequences are shown in Table 1. Sequences for gRNAs complementary to target sites in the HIV-1 envelope protein env are also shown in Table 1.

Accordingly, the compositions of the present invention include these exemplary gRNAs, but are not limited to them, and can include gRNAs complimentary to any suitable target site in the protein coding genes of HIV, including but not limited to those encoding the structural protein tat, and the accessory proteins vif, nef (negative factor) vpu (Virus protein U), vpr, and tev.

Guide RNA sequences according to the present invention can be sense or anti-sense sequences. The guide RNA sequence generally includes a proto-spacer adjacent motif (PAM). The sequence of the PAM can vary depending upon the specificity requirements of the CRISPR endonuclease used. In the CRISPR-Cas system derived from *S. pyogenes*, the target DNA typically immediately precedes a 5'-NGG proto-spacer adjacent motif (PAM). Thus, for the *S. pyogenes* Cas9, the PAM sequence can be AGG, TGG, CGG or GGG. Other Cas9 orthologs may have different PAM specificities. For example, Cas9 from *S. thermophilus* requires 5'-NNAGAA for CRISPR 1 and 5'-NGGNG for CRISPR3) and *Neiseria menigiditis* requires 5'-NNNNGATT). The specific sequence of the guide RNA may vary, but, regardless of the sequence, useful guide RNA sequences will be those that minimize off-target effects while achieving high efficiency and complete ablation of the genomically integrated retrovirus, e.g. HIV. The length of the guide RNA sequence can vary from about 20 to about 60 or more nucleotides, for example about 20, about 21, about 22, about 23, about 24, about 25, about 26, about 27, about 28, about 29, about 30, about 31, about 32, about 33, about 34, about 35, about 36, about 37, about 38, about 39, about 40, about 45, about 50, about 55, about 60 or more nucleotides. Useful selection methods identify regions having extremely low homology between the foreign viral genome and host cellular genome including endogenous retroviral DNA, include bioinformatic screening using 12-bp+NGG target-selection criteria to exclude off-target human transcriptome or (even rarely) untranslated-genomic sites; avoiding transcription factor binding sites within the HIV LTR promoter (potentially conserved in the host genome); and WGS, Sanger sequencing and SURVEYOR assay, to identify and exclude potential off-target effects.

The guide RNA sequence can be configured as a single sequence or as a combination of one or more different sequences, e.g., a multiplex configuration. Multiplex configurations can include combinations of two, three, four, five, six, seven, eight, nine, ten, or more different guide RNAs.

In experiments disclosed in Examples 2 and 3, combinations of gRNAs were found to be especially effective when expressed in multiplex fashion, that is, simultaneously in the same cell. In many cases, the combinations produced excision of the HIV provirus extending between the target sites. The excisions are attributable to deletions of sequences between the cleavages induced by Cas9 at each of the multiple target sites. These combinations pairs of gRNAs, with one member being complementary to a target site in an LTR of the retrovirus, and the other member being complementary to a gRNA complementary to a target site in a structural gene of the retrovirus. Exemplary effective combinations include Gag D combined with one of LTR 1, LTR 2, LTR 3, LTR A, LTR B, LTR C, LTR D, LTR E, LTR F, LTR G; LTR H, LTR I, LTR J, LTR K, LTR L, LTR M; LTR N, LTR O, LTR P, LTR Q, LTR R, LTR S, or LTR T. Exemplary effective combinations also include LTR 3 combined with one of LTR-1, Gag A; Gag B; Gag C, Gag D, Pol A, or Pol B.

Combinations of LTR A and LTR B' also caused excision of segments of the HIV-1 genome, as shown in Example 3. The compositions of present invention are not limited to these combinations, but include any suitable combination of gRNAs complimentary to two or more different target sites in the HIV-1 provirus.

In certain embodiments, a target nucleic acid sequence comprises one or more nucleic acid sequences in coding and non-coding nucleic acid sequences of the retroviral genome. The target nucleic acid sequence can be located within a sequence encoding structural proteins, non-structural proteins or combinations thereof. The sequences encoding structural proteins comprise nucleic acid sequences encoding: Gag, Gag-Pol precursor, Pro (protease), Reverse Transcriptase (RT), integrase (In), Env or combinations thereof. The sequences encoding non-structural proteins comprise nucleic acid sequences encoding: regulatory proteins e.g. Tat, Rev, accessory proteins, e.g. Nef, Vpr, Vpu, Vif or combinations thereof.

In certain embodiments, a gRNA sequence has at least a 75% sequence identity to complementary target nucleic acid sequences encoding Gag, Gag-Pol precursor, Pro, Reverse Transcriptase (RT), integrase (In), Env. Tat, Rev, Nef, Vpr, Vpu, Vif or combinations thereof.

In certain embodiments, a gRNA sequence is complementary to target nucleic acid sequences encoding Gag, Gag-Pol precursor, Pro, Reverse Transcriptase (RT), integrase (In), Env. Tat, Rev, Nef, Vpr, Vpu, Vif or combinations thereof.

In other embodiments, the gRNA nucleic acid sequences have at least a 75% sequence identity to the sequences comprising: SEQ ID NOS: 1-57, or any combinations thereof. In other embodiments, a gRNA nucleic acid sequence comprises SEQ ID NOS: 1-57.

In another embodiment, a nucleic acid sequence comprises a sequence having at least a 75% sequence identity to the sequences comprising: SEQ ID NOS: 1-57, or any combinations thereof. In other embodiments, a nucleic acid sequence comprises a sequence set forth as SEQ ID NOS: 1-57.

In other embodiments, a composition for use in inactivating retroviral DNA integrated into the genome of a host cell latently infected with a retrovirus, comprises an isolated nucleic acid sequence encoding a Clustered Regularly Interspaced Short Palindromic Repeat (CRISPR)-associated endonuclease and at least one guide RNA (gRNA), the gRNA being complementary to a target sequence in the integrated retroviral DNA, wherein the retrovirus is a human immunodeficiency virus (HIV). The at least one gRNA includes at least a first gRNA that is complementary to a target sequence in the integrated retroviral DNA; and a second gRNA that is complementary to another target sequence in the integrated retroviral DNA, whereby the intervening sequences between the two gRNAs are removed.

In certain embodiments, a target nucleic acid sequence comprises one or more sequences in a long terminal repeat (LTR) region of a human immunodeficiency virus (HIV) proviral DNA and one or more targets in a structural and/or non-structural gene of the HIV integrated DNA; or, one or more targets in a second gene; or, one or more targets in a first gene and one or more targets in a second gene; or, one or more targets in a first gene and one or more targets in a second gene and one or more targets in a third gene; or, one or more targets in a second gene and one or more targets in a third gene or fourth gene; or, any combinations thereof.

In another embodiment, a composition for eradicating a retrovirus in vitro or in vivo, comprises an isolated nucleic acid sequence encoding a Clustered Regularly Interspaced Short Palindromic Repeat (CRISPR)-associated endonuclease and at least one guide RNA (gRNA), the gRNA being complementary to a target sequence in a retroviral genome, wherein the retrovirus is a human immunodeficiency virus (HIV). In embodiments, the at least one gRNA includes at least a first gRNA that is complementary to a target sequence in an HIV genome; and a second gRNA that is complementary to another target sequence in the HIV genome, whereby the intervening sequences between the two gRNAs are removed.

In another embodiment, a composition comprises an isolated nucleic acid sequence encoding a Clustered Regularly Interspaced Short Palindromic Repeat (CRISPR)-associated endonuclease and at least two guide RNAs (gRNAs), the gRNAs each being complementary to different target sequences in a retroviral genome, wherein the retrovirus is a human immunodeficiency virus (HIV). In embodiments, the at least one guide RNAs (gRNAs) includes at least a first gRNA that is complementary to a target sequence in an HIV genome; and a second gRNA that is complementary to another target sequence in the HIV genome, whereby the intervening sequences between the two gRNAs are removed.

In certain embodiments, a target nucleic acid sequence comprises one or more nucleic acid sequences in coding and non-coding nucleic acid sequences of the retroviral genome. The target nucleic acid sequence can be located within a sequence encoding structural proteins, non-structural proteins or combinations thereof. The sequences encoding structural proteins comprise nucleic acid sequences encoding: Gag, Gag-Pol precursor, Pro (protease), Reverse Transcriptase (RT), integrase (In), Env or combinations thereof. The sequences encoding non-structural proteins comprise nucleic acid sequences encoding: regulatory proteins e.g. Tat, Rev, accessory proteins, e.g. Nef, Vpr, Vpu, Vif or combinations thereof.

In certain embodiments, a gRNA sequence has at least a 75% sequence identity to complementary target nucleic acid sequences encoding Gag, Gag-Pol precursor, Pro, Reverse Transcriptase (RT), integrase (In), Env. Tat, Rev, Nef, Vpr, Vpu, Vif or combinations thereof.

In certain embodiments, a gRNA sequence is complementary to target nucleic acid sequences encoding Gag, Gag-Pol precursor, Pro, Reverse Transcriptase (RT), integrase (In), Env. Tat, Rev, Nef, Vpr, Vpu, Vif or combinations thereof.

In other embodiments, the gRNA nucleic acid sequences have at least a 75% sequence identity to the sequences comprising: SEQ ID NOS: 1-57, or any combinations thereof. In other embodiments, a gRNA nucleic acid sequence comprises SEQ ID NOS: 1-57.

Accordingly, the present invention also includes a method of inactivating a proviral DNA integrated into the genome of a host cell latently infected with a retrovirus, the method including the steps of treating the host cell with a composition comprising a CRISPR-associated endonuclease, and at least one gRNA complementary to a target site in the proviral DNA; expressing a gene editing complex including the CRISPR-associated endonuclease and the at least one gRNA; and inactivating the proviral DNA. The previously enumerated gRNAs and Cas9 endonucleases are preferred. In another preferred embodiment, the step of treating the host cell in vitro or in vivo includes treatment with at least two gRNAs, wherein each of the at least two gRNAs are complementary to a different target nucleic acid sequence in the proviral DNA. Especially preferred are combinations of at least two gRNAs, including compositions wherein at least one gRNA is complementary to a target site in an LTR of the retrovirus, and at least one gRNA is complementary to a target site in a structural gene of the retrovirus. HIV is the preferred retrovirus.

In another embodiment, a composition for eradicating a retrovirus in vitro or in vivo, comprises an isolated nucleic acid sequence encoding a Clustered Regularly Interspaced Short Palindromic Repeat (CRISPR)-associated endonuclease and at least one guide RNA (gRNA), the gRNA being complementary to a target sequence in a retroviral genome, wherein the retrovirus is a human immunodeficiency virus (HIV) and the gRNA includes at least a first gRNA that is complementary to a target sequence in an HIV genome; and a second gRNA that is complementary to another target sequence in the HIV genome, whereby the intervening sequences between the two gRNAs are removed. The target nucleic acid sequences comprise one or more nucleic acid sequences in coding and non-coding nucleic acid sequences of the HIV genome. In one embodiment, the target sequences comprise one or more nucleic acid sequences in the HIV genome comprising: long terminal repeat (LTR) nucleic acid sequences, nucleic acid sequences encoding structural proteins, non-structural proteins or combinations thereof. In certain embodiments, nucleic acid sequences encoding structural proteins comprise nucleic acid sequences encoding: Gag, Gag-Pol precursor, Pro (protease), Reverse Transcriptase (RT), integrase (In), Env or combinations thereof. In embodiments, the nucleic acid sequences encoding non-structural proteins comprise nucleic acid sequences encoding: regulatory proteins, accessory proteins or combinations thereof. Examples of regulatory proteins include: Tat, Rev or combinations thereof. Examples of accessory proteins comprise Nef, Vpr, Vpu, Vif or combinations thereof. In certain embodiments, a gRNA nucleic acid sequence comprises a nucleic acid sequence having a sequence identity of at least 75% to SEQ ID NOS: 1-57. In certain embodiments a gRNA nucleic acid sequence comprises a nucleic acid sequence comprising SEQ ID NOS: 1-57.

In certain embodiments, an isolated nucleic acid sequence comprises a nucleic acid sequence encoding a Clustered Regularly Interspaced Short Palindromic Repeat (CRISPR)-associated endonuclease and at least one guide RNA (gRNA), the gRNA being complementary to a target nucleic acid sequence in a retrovirus genome, for example HIV.

When the compositions are administered as a nucleic acid or are contained within an expression vector, the CRISPR endonuclease can be encoded by the same nucleic acid or vector as the guide RNA sequences. Alternatively, or in addition, the CRISPR endonuclease can be encoded in a physically separate nucleic acid from the gRNA sequences or in a separate vector.

Modified or Mutated Nucleic Acid Sequences: In some embodiments, any of the nucleic acid sequences embodied herein may be modified or derived from a native nucleic acid sequence, for example, by introduction of mutations, deletions, substitutions, modification of nucleobases, backbones and the like. The nucleic acid sequences include the vectors, gene-editing agents, gRNAs, tracrRNA etc. Examples of some modified nucleic acid sequences envisioned for this invention include those comprising modified backbones, for example, phosphorothioates, phosphotriesters, methyl phosphonates, short chain alkyl or cycloalkyl intersugar linkages or short chain heteroatomic or heterocyclic intersugar linkages. In some embodiments, modified oligonucleotides comprise those with phosphorothioate backbones and those with heteroatom backbones, $CH_2$—NH—O—$CH_2$, CH, —N($CH_3$)—O—$CH_2$ [known as a methylene(methylimino) or MMI backbone], $CH_2$—O—N($CH_3$)—$CH_2$, $CH_2$—N($CH_3$)—N($CH_3$)—$CH_2$ and O—N($CH_3$)—$CH_2$—$CH_2$ backbones, wherein the native phosphodiester backbone is represented as O—P—O—$CH_2$,). The amide backbones disclosed by De Mesmaeker et al. *Acc. Chem. Res.* 1995, 28:366-374) are also embodied herein. In some embodiments, the nucleic acid sequences having morpholino backbone structures (Summerton and Weller, U.S. Pat. No. 5,034,506), peptide nucleic acid (PNA) backbone wherein the phosphodiester backbone of the oligonucleotide is replaced with a polyamide backbone, the nucleobases being bound directly or indirectly to the aza nitrogen atoms of the polyamide backbone (Nielsen et al. *Science* 1991, 254, 1497). The nucleic acid sequences may also comprise one or more substituted sugar moieties. The nucleic acid sequences may also have sugar mimetics such as cyclobutyls in place of the pentofuranosyl group.

The nucleic acid sequences may also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, $N_6$ (6-aminohexyl)adenine and 2,6-diaminopurine. Kornberg, A., DNA Replication, W. H. Freeman & Co., San Francisco, 1980, pp 75-77; Gebeyehu, G., et al. *Nucl. Acids Res.* 1987, 15:4513). A "universal" base known in the art, e.g., inosine may be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278).

Another modification of the nucleic acid sequences of the invention involves chemically linking to the nucleic acid sequences one or more moieties or conjugates which enhance the activity or cellular uptake of the oligonucleotide. Such moieties include but are not limited to lipid moieties such as a cholesterol moiety, a cholesteryl moiety (Letsinger et al., *Proc. Natl. Acad. Sci. USA* 1989, 86, 6553), cholic acid (Manoharan et al. *Bioorg. Med. Chem. Let.* 1994, 4, 1053), a thioether, e.g., hexyl-S-tritylthiol (Manoharan et al. *Ann. N.Y. Acad. Sci.* 1992, 660, 306; Manoharan et al. *Bioorg. Med. Chem. Let.* 1993, 3, 2765), a thiocholesterol (Oberhauser et al., *Nucl. Acids Res.* 1992, 20, 533), an aliphatic chain, e.g., dodecandiol or undecyl residues (Saison-Behmoaras et al. *EMBO J.* 1991, 10, 111; Kabanov et al. *FEBS Lett.* 1990, 259, 327; Svinarchuk et al. *Biochimie* 1993, 75, 49), a phospholipid, e.g., di-hexadecyl-rac-glycerol or triethylammonium 1,2-di-O-hexadecyl-rac-glycero-3-H-phosphonate (Manoharan et al. *Tetrahedron Lett.* 1995, 36, 3651; Shea et al. *Nucl. Acids Res.* 1990, 18, 3777), a polyamine or a polyethylene glycol chain (Manoharan et al. *Nucleosides & Nucleotides* 1995, 14, 969), or adamantane acetic acid (Manoharan et al. *Tetrahedron Lett.* 1995, 36, 3651).

It is not necessary for all positions in a given nucleic acid sequence to be uniformly modified, and in fact more than one of the aforementioned modifications may be incorporated in a single nucleic acid sequence or even at within a single nucleoside within a nucleic acid sequence.

In some embodiments, the RNA molecules e.g. crRNA, tracrRNA, gRNA are engineered to comprise one or more modified nucleobases. For example, known modifications of RNA molecules can be found, for example, in Genes VI, Chapter 9 ("Interpreting the Genetic Code"), Lewis, ed. (1997, Oxford University Press, New York), and Modification and Editing of RNA, Grosjean and Benne, eds. (1998, ASM Press, Washington DC). Modified RNA components include the following: 2'-O-methylcytidine; $N^4$-methylcytidine; $N^4$-2'-O-dimethylcytidine; $N^4$-acetylcytidine; 5-methylcytidine; 5,2'-O-dimethylcytidine; 5-hydroxymethylcytidine; 5-formylcytidine; 2'-O-methyl-5-formaylcytidine; 3-methylcytidine; 2-thiocytidine; lysidine; 2'-O-methyluridine; 2-thiouridine; 2-thio-2'-O-methyluridine; 3,2'-O-dimethyluridine; 3-(3-amino-3-carboxypropyl)uridine; 4-thiouridine; ribosylthymine; 5,2'-O-dimethyluridine; 5-methyl-2-thiouridine; 5-hydroxyuridine; 5-methoxyuridine; uridine 5-oxyacetic acid; uridine 5-oxyacetic acid methyl ester; 5-carboxymethyluridine; 5-methoxycarbonylmethyluridine; 5-methoxycarbonylmethyl-2'-O-methyluridine; 5-methoxycarbonylmethyl-2'-thiouridine; 5-carbamoylmethyluridine; 5-carbamoylmethyl-2'-O-methyluridine; 5-(carboxyhydroxymethyl)uridine; 5-(carboxyhydroxymethyl) uridinemethyl ester; 5-aminomethyl-2-thiouridine; 5-methylaminomethyluridine; 5-methylaminomethyl-2-thiouridine; 5-methylaminomethyl-2-selenouridine; 5-carboxymethylaminomethyluridine; 5-carboxymethylaminomethyl-2'-O-methyl-uridine; 5-carboxymethylaminomethyl-2-thiouridine; dihydrouridine; dihydroribosylthymine; 2'-methyladenosine; 2-methyladenosine; $N^6$Nmethyladenosine; $N^6$, $N^6$-dimethyladenosine; $N^6$,2'-O-trimethyladenosine; 2 methylthio-$N^6$Nisopentenyl adenosine; $N^6$-(cis-hydroxyisopentenyl)-adenosine; 2-methylthio-$N^6$-(cis-hydroxyisopentenyl)-adenosine; $N^6$-glycinylcarbamoyl)adenosine; $N^6$ threonylcarbamoyl adenosine; $N^6$-methyl-$N^6$-threonylcarbamoyl adenosine; 2-methylthio-$N^6$-methyl-$N^6$-threonylcarbamoyl adenosine; $N^6$-hydroxynorvalylcarbamoyl adenosine; 2-methylthio-$N^6$-hydroxnorvalylcarbamoyl adenosine; 2'-O-ribosyladenosine (phosphate); inosine; 2'O-methyl inosine; 1-methyl inosine; 1;2'-O-dimethyl inosine; 2'-O-methyl guanosine; 1-methyl guanosine; $N^2$-methyl guanosine; $N^2$, $N^2$-dimethyl guanosine; $N^2$, 2'-O-dimethyl guanosine; $N^2$, $N^2$, 2'-O-trimethyl guanosine; 2'-O-ribosyl guanosine (phosphate); 7-methyl guanosine; $N^2$;7-dimethyl guanosine; $N^2$; $N^2$;7-trimethyl guanosine; wyosine; methylwyosine; under-modified hydroxywybutosine; wybutosine; hydroxywybutosine; peroxywybutosine; queuosine; epoxyqueuosine; galactosyl-queuosine; mannosyl-queuosine; 7-cyano-7-deazaguanosine; arachaeosine [also called 7-formamido-7-deazaguanosine]; and 7-aminomethyl-7-deazaguanosine.

The isolated nucleic acid molecules of the present invention can be produced by standard techniques. For example, polymerase chain reaction (PCR) techniques can be used to obtain an isolated nucleic acid containing a nucleotide sequence described herein. Various PCR methods are described in, for example, *PCR Primer: A Laboratory Manual*, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid.

Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >50-100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector.

The present invention also includes a pharmaceutical composition for the inactivation of integrated proviral HIV DNA in a mammalian subject. The composition includes an isolated nucleic acid sequence encoding a Cas endonuclease, and at least one isolated nucleic acid sequence encoding at least one gRNA complementary to a target sequence in a proviral HIV DNA; the isolated nucleic acid sequences being included in at least one expression vector. In the preferred embodiment, the pharmaceutical composition includes a first gRNA and a second gRNA, with the first gRNA targeting a site in the HIV LTR and the second gRNA targeting a site in an HIV structural gene, as previously described.

Exemplary expression vectors for inclusion in the pharmaceutical composition include plasmid vectors and lentiviral vectors, but the present invention is not limited to these vectors. A wide variety of host/expression vector combinations may be used to express the nucleic acid sequences described herein. Suitable expression vectors include, without limitation, plasmids and viral vectors derived from, for example, bacteriophage, baculoviruses, and retroviruses. Numerous vectors and expression systems are commercially available from such corporations as Novagen (Madison, WI), Clontech (Palo Alto, CA), Stratagene (La Jolla, CA), and Invitrogen/Life Technologies (Carlsbad, CA). A marker gene can confer a selectable phenotype on a host cell. For example, a marker can confer biocide resistance, such as resistance to an antibiotic (e.g., kanamycin, G418, bleomycin, or hygromycin). An expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin, or FLAG™ tag (Kodak, New Haven, CT) sequences typically are expressed as a fusion with the encoded polypeptide. Such tags can be inserted anywhere within the polypeptide, including at either the carboxyl or amino terminus.

The vector can also include a regulatory region. The term "regulatory region" refers to nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, nuclear localization signals, and introns.

If desired, the polynucleotides of the invention may also be used with a microdelivery vehicle such as cationic liposomes and adenoviral vectors. For a review of the procedures for liposome preparation, targeting and delivery of contents, see Mannino and Gould-Fogerite, *BioTechniques,* 6:682 (1988). See also, Felgner and Holm, *Bethesda Res. Lab. Focus,* 11(2):21 (1989) and Maurer, R. A., *Bethesda Res. Lab. Focus,* 11(2):25 (1989).

The compositions of the present invention cause the suppression of activation of proviral HIV-1, or the partial or total excision of integrated HIV-1 (Examples 2 and 3), the present invention provides a method of treating a mammalian subject infected with a retrovirus, e.g. HIV. The method includes the steps of determining that a mammalian subject is infected with a retrovirus, administering an effective amount of the previously described pharmaceutical composition, and treating the mammalian subject for the retrovirus infection.

The method represents a solution to the problem of integrated provirus, a solution which is essential to the treatment and prevention of AIDS and other retroviral diseases. During the acute phase of HIV infection, the HIV viral particles enter cells expressing the appropriate CD4 receptor molecules. Once the virus has entered the host cell, the HIV encoded reverse transcriptase generates a proviral DNA copy of the HIV RNA and the proviral DNA becomes integrated into the host cell genomic DNA. It is this HIV provirus that is replicated by the host cell, resulting in the release of new HIV virions which can then infect other cells.

The primary HIV infection subsides within a few weeks to a few months, and is typically followed by a long clinical "latent" period which may last for up to 10 years. During this latent period, there can be no clinical symptoms or detectable viral replication in peripheral blood mononuclear cells and little or no culturable virus in peripheral blood. However, the HIV virus continues to reproduce at very low levels. In subjects who have treated with anti-retroviral therapies, this latent period may extend for several decades or more. Anti-retroviral therapy does not suppress low levels of viral genome expression, nor does it efficiently target latently infected cells such as resting memory T cells, brain macrophages, microglia, astrocytes and gut associated lymphoid cells. Because the compositions of the present invention can inactivate or excise HIV provirus, the methods of treatment employing the compositions constitute a new avenue of attack against HIV infection The compositions of the present invention, when stably expressed in potential host cells, reduce or prevent new infection by retroviruses, e.g. HIV-1 (Example 3). Accordingly, the present invention also provides a method of treatment to reduce the risk of a retrovirus infection, e.g. HIV infection in a mammalian subject at risk for infection. The method includes the steps of determining that a mammalian subject is at risk of HIV infection, administering an effective amount of the previously described pharmaceutical composition, and reducing the risk of HIV infection in the mammalian subject. Preferably, the pharmaceutical composition includes a vector that provides stable and/or inducible expression of at least one of the previously enumerated.

Pharmaceutical compositions according to the present invention can be prepared in a variety of ways known to one of ordinary skill in the art. For example, the nucleic acids and vectors described above can be formulated in compositions for application to cells in tissue culture or for administration to a patient or subject. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids, powders, and the like. Conventional pharmaceutical carriers, aqueous, powder or oily bases, thickeners and the like may be necessary or desirable.

This invention also includes pharmaceutical compositions which contain, as the active ingredient, nucleic acids and vectors described herein, in combination with one or more pharmaceutically acceptable carriers. As used herein, the terms "pharmaceutically acceptable" (or "pharmacologically acceptable") to refer to molecular entities and compositions that do not produce an adverse, allergic or other untoward reaction when administered to an animal or a human, as appropriate. The term "pharmaceutically acceptable carrier," as used herein, includes any and all solvents, dispersion media, coatings, antibacterial, isotonic and absorption delaying agents, buffers, excipients, binders, lubricants, gels, surfactants and the like, that may be used as media for a pharmaceutically acceptable substance. In making the compositions of the invention, the active ingredient is typically mixed with an excipient, diluted by an excipient or enclosed within such a carrier in the form of, for example, a capsule, tablet, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), lotions, creams, ointments, gels, soft and hard gelatin capsules, suppositories, sterile injectable solutions, and sterile packaged powders. As is known in the art, the type of diluent can vary depending upon the intended route of administration. The resulting compositions can include additional agents, such as preservatives. In some embodiments, the carrier can be, or can include, a lipid-based or polymer-based colloid. In some embodiments, the carrier material can be a colloid formulated as a liposome, a hydrogel, a microparticle, a nanoparticle, or a block copolymer micelle. As noted, the carrier material can form a capsule, and that material may be a polymer-based colloid.

The nucleic acid sequences of the invention can be delivered to an appropriate cell of a subject. This can be achieved by, for example, the use of a polymeric, biodegradable microparticle or microcapsule delivery vehicle, sized to optimize phagocytosis by phagocytic cells such as macrophages. For example, PLGA (poly-lacto-co-glycolide) microparticles approximately 1-10 μm in diameter can be used. The polynucleotide is encapsulated in these microparticles, which are taken up by macrophages and gradually biodegraded within the cell, thereby releasing the polynucleotide. Once released, the DNA is expressed within the cell. A second type of microparticle is intended not to be taken up directly by cells, but rather to serve primarily as a slowrelease reservoir of nucleic acid that is taken up by cells only upon release from the micro-particle through biodegradation. These polymeric particles should therefore be large enough to preclude phagocytosis (i.e., larger than 5 μm and preferably larger than 20 μm). Another way to achieve uptake of the nucleic acid is using liposomes, prepared by standard methods. The nucleic acids can be incorporated alone into these delivery vehicles or co-incorporated with tissue-specific antibodies, for example antibodies that target cell types that are common latently infected reservoirs of HIV infection, for example, brain macrophages, microglia, astrocytes, and gut-associated lymphoid cells. Alternatively, one can prepare a molecular complex composed of a plasmid or other vector attached to poly-L-lysine by electrostatic or covalent forces. Poly-L-lysine binds to a ligand that can bind to a receptor on target cells. Delivery of "naked DNA" (i.e., without a delivery vehicle) to an intramuscular, intradermal, or subcutaneous site, is another means to achieve in vivo expression. In the relevant polynucleotides (e.g., expression vectors) the nucleic acid sequence encoding an isolated nucleic acid sequence comprising a sequence encoding a CRISPR-associated endonuclease and a guide RNA is operatively linked to a promoter or enhancer-promoter combination. Promoters and enhancers are described above.

In some embodiments, the compositions of the invention can be formulated as a nanoparticle, for example, nanoparticles comprised of a core of high molecular weight linear polyethylenimine (LPEI) complexed with DNA and surrounded by a shell of polyethyleneglycol-modified (PEGylated) low molecular weight LPEI.

The nucleic acids and vectors may also be applied to a surface of a device (e.g., a catheter) or contained within a pump, patch, or other drug delivery device. The nucleic acids and vectors of the invention can be administered alone, or in a mixture, in the presence of a pharmaceutically acceptable excipient or carrier (e.g., physiological saline). The excipient or carrier is selected on the basis of the mode and route of administration. Suitable pharmaceutical carriers, as well as pharmaceutical necessities for use in pharmaceutical formulations, are described in Remington's Pharmaceutical Sciences (E. W. Martin), a well-known reference text in this field, and in the USP/NF (United States Pharmacopeia and the National Formulary).

In some embodiments, the compositions can be formulated as a nanoparticle encapsulating a nucleic acid encoding Cas9 or a variant Cas9 and at least one gRNA sequence complementary to a target HIV; or it can include a vector encoding these components. Alternatively, the compositions can be formulated as a nanoparticle encapsulating the CRISPR-associated endonuclease the polypeptides encoded by one or more of the nucleic acid compositions of the present invention.

Regardless of whether compositions are administered as nucleic acids or polypeptides, they are formulated in such a way as to promote uptake by the mammalian cell. Useful vector systems and formulations are described above. In some embodiments the vector can deliver the compositions to a specific cell type. The invention is not so limited however, and other methods of DNA delivery such as chemical transfection, using, for example calcium phosphate, DEAE dextran, liposomes, lipoplexes, surfactants, and perfluoro chemical liquids are also contemplated, as are physical delivery methods, such as electroporation, micro injection, ballistic particles, and "gene gun" systems.

In other embodiments, the compositions comprise a cell which has been transformed or transfected with one or more Cas/gRNA vectors. In some embodiments, the methods of the invention can be applied ex vivo. That is, a subject's cells can be removed from the body and treated with the compositions in culture to excise, for example, HIV virus sequences and the treated cells returned to the subject's body. The cell can be the subject's cells or they can be haplotype matched or a cell line. The cells can be irradiated to prevent replication. In some embodiments, the cells are human leukocyte antigen (HLA)-matched, autologous, cell lines, or combinations thereof. In other embodiments the cells can be a stem cell. For example, an embryonic stem cell or an artificial pluripotent stem cell (induced pluripotent stem cell (iPS cell)). Embryonic stem cells (ES cells) and artificial pluripotent stem cells (induced pluripotent stem cell, iPS cells) have been established from many animal species, including humans. These types of pluripotent stem cells would be the most useful source of cells for regenerative medicine because these cells are capable of differentiation into almost all of the organs by appropriate induction of their differentiation, with retaining their ability of actively dividing while maintaining their pluripotency. iPS cells, in particular, can be established from self-derived somatic cells, and therefore are not likely to cause ethical and social issues, in comparison with ES cells which are produced by destruction of embryos. Further, iPS cells, which are self-derived cell, make it possible to avoid rejection reactions, which are the biggest obstacle to regenerative medicine or transplantation therapy.

The isolated nucleic acids can be easily delivered to a subject by methods known in the art, for example, methods which deliver siRNA. In some aspects, the Cas may be a fragment wherein the active domains of the Cas molecule are included, thereby cutting down on the size of the molecule. Thus, the, Cas9/gRNA molecules can be used clinically, similar to the approaches taken by current gene therapy. In particular, a Cas9/multiplex gRNA stable expression stem cell or iPS cells for cell transplantation therapy as well as vaccination can be developed for use in subjects.

Transduced cells are prepared for reinfusion according to established methods. After a period of about 2-4 weeks in culture, the cells may number between $1 \times 10^6$ and $1 \times 10^{10}$. In this regard, the growth characteristics of cells vary from patient to patient and from cell type to cell type. About 72 hours prior to reinfusion of the transduced cells, an aliquot is taken for analysis of phenotype, and percentage of cells expressing the therapeutic agent. For administration, cells of the present invention can be administered at a rate determined by the $LD_{50}$ of the cell type, and the side effects of the cell type at various concentrations, as applied to the mass and overall health of the patient. Administration can be accomplished via single or divided doses. Adult stem cells may also be mobilized using exogenously administered factors that stimulate their production and egress from tissues or spaces that may include, but are not restricted to, bone marrow or adipose tissues.

Methods of Treatment

In certain embodiments, a method of eradicating a retrovirus genome in a cell or a subject, comprises contacting the cell or administering to the subject, a pharmaceutical composition comprising a therapeutically effective amount of an isolated nucleic acid sequence encoding a Clustered Regularly Interspaced Short Palindromic Repeat (CRISPR)-associated endonuclease and at least one guide RNA (gRNA), the gRNA being complementary to a target nucleic acid sequence in a retrovirus genome.

In other embodiments, a method of inhibiting replication of a retrovirus in a cell or a subject, comprising contacting the cell or administering to the subject, a pharmaceutical composition comprising a therapeutically effective amount of an isolated nucleic acid sequence encoding a Clustered Regularly Interspaced Short Palindromic Repeat (CRISPR)-associated endonuclease and at least one guide RNA (gRNA), the gRNA being complementary to a target nucleic acid sequence in a retrovirus genome.

In methods of treatment of a retrovirus infection, e.g. HIV infection, a subject can be identified using standard clinical tests, for example, immunoassays to detect the presence of HIV antibodies or the HIV polypeptide p24 in the subject's serum, or through HIV nucleic acid amplification assays. An amount of such a composition provided to the subject that results in a complete resolution of the symptoms of the infection, a decrease in the severity of the symptoms of the infection, or a slowing of the infection's progression is considered a therapeutically effective amount. The present methods may also include a monitoring step to help optimize dosing and scheduling as well as predict outcome. In some methods of the present invention, one can first determine whether a patient has a latent HIV infection, and then make a determination as to whether or not to treat the patient with one or more of the compositions described herein. In some embodiments, the methods can further include the step of determining the nucleic acid sequence of the particular HIV harbored by the patient and then designing the guide RNA to be complementary to those particular sequences. For example, one can determine the nucleic acid sequence of a subject's LTR U3, R or U5 region, or pol, gag, or env genes, region and then design or select one or more gRNAs to be precisely complementary to the patient's sequences. The novel gRNAs provided by the present invention greatly enhance the chances of formulating an effective treatment.

In methods of reducing the risk of HIV infection, a subject at risk for having an HIV infection can be, for example, any sexually active individual engaging in unprotected sex, i.e., engaging in sexual activity without the use of a condom; a sexually active individual having another sexually transmitted infection; an intravenous drug user; or an uncircumcised man. A subject at risk for having an HIV infection can be, for example, an individual whose occupation may bring him or her into contact with HIV-infected populations, e.g., healthcare workers or first responders. A subject at risk for having an HIV infection can be, for example, an inmate in a correctional setting or a sex worker, that is, an individual who uses sexual activity for income employment or non-monetary items such as food, drugs, or shelter.

The present invention also includes a kit including an isolated nucleic acid sequence encoding a CRISPR-associated endonuclease, for example, a Cas9 endonuclease, and at least one isolated nucleic acid sequence encoding a gRNA complementary to a target sequence in an HIV provirus. Alternatively, at least one of the isolated nucleic acid sequences can be encoded in a vector, such as an expression vector. Possible uses of the kit include the treatment or prophylaxis of HIV infection. Preferably, the kit includes instructions for use, syringes, delivery devices, buffers sterile containers and diluents, or other reagents for required for treatment or prophylaxis. The kit can also include a suitable stabilizer, a carrier molecule, a flavoring, or the like, as appropriate for the intended use.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

All publications and patent documents cited in this application are incorporated by reference for all purposes to the same extent as if each individual publication or patent document were so individually denoted. By their citation of various references in this document, applicants do not admit any particular reference is "prior art" to their invention.

EXAMPLES

Example 1: Materials and Methods

Cloning of sgRNA in lentiviral vector: Using bioinformatics spCas9-sgRNA design tools for best scores of high efficiency and high specificity, we designed 20 sgRNA target sites within HIV-1 LTR-U3 region and 4 sgRNA for Gag, 2 sgRNA for Pol and 2 sgRNAs for Env (Table 1). We cloned all these sgRNA seed sequence into modified sgRNA expression pKLV-Wg lentiviral vector (FIG. 1B) modified from the sgRNA lentiviral vector (Addgene #50946). Briefly, the pKLV-Wg vector was digested with BbsI and treated with Antarctic Phosphatase, and the linearized vector was purified with a Quick nucleotide removal kit (Qiagen). Equal amount of sense and antisense guides (100 □M in 1 µl) were mixed with polynucleotide kinase (PNK, 1 µl), 1×PNK buffer and 1 mM ATP, and incubated at 37° C. for 30 min followed by annealing in PCR machine (95° C. for 5 minutes, −1° C./cycle 15 sec for 70 cycles). The phosphorylated oligo duplex (10 µM) was diluted at 1:100 to get working solution (100 nM). Then, 1 µl oligo duplex (0.1 pmol) was mixed with 3.5 µl BbsI-digested pKLV-WG vector (0.015 pmol), 5 µl 2×T7 ligase reaction buffer and 0.5 µl T7 DNA ligase (NEB). The mixture was incubated for 15-30 minutes at room temperature, chilled on ice and then transformed into Stabl3 competent cells. Pick 2 to 4 colonies for PCR with T351 (U6/5') and sgRNA reverse primer. Grow 2 PCR positive clones in LB/Amp medium overnight at 37° C. Next day, miniprep plasmid DNAs were sent to Genewiz Inc. for sequencing with T428 (hU6-sequence/5'/F). The entire sgRNA expression cassette including U6 promoter, sgRNA and poly T terminator was verified by sequence analysis using GeneRunner program.

EcoHIV-luciferase reporter assay: HEK293T cells (5×10e4/well) were cultured in a 96-well plate in high-glucose DMEM containing 10% FBS and antibiotics (100 U/ml penicillin and 100 µg/ml streptomycin) in a humidified atmosphere with 5% CO2 at 37° C. The next day, cells were cotransfected by standard calcium phosphate precipitation with EcoHIV-eLuc reporter vector, pLV-Cas9-RFP vector, and indicated sgRNA expressing pKLV-Wg vectors. At 2 days after transfection, the cell lysate was prepared using the ONE-Glo luciferase assay system (Promega) and luminescence was measured in a 2104 EnVision® Multilabel Reader (PerkinElmer). Data represent mean±SE of 4 independent transfections. Relative changes in single or paired sgRNAs were calculated as compared with the empty sgRNA vector control.

PCR genotyping, TA cloning and Sanger sequencing: HEK293T cells in a 96-well plate were cotransfected with EcoHIV-eLuc reporter, pLV-EF1a-spCas9-T2A-RFP and indicated gRNA expression vectors. After 2 days, the cells were lysated with 90 µl 50 mM NaOH at 95° C. for 10 minutes and neutralized with 10 µl 1 M Tris-HCl. The crude extracts were directly used for PCR using Terra PCR Direct Polymerase Mix (Clontech) and the indicated PCR primers. Two steps of standard PCR were carried out for 35 cycles with 68° C. annealing/extension for 1 minute and 98° C. for 15 seconds. The products were resolved in 1.5% agarose gel. The bands of interest were gel-purified and cloned into pCRII T-A vector (Invitrogen), and the nucleotide sequence of individual clones was determined by sequencing at Genewiz using universal T7 and/or SP6 primers.

Example 2: HIV-1 gRNA Screening and Functional Characterization for HIV-1 Eradication In Vitro In order to broaden the spectrum of gRNAs effective for CRISPR-mediated editing of the HIV proviral genome, candidate gRNAs were found and screened for effectiveness in suppressing HIV expression and for the ability to induce deletion or eradication of the HIV-1 proviral genome in host cells.

Candidate gRNAs specific for target sites in the HIV-1 genome were found by bioinformatic procedures. The candidate gRNAs were selected for highest likelihood of providing effective gene editing, with minimum off-target potential, that is, the potential to cause damage to sites in the host genome. The target site seed sequences for candidate gRNAs within the U3 regulatory region of the LTR are shown in FIG. 1D. The gRNAs include LTR 1, LTR 2, LTR 3, LTR A, LTR B, LTR C, LTR D, LTR E, LTR F, LTR G, LTR H, LTR I, LTR J, LTR K, LTR L, LTR M, LTR N, LTR O, LTR P, LTR Q, LTR R, LTR S, LTR T. The sequences of these gRNAs is shown in Table 1. Most of these candidate gRNAs can be paired for use with Cas9 nickase and RNA guided FokI nuclease, which can reduce potential off-target effects by 1,500 fold. Candidate gRNAs targeting sites in the structural gag and pol genes are indicated by arrows in FIGS. 1C and 3A. These gRNAs include gag A, gag B, gag C, gag D; pol A, and pol B. Their sequences are shown in TABLE 1. The candidate gRNAs were cloned into lentiviral reporter vectors as shown in FIG. 1B, lower panel. spCas9 was also cloned into lentiviral reporter vectors, as shown in FIG. 1B, upper panel.

HEK293T host cells were cotransfected with an HIV reporter construct, EcoHIV-eLuc, a reporter expression construct for sPCas9, and one or two reporter expression constructs for gRNA. Control cells received control constructs ("LTR 0"). After 2 days, luciferase activity in the cell lysates was measured with a ONE-GLO™ Luciferase Assay system.

Figure 2A:
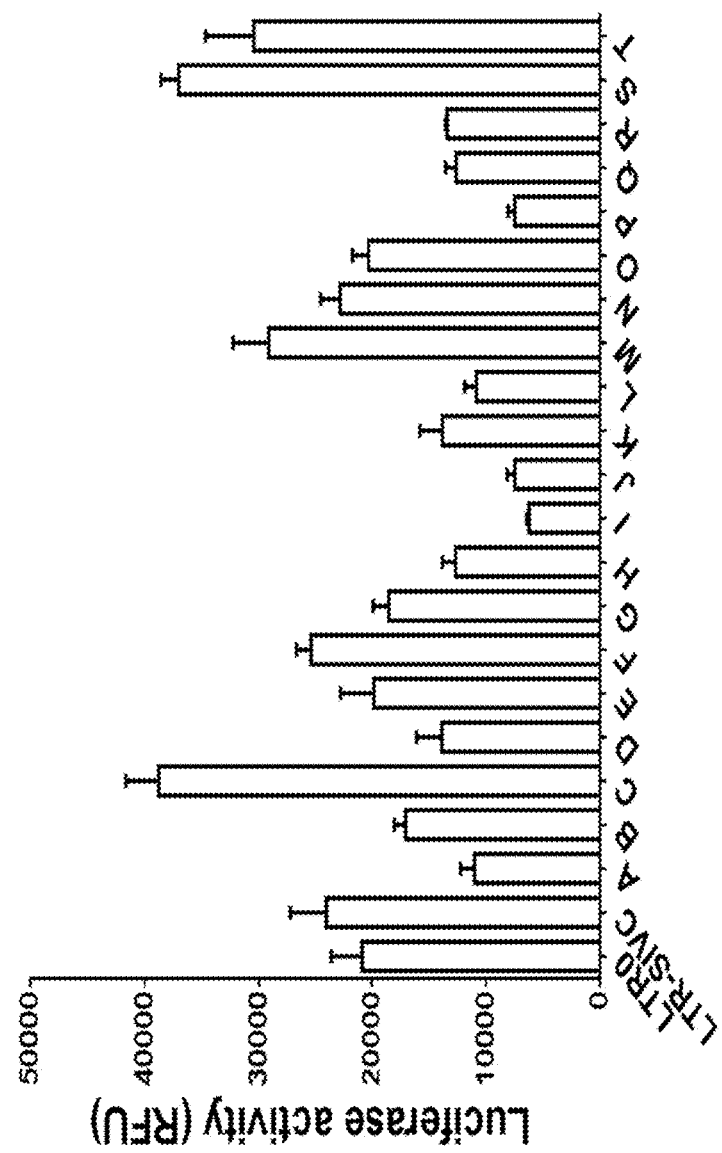
FIGS. 2A and 2D show single sgRNA screening by EcoHIV-luciferase reporter assay. HEK293T cells were cotransfected with EcoHIV-eLuc reporter, pLV-EF1a-spCas9-T2A-RFP and indicated sgRNA expression lentiviral vector. After 2 days, the luciferase activity in the cell lysates was measured with ONE-GLO™ Luciferase Assay System. Data represent mean±SE of 4 independent transfections.

Most of the candidate LTR gRNAs, administered alone, were effective in suppressing the expression of HIV-1 in the host cells, as determined by reduction in luciferase expression (FIG. 2A). These gRNAs were then cotransfected in various combinations with gRNAs targeting sites in the gag or pol genes. The combinations, shown on the abscissa of FIGS. 2B and 2C, included Gag D combined with one of LTR 1, LTR 2, LTR 3, LTR A, LTR B, LTR C, LTR D, LTR E, LTR F, LTR G; LTR H, LTR I, LTR J, LTR K, LTR L, LTR M; LTR N, LTR O, LTR P, LTR Q, LTR R, LTR S, or LTR T; and LTR 3 combined with one of Gag A; Gag B; Gag C, Gag D, Pol A, or Pol B.

Most of single gRNAs (FIG. 2A) inhibited the constitutive luciferase activity, but some enhanced the reporter activity or even had no effect. The data suggest that single site editing within the LTR induces InDel mutations that may affect the binding of transcriptional activators or repressors for HIV-1 LTR promoter activities.

Figure 2B:
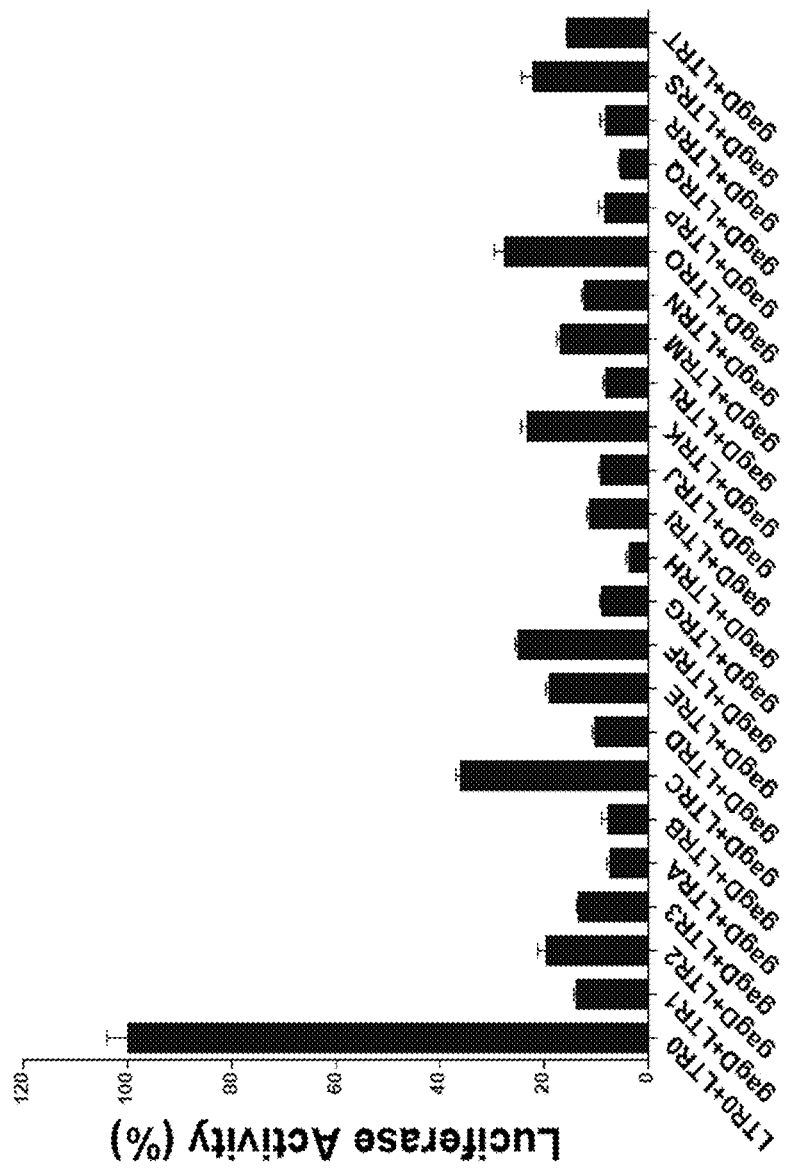
FIG. 2B shows that paired sgRNAs of Gag-D with any of the LTR-sgRNAs reduced luciferase activities by 64-96%. HEK293T cells were cotransfected with EcoHIV-eLuc reporter, pLV-EF1a-spCas9-T2A-RFP and the indicated sgRNA expression lentiviral vector. After 2 days, the luciferase activity in the cell lysates was measured with ONE-Glo™ Luciferase Assay System. Data represent mean±SE of 4 independent transfections.

However, paired gRNAs of Gag-D with any of the LTR-gRNAs reduced luciferase activities by 64-96% (FIG. 2B). These data suggest that all the designed gRNAs effectively induced gene editing of target sites at the plasmid levels. The combination of Gag with any LTR-sgRNAs will delete core promoter of LTR and thus induce the dramatic reduction in promoter activity. The remaining reporter luciferase activity may reflect the small population of EcoHIV reporter-expressing cells that do not contain either spCas9 or two sgRNAs. Note that the reduction efficiency requires the presence of all 4 plasmids in the same cells: EcoHIV-eLuc, spCas9, two sgRNAs.

Figure 2C:
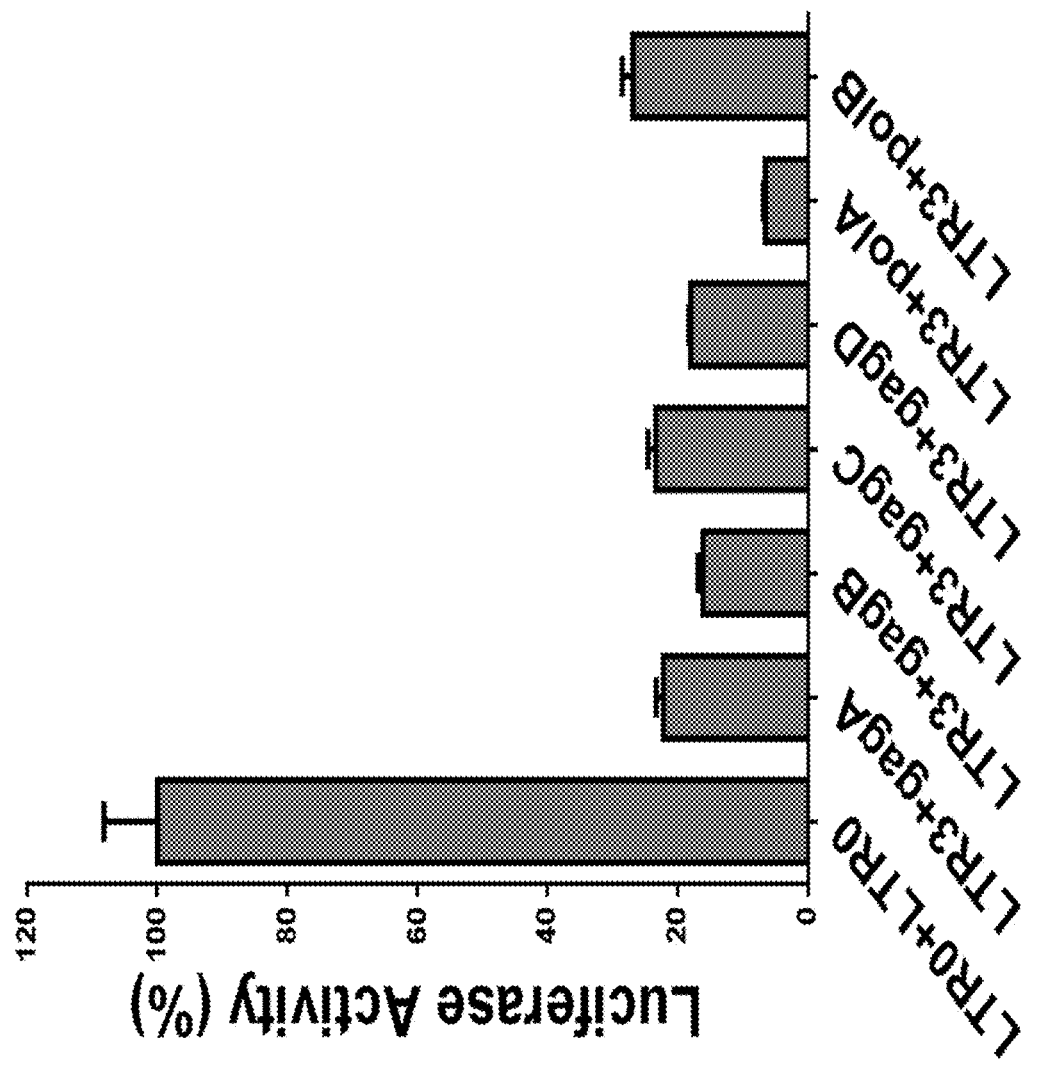
FIG. 2C shows that paired sgRNAs of LTR-3 with any of the Gag-sgRNAs or Pol-sgRNA reduced luciferase activities by 73-93%. HEK293T cells were cotransfected with EcoHIV-eLuc reporter, pLV-EF1a-spCas9-T2A-RFP and indicated sgRNA expression lentiviral vector. After 2 days, the luciferase activity in the cell lysates was measured with ONE-Glo™ Luciferase Assay System. Data represent mean±SE of 4 independent transfections.
Figure 2D:
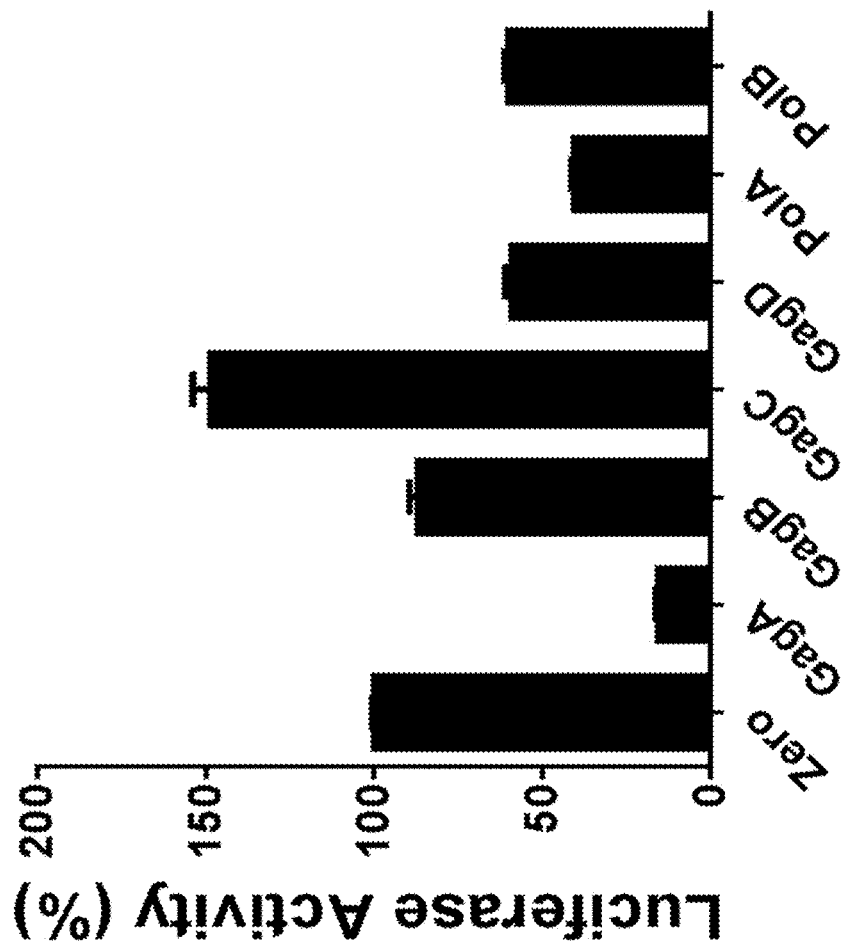

LTR-3 gRNA paired with any one of designed Gag or Pol gRNAs also dramatically reduced luciferase reporter activities by 73-93% (FIG. 2C). These data suggest that all the designed gRNAs targeting structural Gag or Pol region effectively induced gene editing of target sites at the plasmid levels. The combination of LTR-3 with any sgRNAs within structural region will delete core promoter of LTR and the structural genome between the cutting sites, and thus induce the dramatic reduction in promoter activity. Such proof of concept is applicable to any LTR-sgRNAs as well as any other sgRNAs targeting structural regions such as Gag, Pol and Env or any other non-structural region between both end LTRs. The residual reporter luciferase activity may reflect the small population of EcoHIV reporter-expressing cells that do not contain either spCas9 or two sgRNAs vectors. Note that the reduction efficiency requires the presence of all 4 plasmids in the same cells: EcoHIV-eLuc, spCas9, two sgRNAs.

It was next determined whether the suppression of HIV-1 expression reflected the deletion of segments of the HIV-1 proviral genome. HEK293T cells were cotransfected with EcoHIV-eLuc reporter, pLV-EF1a-spCas9-T2A-RFP and gRNA expression vectors. After 2 days, the cells were lysed with 50 mM NaOH at 95° C. for 10 minutes and neutralized with 1 M Tris-HCl. The crude extracts were directly used for PCR using Terra PCR Direct Polymerase Mix (Clontech) and the indicated PCR primers.

When a first set of primers was used (FIG. 3A), the PCR fragments after cutting of the designed targeting sites showed the predicted size in 17 of 20 LTR sgRNAs. Only LTR-F, LTR-G and LTR-K exhibited no eradication, suggesting that they are unable or less efficient to cleave 5'-LTR. This is consistent with the ineffective or less efficient result with LTR-F, LTR-G and LTR-K single sgRNA transfection as shown in FIG. 2A. Among the effective sgRNAs, the cut efficiency as detected by the ratio of cut fragment over corresponding uncut fragment was highest in sgRNAs LTR. Interestingly, additional band of bigger size than the predicted cut fragment was observed in most pairs When a second set of primers was used (FIG. 3B), two weak bands are observed in all samples, indicating the non-specific PCR products. However, unique PCR fragments after cutting of the designed targeting sites showed the predicted size in 16 of 20 LTR sgRNAs. Among the effective sgRNAs, the cut efficiency as detected by the intensity of the predicted PCR fragment was highest in sgRNAs LTR-Q, L, B, S, O, C, I.

Additional combinations of sgRNAs targeting the LTR and various structural genes were next examined. The combinations are indicated in FIG. 3C. Among LTR-1, 2, 3 sgRNAs, LTR-1 showed the best efficiency. Gag-A, C, D and Pol-A, B exhibited strong eradication efficiency. Gag-B showed no cleavage (confirmed by PCR repeat, right panel). Again, an additional band of bigger size than the predicted cut fragment was observed in the pairs for 5'LTR cleavage.

It was also found that pairs of gRNAs complementary to target sites in the LTR U3 region also produced deletions in the HIV-1 proviral genome. Sample preparation and Direct PCR were performed as previously described. The PCR fragments after cut were extracted for TA cloning and Sanger sequence (FIG. 4). Representative TA-cloning and Sanger sequencing confirmed 296 bp deletion between LTR-1 and LTR-3 and 180 bp additional insertion between the two cut sites. Sequencing of 15 clones showed similar pattern of perfect ligation without any indel mutation between the two cut sites. The additional 180 bp insert sequence matches vector sequence by NCBI Blast.

Taken together, the results show that most of the candidate gRNAs are effective to eradicate the predicted HIV-1 genome sequence between selected two targeting sites, and to suppress proviral expression, as shown by luciferase reporter activities. In particular, a combination of viral structural gRNAs with one or two LTR gRNAs provided a higher efficiency of genome eradication. The results of these experiments broaden the spectrum of gRNAs that can be employed in a CRISPR system to cause effective cleavage of HIV-1 genome.

Example 3: A Novel gRNA Combination and Vector System for Eradication of Integrated HIV-1 Genome from Latently Infected T Cells, Using the CRISPR/Cas9 Gene Editing System Experiments were performed with the aim of further broadening the spectrum of effective gRNAs against HIV-1, and to increase the flexibility of delivery of gRNAs and Cas9 to host cells.

A combination treatment strategy was first tested. The treatment employed the novel combination of the gRNA LTR B' together with LTR A, which was previously disclosed in Hu, et al, 2014. The sequences of LTR A and LTR B' are shown in FIG. 11A, and their positions in the HIV-1 LTR are indicated in FIGS. 5A-5D.

Combined expression of Cas9, LTR A and LTR B' gRNA abrogates activation of latent HIV provirus, and causes excision of proviral sequences: Experiments were carried out in Jurkat2D10 reporter T cell line, which is diagrammed in FIG. 6A. This cell line contains an integrated, transcriptionally latent HIV-1 provirus with eGFP in place of Nef as a reporter of proviral activation. Activation is induced by treatment with phorbol 12-myristate 13-acetate (PMA) or trichostatin A (TSA). The integrated HIV-1 reporter sequence is shown in FIG. 6A. Fluorescence micrographs of induced (right panel) and uninduced (left panel) 2D10 cells are shown in FIG. 6B. Flow cytometric analyses of induced (right panel) and uninduced (left panel) 2D10 cells are shown in FIG. 6C.

2D10 reporter cells ($2\times10^6$/condition) were electroporated with 10 μg of control pX260 plasmid or pX260 LTR-A and pX260 LTR-B' plasmids, 5 μg each (Neon System, Invitrogen, 3 times 10 ms/1350V impulse). 48 h later medium was replaced with medium containing puromycin 0.5 ug/ml. After one week of selection, puromycin was removed and cells were allowed to grow for another week. The cells also expressed FLAG-tagged Cas9.

Next, cells were diluted to a concentration of 10 cells/ml and plated in 96 well plates, 50 ul/well. After 2 weeks, single cell clones were screened for GFP tagged HIV-1 reporter reactivation (12 h PMA 25 nM/TSA 250 nM treatment), using a Guava EasyCyte Mini flow cytometer.

Clones expressing Cas9, LTR A, and LTR B' were compared to clones expressing only Cas9 (FIGS. 7A-7C). It was found that only clones expressing Cas9, LTR A, and LTR B' failed to show HIV-1 reporter reactivation after PMA induction (FIG. 7B, bottom panel). In contrast, clones expressing only Cas9 did show HIV-1 reporter reactivation, as evidenced by EGFP expression (FIG. 7B, top panel).

It was next determined whether abrogation of reactivation of latent reporter HIV-1 provirus was attributable to successful excision of proviral sequences from the host genome. DNA derived from clones analyzed in the previous experiment was subjected to PCR to amplify the proviral env gene sequence motif RRE, or genomic sequences flanking the integrated reporter provirus (MSRB1 gene). T location of the primers is shown in FIG. 8A.

PCR analysis showed that clones expressing Cas9 and the LTR A/B' combination failed to show PCR products including RRE and MSRB1, indicating excision of DNA including those sequences. In contrast, RRE and MSRB1 were amplified and readily detectable in clones expressing only Cas9 (FIG. 8B). Long range PCR genotyping confirmed that expression of the LTR A/B combination resulted in the excision of a 652 bp sequence extending between the 5' U3 region and the 3' U3 region (FIG. 8C). The excision was further confirmed by sequencing the cleavage lariat from the integration locus in chromosome 16 (FIG. 8D). Taken together, the results confirm that the abrogation of reactivation of latent HIV-1 provirus, by LTR A/B' and Cas9 expression, was caused by the excision of proviral sequences from the host genome.

It was also found that stable expression of LTR A/B' and Cas9 protected the 2D10 clones from new infection by HIV-1. Clones were characterized for Cas9 expression by Western blotting (FIG. 9B), and for expression of LTR B' by reverse PCR analysis (FIG. 9C). The clones were infected with HIV-1 NL4-3-EGFP-P2A-NEF reporter virus and monitored for progression of infection by FACS analysis. Only clones that expressed both LTRA/B' and Cas9 resisted HIV-1 infection. This is shown by dramatically lower levels of EGFP expression relative to clones lacking either LTR A/B' (ctrl 7) or Cas 9 (AB 8) (FIG. 9A).

Lentiviral delivery of Cas9/gRNA allows efficient and time controlled targeting of proviral sequences: It was next determined whether lentiviral vectors can be used for the expression of Cas9/gRNA components in host cells. Lentiviral vectors provide a versatile and flexible means of expression, and a variety of drug inducible lentiviral vectors are available. Jurkat 2D10 were transduced with lentiviruses expressing RFP-Cas9 (red fluorescence) and/or LTR A/B' gRNAs (BFP marker, blue fluorescence) at MOI 5 (FIG. 10A). 72 hours later, GFP reporter virus was reactivated using PMA/TSA treatment and quantified by flow cytometry. Dot plot analyses are shown in FIG. 10B). HIV activation is detectable as an upward (green) shift in the dot plot upon induction (e.g. FIG. 10B left top panel vs. left bottom panel). It can be seen that only cells transduced with both Cas9 and LTR A/B' show a significant cell fraction that does not exhibit the green upshift (FIG. 10B, right bottom panel). The results confirm that the components of the Cas9/gRNA can be effectively delivered by lentiviral vectors.

Cas9/LTR A/B' expression causes no detectable off-target effects and minimal changes in adjacent gene expression: Effective excision of HIV-1 provirus by CRISPR editing is of little use if it is accompanied by induced mutations in normal host genes containing sequences similar to target sequences. Six predicted/possible off-target sites for LTR A/B' were examined in Jurkat clones in which an HIV-1 genome had been successfully eradicated. The sequences of LTRA and LTRB' are shown in FIG. 11A. No indel mutations were shown, either by Surveyor assay reactions (FIG. 11B) or Sanger sequencing (FIG. 11C). Localization of HIV-1 reporter integration site in the second exon of the MSRB1 gene in chromosome 16, and neighboring genes, are shown in FIG. 11D. Levels of expression of genes adjacent to the integration site after HIV-1 sequence eradication was measured by qRT-PCR and compared to levels of expression in control cells. The results, in FIG. 11E, show that effective treatment with Cas9 and LTR AB' has no significant impact on the expression of genes neighboring the excised HIV sequences.

Example 4: Functional Screening of Guide RNAs Targeting the Regulatory and Structural HIV-1 Viral Genome for a Cure of AIDS In this study, the best gRNAs targeting HIV-1 LTR and viral structural region were identified the gRNA pairing that can efficiently eradicate the HIV-1 genome was optimized.

Highly specific gRNAs were designed using bioinformatics tools and their capacity of guiding Cas9 to cleave HIV-1 proviral DNA was evaluated using high throughput HIV-1 luciferase reporter assay and rapid Direct-PCR genotyping.

TABLE 1

Oligonucleotides for gRNAs targeting HIV-1 LTR, Gag and Pol and PCR primers.

| Target name | Direction | Sequences (5' to 3') |
|---|---|---|
| LTR-A | T353: Forward | aaacAGGGCCAGGGATCAGATATCCACTGACCTTgt (SEQ ID NO: 1) |
|  | T354: Reverse | taaacAAGGTCAGTGGATATCTGATCCCTGGCCCT (SEQ ID NO: 2) |
| LTR-B | T355: Forward | aaacAGCTCGATGTCAGCAGTTCTTGAAGTACTCgt (SEQ ID NO: 3) |
|  | T356: Reverse | taaacGAGTACTTCAAGAACTGCTGACATCGAGCT (SEQ ID NO: 4) |
| LTR-C | T357: Forward | caccGATTGGCAGAACTACACACC (SEQ ID NO: 5) |
|  | T358: Reverse | aaacGGTGTGTAGTTCTGCCAATC (SEQ ID NO: 6) |
| LTR-D | T359: Forward | caccGCGTGGCCTGGGCGGGACTG (SEQ ID NO: 7) |
|  | T360: Reverse | aaacCAGTCCCGCCCAGGCCACGC (SEQ ID NO: 8) |
| LTR-E | T361: Forward | caccGATCTGTGGATCTACCACACA (SEQ ID NO: 9) |
|  | T362: Reverse | aaacTGTGTGTGGTAGATCCACAGATC (SEQ ID NO: 10) |
| LTR-F | T363: Forward | caccGCTGCTTATATGCAGCATCTGAG (SEQ ID NO: 11) |
|  | T364: Reverse | aaacCTCAGATGCTGCATATAAGCAGC (SEQ ID NO: 12) |
| LTR-G | T530: Forward | caccGTGTGGTAGATCCACAGATCA (SEQ ID NO: 13) |
|  | T531: Reverse | aaacTGATCTGTGGATCTACCACAC (SEQ ID NO: 14) |
| LTR-H | T532: Forward | caccGCAGGGAAGTAGCCTTGTGTG (SEQ ID NO: 15) |
|  | T533: Reverse | aaacCACACAAGGCTACTTCCCTGC (SEQ ID NO: 16) |
| LTR-I | T534: Forward | caccGATCAGATATCCACTGACCTT (SEQ ID NO: 17) |
|  | T535: Reverse | aaacAAGGTCAGTGGATATCTGATC (SEQ ID NO: 18) |
| LTR-J | T536: Forward | caccGCACACTAATACTTCTCCCTC (SEQ ID NO: 19) |
|  | T537: Reverse | aaacGAGGGAGAAGTATTAGTGTGC (SEQ ID NO: 20) |
| LTR-K | T538: Forward | caccGCCTCCTAGCATTTCGTCACA (SEQ ID NO: 21) |
|  | T539: Reverse | aaacTGTGACGAAATGCTAGGAGGC (SEQ ID NO: 22) |
| LTR-L | T540: Forward | caccGCATGGCCCGAGAGCTGCATC (SEQ ID NO: 23) |
|  | T541: Reverse | aaacGATGCAGCTCTCGGGCCATGC (SEQ ID NO: 24) |
| LTR-M | T542: Forward | caccGCAGCAGTCTTTGTAGTACTC (SEQ ID NO: 25) |
|  | T543: Reverse | aaacGAGTACTACAAAGACTGCTGC (SEQ ID NO: 26) |
| LTR-N | T544: Forward | caccGCTGACATCGAGCTTTCTACA (SEQ ID NO: 27) |
|  | T545: Reverse | aaacTGTAGAAAGCTCGATGTCAGC (SEQ ID NO: 28) |
| LTR-O | T546: Forward | caccGTCTACAAGGGACTTTCCGCT (SEQ ID NO: 29) |
|  | T547: Reverse | aaacAGCGGAAAGTCCCTTGTAGAC (SEQ ID NO: 30) |
| LTR-P | T548: Forward | caccGCTTTCCGCTGGGGACTTTCC (SEQ ID NO: 31) |
|  | T549: Reverse | aaacGGAAAGTCCCCAGCGGAAAGC (SEQ ID NO: 32) |
| LTR-Q | T687: Forward | caccGCCTCCCTGGAAAGTCCCCAG (SEQ ID NO: 33) |
|  | T688: Reverse | aaacCTGGGGACTTTCCAGGGAGGC (SEQ ID NO: 34) |
| LTR-R | T689: Forward | caccGCCTGGGCGGGACTGGGGAG (SEQ ID NO: 35) |
|  | T690: Reverse | aaacCTCCCCAGTCCCGCCCAGGC (SEQ ID NO: 36) |

TABLE 1 -continued

Oligonucleotides for gRNAs targeting HIV-1 LTR,
Gag and Pol and PCR primers.

| Target name | Direction | Sequences (5' to 3') |
|---|---|---|
| LTR-S | T691: Forward | caccGTCCATCCCATGCAGGCTCAC (SEQ ID NO: 37) |
|  | T692: Reverse | aaacGTGAGCCTGCATGGGATGGAC (SEQ ID NO: 38) |
| LTR-T | T548: Forward | caccGCGGAGAGAGAAGTATTAGAG (SEQ ID NO: 39) |
|  | T549: Reverse | aaacCTCTAATACTTCTCTCTCCGC (SEQ ID NO: 40) |
| Gag-A | T687: Forward | caccGGCCAGATGAGAGAACCAAG (SEQ ID NO: 41) |
|  | T688: Reverse | aaacCTTGGTTCTCTCATCTGGCC (SEQ ID NO: 42) |
| Gag-B | T714: Forward | caccGCCTTCCCACAAGGGAAGGCCA (SEQ ID NO: 43) |
|  | T715: Reverse | aaacTGGCCTTCCCTTGTGGGAAGGC (SEQ ID NO: 44) |
| Gag-C | T758: Forward | caccGCGAGAGCGTCGGTATTAAGCG (SEQ ID NO: 45) |
|  | T759: Reverse | aaacCGCTTAATACCGACGCTCTCGC (SEQ ID NO: 46) |
| Gag-D | T760: Forward | caccGGATAGATGTAAAAGACACCA (SEQ ID NO: 47) |
|  | T761: Reverse | aaacTGGTGTCTTTTACATCTATCC (SEQ ID NO: 48) |
| Pol-A | T689: Forward | caccGCAGGATATGTAACTGACAG (SEQ ID NO: 49) |
|  | T690: Reverse | aaacCTGTCAGTTACATATCCTGC (SEQ ID NO: 50) |
| Pol-B | T716: Forward | caccGCATGGGTACCAGCACACAA (SEQ ID NO: 51) |
|  | T717: Reverse | aaacTTGTGTGCTGGTACCCATGC (SEQ ID NO: 52) |
| PCR | T422 | caccGCTTTATTGAGGCTTAAGCAG (SEQ ID NO: 53) |
|  | T425 | aaacGAGTCACACAACAGACGGGC (SEQ ID NO: 54) |
|  | T645 | TGGAATGCAGTGGCGCGATCTTGGC (SEQ ID NO: 55) |
|  | T477 | CACAGCATCAAGAAGAACCTGAT (SEQ ID NO: 56) |
|  | T478 | TGAAGATCTCTTGCAGATAGCAG (SEQ ID NO: 57) |

Results

Bioinformatics screening of sgRNAs with high efficiency and low off-target. The efficiency and specificity of target gRNAs are critical concerns for Cas9/gRNA application in infectious diseases. Several computing programs have been developed for the design and selection of gRNAs for the spCas9-gRNA system, wherein the 20 bp seed sequence and NRG PAM were used. While most of the gRNA design programs were developed to predict off-target effects, very few programs were able to predict cleaving efficiency. Twenty (20) gRNAs targeting the HIV-1 LTR were designed with a high score of cleaving efficiency and specificity against the human genome (Table 1) utilizing the following criteria: (1) Targeting −18 to −418 bp region of LTR-U3 promoter to disrupt HIV-1 initial transcription (and suppress virus production), and this 400 bp region is precluded in most LVs, thus avoiding LV self-cleavage; (2) Avoiding transcription factor binding sites that may affect the expression of host cellular genes due to high homology (FIG. 1C); (3) Matching both end LTRs to enable elimination of entire proviral DNA between LTRs; (4) Off-target score at more than 50%; and (5) Applicability to the double spCas9 nickase or dimeric RNA-guided FokI nucleases. A few gRNAs targeting the structural region Gag and Pol (FIG. 1C) with a hope of obtaining the best combination of gRNAs to eradicate HIV-1 entire genome. The Env structural region was not selected due to lower conservation in this structural sequence between different strains. The LV gene delivery system was chosen separately for expressing spCas9 and gRNA (FIG. 1B) for the following reasons: (1) LV itself provides many benefits for high efficient gene therapy in hard-to-transfect HIV-latent cell lines, animal studies and potential clinical application (integration-free LV; Hu P, et al. *Mol Ther Methods Clin Dev* 2015, 2:15025; Liu K C, et al. *Curr Gene Ther* 2014, 14:352-364); (2) The separate spCas9 LV ensures good packaging efficiency for the large size of spCas9 gene; (3) Separate gRNA expressing LV can be used for cloning multiplex gRNA expressing cassettes into one vector for good packaging efficiency.

Functional screening in HEK293T cells to identify effective gRNAs. For a rapid functional screening of the best targets, an EcoHIV-eLuc reporter assay was performed using a high-throughput Envision multiple plate reader. The EcoHIV-eLuc reporter was selected because (1) it contains all the components needed for HIV-1 replication except for the HIV Env, (2) convenient to be handled at biosafety level II containers due to Env deletion and (3) bioluminescence is more sensitive than fluorescence and the eLuc reporter can be used to detect less than 10 single cells (Song J, et al. *J Gen Virol* 2015, 96:3131-3142). The HEK293T cell line was chosen because of the high transfection efficiency with the cost-effective calcium phosphate precipitation method. With single gRNA transfection, it was found that most gRNAs targeting the LTR promoter and the structural region could only result in marginal reduction of EcoHIV proviral reporter production but some increased the promoter activities or had no effect (FIGS. 2A, 2B). The increase in promoter activity is consistent with a recent report that spCas9/gRNA-induced DSB within the promoter of neuronal early response genes stimulates their expression (Madabhushi R, et al. *Cell* 2015, 161:1592-1605). A single gRNA was hypothesized to induce a single cut of the target sites, generating InDel mutations in the targeted regions and/or the deletion of the entire proviral DNA between both end LTRs. The mutation in the promoter may affect the functional activities of transcriptional activators and/or repressors, which may lead to an increase or decrease in the transcriptional activity. Mutation in the structural region may result in the shift of the open-reading frame of the HIV-1 structural proteins and thus decrease the expression of eLuc reporter.

To obtain more reliable and sensitive screening of the effective gRNAs for functional cleavage, the paired gRNAs were co-transfected: each LTR gRNA v.s. one of the gRNAs targeting the structural region. With this strategy, a more dramatic reduction of reporter virus was observed due to a large fragment deletion between either 5' or 3' LTR and the structural region. As an example shown in FIG. 2B, all combinations between GagD and any one of LTR-gRNAs reduced the eLuc expression significantly (64-96%), which is more robust than using a single gRNA. Half of LTR-gRNAs (10/20) showed >90% reduction in eLuc activity. Similarly, as another example shown in FIG. 2C, LTR-R gRNA paired with any one of GagA-D or PolA-B significantly reduced luciferase reporter activity to 7-23%. Selection of GagD or LTR-R for the pairing was also based on their PAM site applicable to *Staphylococcus aureus* Cas9 system and their targeting sites applicable to HIV-1 latent cell lines (Jadlowsky J K, et al. *Mol Cell Biol* 2014, 34:1911-192) and Tg26 transgenic mice (Kopp J B, et al. *Proc Natl Acad Sci USA* 1992, 89:1577-1581) wherein the partial Gag and entire Pol sequences were deleted. These data provided evidence that a combination of LTR-gRNA with structural gRNAs was a better and easier strategy to screen the effective gRNAs using high-throughput HIV-1 eLuc reporter assay. All the designed gRNAs are functional to reduce the expression of EcoHIV-eLuc reporter, which is consistent with the high score of the efficiency prediction by the bioinformatics analysis.

Identification of effective gRNAs using Direct PCR genotyping. To validate whether these candidate gRNAs are functional to cleave the appropriate targets as designed, Direct-PCR genotyping analysis was performed using the DNA samples with the paired gRNAs and corresponding PCR primers as indicated (FIG. 3D). The Direct-PCR approach does not require DNA extraction and purification and is thus more convenient for genotype screening. When one of the gRNAs targeting structural regions was used to pair with LTR targeting sites, PCR genotyping apparently generated new fragments (designated Deletion for convenient description) derived from the remaining (residual) viral LTR and Gag sequence after the deletion of fragments between 5' LTR to Gag (FIG. 3E, primer T361/T458). Consistent with the eLuc reporter assay, almost all the gRNAs induced various degrees of reduction in the wild-type band which can be easily amplified by the standard PCR condition on the 5'-LTR/Gag because of the size (1.3 kb). After cleavage, various degrees of Deletion as designed were detected in most combinations (FIG. 3E). Interestingly, additional fragments (designated Insertion) larger than the predicted Deletion were observed in most combinations on the 5'-LTR-Gag cleavage (FIG. 3E). Quantification of wild-type band intensity showed that LTR-O possesses the highest efficacy, followed by I, C, A as shown in box (FIG. 3E). This wild-type band cleaving efficiency pattern was not completely correlated with the reduction pattern of eLuc reporter activity (FIG. 2B), likely because the amplification of PCR product in a mix population usually prefers the small size product. On the other hand, weak reduction of the wild-type band in some pairs might result from various degrees of small InDel mutations (within a few nucleotides) within the gRNA target sites without any fragmental Deletion or Insertion. To avoid the potential influence of the PCR preferential amplification, PCR genotyping was performed using primers covering 3'-LTR and Gag (FIGS. 3E, 3I, 3J), which is predicted to generate 7 kb wild-type PCR product that is unlikely to be amplified by the PCR setting used. The fragmental Deletion pattern among the gRNAs detected by the single PCR product (FIGS. 3E, 3I, 3J) was consistent with that revealed by the relative ratio changes (FIG. 3E). The pair of LTR-K and GagD exhibited no Deletion or Insertion fragmental band in all the four sets of PCR genotyping reactions (FIGS. 3E, 3F, 3I, 3J), correlating to only 7% reduction in the wild-type band (FIG. 3E). The pair of LTR-F vs. GagD showed weak deletion band in one set of PCR reaction (3I), correlating to 17% reduction in the wild-type band (FIG. 3E). The pairs of LTR-G, P vs. GagD showed around 50% reduction in the wild-type bands, resulting from the deletion in either 5'-LTR-Gag (FIG. 3E) or Gag-3'-LTR cleavage (FIG. 3F, 3I, 3J). When the LTR-R was used to pair with any one of GagA-D and PolA-B, PCR genotyping with indicated corresponding primers also generated predicted new fragments (Deletion) (FIG. 3G, 3H) and additional insertions on the 5'-LTR/Gag (FIG. 3G) to various extent in all the tested gRNAs except for Gag-B gRNA, which exhibited very weak editing capacity (FIG. 3G). However, all these combinations with weak or no deletion genotyping still showed dramatic reduction in Eco-HIV-eLuc reporter activity (FIG. 2B). This might be attributed to none or only one of the two gRNA plasmids transfected into the same cells wherein the single gRNA remains highly effective in inducing small InDel mutation. Taken together, these data evidence that the Direct-PCR genotyping provide a reliable and fast tool to validate the presence of fragmental Deletion and/or Insertion. However, evaluation of the efficacious HIV-1 eradication by various gRNAs requires a combination of functional reduction by the virus reporter assay and proviral DNA fragmental excision by the 5'-LTR or 3'-LTR-directed PCR genotyping.

Validation of fragmental Insertion/Deletion mutation by TA-cloning and Sanger sequencing. To further validate cleaving efficiency of spCas9/gRNAs and examine the pattern of Deletion/Insertion mutation after cleavage, three representative samples of PCR genotyping for TA-cloning and Sanger sequencing were selected. Paired expression of LTR-R/GagA caused a Deletion of a 519-bp fragment between LTR-R and GagA target sites (FIG. 12A). Co-expression of LTR-L/GagD (FIG. 12B) and LTR-M/GagD (FIG. 12C) led to a Deletion of a 772-bp or 763-bp fragment between each pair of target sites respectively. Furthermore, they caused various extents or types of small InDels. In some cases, a large Insertion of additional sequences (e.g. 159-359 bp) was identified (FIGS. 3E, 12B, 12C). NCBI Blast analysis showed that these additional sequences derived from the exogenous vectors instead of endogenous host cellular genes. These results indicate that most of these candidate gRNAs can efficiently mediate targeted disruption of integrated HIV genome by either excision or insertion/deletion.

Discussion

Multiplex gRNAs could induce a deletion of large fragments between the target sites (Hu W, et al. *Proc Natl Acad Sci USA* 2014, 111:11461-11466), which provides a reliable remedy to evaluate the DNA cleavage efficiency of Cas9/gRNAs. In this study, this proof of concept was further validated by screening various multiplexes of 26 gRNAs. It was demonstrated that most of the designed gRNAs are highly effective at eradicating the predicted HIV-1 genome sequence between the two selected targeting sites leading to significant excision of HIV-1 reporter virus. In particular, a combination of viral structural gRNAs with one or two LTR gRNAs provided a much higher efficiency of genome eradication and an easier approach with Direct-PCR genotyping and high throughput reporter screening. The effectiveness and specificity of the gRNAs selected in this study for excising HIV-1 proviral DNA promise a success in the preclinical animal and clinical patient studies using Cas9/gRNA technology, because: (1) These gRNAs can serve as a ready-to-use selection source to develop viral and non-viral gene therapy; (2) For individual HIV-1 patient, these gRNAs can be used as a master to screen new gRNAs designed specifically for any HIV-1 isolates despite of high mutation rate of HIV-1; (3) Easy gRNA cloning, rapid reporter screening and reliable Direct-PCR genotyping provide a feasibility for practical application of Cas9/gRNAs to the personalized medicine.

Not all the designed gRNAs exhibit needed activities in cleaving the expected target sites. Several approaches have been developed thus far to evaluate the efficiency of genome editing induced by Cas9/gRNAs technology. Continuously improving computational programs for efficiency predictions have been tested using host cellular genomes as the design target (Doench J G, et al. Nat Biotechnol 2014, 32:1262-1267; Gagnon J A, et al. *PLoS One* 2014, 9:e98186; Liu H, et al. *Bioinformatics* 2015) but may not be reliable for applying to the exogenous genomes such as infectious viruses. The Sanger sequencing of the target region via PCR cloning provides high sensitivity and specificity for determining genome editing efficiency (Sander J D, et al. *Nat Biotechnol* 2011, 29:697-698), however it is labor-intensive for high throughput screening. Mismatch-based Surveyor assay (Qiu P, et al. *Biotechniques* 2004, 36:702-707; Kim J M, et al. *Nat Commun* 2014, 5:3157; Dahlem T J, et al. *PLoS Genet* 2012, 8:e1002861) and high resolution melt analysis (Bassett A R, Liu J L. *J Genet Genomics* 2014, 41:7-19) are sensitive to detect the small InDel mutations but the poor specificity makes them prone to produce false positive results. The restriction fragment length polymorphism (RFLP) assay requires the presence of a restriction enzyme site with the target region, which is limited in most cases (Kim J M, et al. *Nat Commun* 2014, 5:3157). Next generation sequencing provides a reliable and specific measure but is expensive and time-consuming (Guell M, et al. *Bioinformatics* 2014, 30:2968-2970). Recently several PCR-based assays provide an easy and reliable method to quantify editing efficiency but they require robust primer design, trace decomposition or capillary sequencer (Brinkman E K, et al. Nucleic Acids Res 2014, 42:e168; Carrington B, et al. *Nucleic Acids Res* 2015; Yu C, et al. *PLoS One* 2014, 9:e98282). Here, a fast, cost-effective and reliable screening platform was established to identify effective gRNAs using highly sensitive high-throughput bioluminescent reporter assay along with a fast Direct-PCR genotyping. The reporter assay relies on the eradication of large fragments between two gRNA target sites as well as the small InDel mutations at each gRNA site. The fragmental eradication abolishes promoter activity or reporter expression while the InDel mutations may change the promoter regulation or induce open read frame shift of viral proteins. All these events will subsequently affect the activity of the reporter. The PCR genotyping relies on the fragmental cleavage and efficient re-ligation between the remaining end DNAs. The presence of the re-ligated PCR fragments provides an affirmative evidence for efficiency of both gRNAs. The re-ligation efficiency depends upon the cell dividing, thus the PCR genotyping may be limited in the case of non-dividing cells. In addition, the PCR condition for some primers needs optimization to achieve best efficiency of genotyping.

The objective of this study was to screen and identify the effective gRNAs by establishing reliable and sensitive high-throughput assays. Transient transfection of EcoHIV-eLuc reporter in HEK293T cells was chosen as a testing platform because a small amount of the reporter plasmid over spCas9/gRNA components (1:20) can ensure the target cleavage in all the reporter-expressing cells and thus maximize the detection efficiency of luciferase reporter assay and PCR genotyping. In contrast, the EcoHIV-eLuc stable cell line based on HEK293T cells (FIGS. 13A-13E, 14A-14D), which may be closer to the real situation of HIV-1 latency, showed a poor detection sensitivity in both luciferase reporter assay and PCR genotyping. This is because the EcoHIV-eLuc-expressing cells without any gRNA plasmid always exist after transfection and thus eLuc reporter is constantly expressed, even while the transfection efficiency can be as high as 80-90%. Additional advantages of the transient reporter transfection include easy setup, cost-effective transfection and high-throughput luminescence measurement. Importantly, the identified gRNAs remain effective in the real HIV latently-infected cells or cell lines and can be further used for animal studies and clinical applications. Although the transiently transfected EcoHIV-eLuc reporter (episomal DNA) does not reflect the latent HIV proviral DNA in the host genome (nucleus), the spCas9/gRNA-mediated gene editing works in a similar efficiency between episomal and nuclear DNA of HIV provirus (Hu W, et al. *Proc Natl Acad Sci USA* 2014, 111:11461-11466) and other viruses (Ramanan V, et al. *Sci Rep* 2015, 5:10833; Yuen K S, et al. *J Gen Virol* 2015, 96:626-636). Furthermore, the effective cleavage of the episomal DNA in addition to integrated HIV-1 proviral DNA allows for a novel preventative treatment for new infection of HIV (Hu W, et al. *Proc Natl Acad Sci USA* 2014, 111:11461-11466) and other infectious viruses (Peng C, Lu M, Yang D. *Virol Sin* 2015, 30:317-325).

Some confounding factors may affect the transient transfection efficiency and transgene expression for the comparative analysis of different gRNAs. To minimize this, several precautions were taken: 1) A master mixture of the reporter and spCas9 plasmids was prepared to ensure equal amount of these shared plasmids in each group of gRNAs; 2) *Renilla* luciferase reporter (1:100) was used for normalization of transfection efficiency; 3) A large scale of transfection was performed in 96-well plate for all the gRNAs in 4-6 replicates at the same time; and 4) All the data were expressed as relative changes compared with the empty gRNA control in each experiment.

One gRNA targeting the LTR region may eliminate the entire proviral DNA due to the cleavage of both end LTRs but the eradication efficiency was not apparent as shown by the EcoHIV-eLuc reporter assay. It also requires long-range PCR to verify the eradication of entire HIV-1 proviral DNA because standard PCR with primers covering the LTR cannot distinguish 5'-LTR from 3'-LTR after deletion of a fragment between two LTR target sites (Hu W, et al. *Proc Natl Acad Sci USA* 2014, 111:11461-11466). Two gRNAs targeting LTR region induced fragmental cleavage within each LTR region that will suppress LTR promoter activity and reduce HIV-1 RNA stability, thus improving the entire eradication efficiency as we have demonstrated previously (Hu W, et al. 2014). In this study, a new proof of principle was tested that any pair of gRNAs between the LTR and structural regions provides a better approach to evaluate HIV-1 eradication efficiency. By this method, the dramatic functional reduction in HIV-1 reporter virus production results from the three possible cleavages of 5'LTR+Gag, Gag+3'LTR and both end LTRs and can be easily monitored by the sensitive and high-throughput bioluminescence reporter assay. These cleavages can be efficiently and reliably detected by the standard and fast Direct-PCR genotyping using primers covering the LTR and structural regions. Similarly, a cocktail of two LTR gRNAs plus one or two structural gRNAs may provide an optimal and economical remedy to eradicate HIV-1 genome in the preclinical and clinical setting.

The potential for off-target effects involving the Cas9/gRNA technology has been a big concern in the field of genome editing. Stringent gRNA design, functional screening and Cas9 technology modification have been developing to increase the specificity of genome editing. Very rare instances of off-target effects related to spCas9/gRNAs in cultured cells have been validated by whole genome sequencing (WGS) (Hu W, et al. 2014; Zuckermann M et al. *Nat Commun* 2015, 6:7391; Smith C, et al. *Cell Stem Cell* 2014, 15:12-13; Veres A, et al. *Cell Stem Cell* 2014, 15:27-30; Yang L, et al. *Nat Commun* 2014, 5:5507). Newly developed unbiased profiling techniques further validate the high specificity of this spCas9-gRNA system (Ran F A, et al. *Nature* 2015, 520:186-191; Tsai S Q, et al. *Nat Biotechnol* 2015, 33:187-197; Frock R L, et al. *Nat Biotechnol* 2015, 33:179-186). In vivo off-target is expected to be much lower due to epigenetic protection. In this study, the exogenous viral DNA was analyzed against the host genome for best score of efficiency and specificity. No cellular toxicity was observed during gRNA screening. Double spCas9 nickases and RNA-guided FokI nucleases have shown to reduce potential off-target effects by up to 1500-fold (Ran F A, et al. *Cell* 2013, 154:1380-1389; Mali P, et al. *Nat Biotechnol* 2013, 31:833-838; Wyvekens N, et al. *Hum Gene Ther* 2015, 26:425-431; Tsai S Q, et al. *Nat Biotechnol* 2014, 32:569-576).

In conclusion, most of the designed gRNAs are highly effective to eradicate the predicted HIV-1 genome sequence between selected two targeting sites and affect eLuc reporter activities. In particular, a combination of viral structural gRNAs with one or two LTR gRNAs provided a higher efficiency of genome eradication and an easier approach for PCR genotyping. The screening with HIV-1 eLuc reporter assay and Direct-PCR genotyping provides a reliable, rapid and convenient approach to screen effective HIV-1 gRNAs. This can be utilized to set up high throughput gRNA library screen for any new HIV-1 isolates and other infectious viruses during new era of the personalized/precision medicine.

The invention has been described in an illustrative manner, and it is to be understood that the terminology that has been used is intended to be in the nature of words of description rather than of limitation. Obviously, many modifications and variations of the present invention are possible in light of the above teachings. It is, therefore, to be understood that within the scope of the appended claims, the invention can be practiced otherwise than as specifically described.

What is claimed is:

1. A method of inactivating a viral deoxyribonucleic acid (DNA) sequence of a viral genome in a cell, the method comprising:
   (a) cutting the viral DNA sequence at a first target sequence using a CRISPR-Cas targeted to the first target sequence by a first guide ribonucleic acid (gRNA);
   (b) cutting the viral DNA sequence at a second target sequence using a CRISPR-Cas targeted to the second target sequence by a second gRNA, wherein the first target sequence and the second target sequence are different; and
   wherein the method results in inactivating 64% to 96% of the viral DNA sequence in the cell and excising the viral DNA sequence between the first target sequence and the second target sequence from the viral genome in the cell.

* * * * *

SEQUENCE LISTING

```
<160> NUMBER OF SEQ ID NOS: 90

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aaacagggcc agggatcaga tatccactga ccttgt                                    36

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
taaacaaggt cagtggatat ctgatccctg gccct                                     35

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aaacagctcg atgtcagcag ttcttgaagt actcgt                                    36

<210> SEQ ID NO 4
```

```
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
taaacgagta cttcaagaac tgctgacatc gagct                              35

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
caccgattgg cagaactaca cacc                                          24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aaacggtgtg tagttctgcc aatc                                          24

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
caccgcgtgg cctgggcggg actg                                          24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aaaccagtcc cgcccaggcc acgc                                          24

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
caccgatctg tggatctacc acacaca                                       27

<210> SEQ ID NO 10
<211> LENGTH: 27
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aaactgtgtg tggtagatcc acagatc                                       27

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
caccgctgct tatatgcagc atctgag                                       27

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aaacctcaga tgctgcatat aagcagc                                       27

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
caccgtgtgg tagatccaca gatca                                         25

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aaactgatct gtggatctac cacac                                         25

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
caccgcaggg aagtagcctt gtgtg                                         25

<210> SEQ ID NO 16
<211> LENGTH: 25
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 16
aaaccacaca aggctacttc cctgc                                           25

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
caccgatcag atatccactg acctt                                           25

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
aaacaaggtc agtggatatc tgatc                                           25

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
caccgcacac taatacttct ccctc                                           25

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aaacgaggga gaagtattag tgtgc                                           25

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
caccgcctcc tagcatttcg tcaca                                           25

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
aaactgtgac gaaatgctag gaggc                                           25

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
caccgcatgg cccgagagct gcatc                                           25

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
aaacgatgca gctctcgggc catgc                                           25

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
caccgcagca gtctttgtag tactc                                           25

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
aaacgagtac tacaaagact gctgc                                           25

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
caccgctgac atcgagcttt ctaca                                           25

<210> SEQ ID NO 28
<211> LENGTH: 25
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 28
aaactgtaga aagctcgatg tcagc                                             25

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
caccgtctac aagggacttt ccgct                                             25

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
aaacagcgga agtcccttg tagac                                              25

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
caccgctttc cgctggggac tttcc                                             25

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
aaacggaaag tccccagcgg aaagc                                             25

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
caccgcctcc ctggaaagtc cccag                                             25

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 34
aaacctgggg actttccagg gaggc                                    25

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
caccgcctgg gcgggactgg ggag                                     24

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
aaacctcccc agtcccgccc aggc                                     24

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
caccgtccat cccatgcagg ctcac                                    25

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
aaacgtgagc ctgcatggga tggac                                    25

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
caccgcggag agagaagtat tagag                                    25

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
aaacctctaa tacttctctc tccgc                                    25

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
caccggccag atgagagaac caag                                     24

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
aaaccttggt tctctcatct ggcc                                     24

<210> SEQ ID NO 43
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
caccgccttc ccacaaggga aggcca                                   26

<210> SEQ ID NO 44
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
aaactggcct tcccttgtgg gaaggc                                   26

<210> SEQ ID NO 45
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
caccgcgaga gcgtcggtat taagcg                                   26

<210> SEQ ID NO 46
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 46
aaaccgctta ataccgacgc tctcgc                                          26

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
caccggatag atgtaaaaga cacca                                           25

<210> SEQ ID NO 48
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
aaactggtgt cttttacatc tatcc                                           25

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
caccgcagga tatgtaactg acag                                            24

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
aaacctgtca gttacatatc ctgc                                            24

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
caccgcatgg gtaccagcac acaa                                            24

<210> SEQ ID NO 52
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
```
aaacttgtgt gctggtaccc atgc                                          24

<210> SEQ ID NO 53
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
caccgcttta ttgaggctta agcag                                         25

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
aaacgagtca cacaacagac gggc                                          24

<210> SEQ ID NO 55
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
tggaatgcag tggcgcgatc ttggc                                         25

<210> SEQ ID NO 56
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
cacagcatca agaagaacct gat                                           23

<210> SEQ ID NO 57
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
tgaagatctc ttgcagatag cag                                           23

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58

```
gatctgtgga tctaccacac aca                                           23
```

<210> SEQ ID NO 59
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59

```
cccactgtgt ttagcatggt att                                           23
```

<210> SEQ ID NO 60
<211> LENGTH: 101
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, u, g, unknown or other

<400> SEQUENCE: 60

```
nnnnnnnnnn nnnnnnnnnn guuuuagagc uagaaauagc aaguuaaaau aaggcuaguc    60
cguuaucaac uugaaaaaag uggcaccga gucggugcuuu u                      101
```

<210> SEQ ID NO 61
<211> LENGTH: 400
<212> TYPE: DNA
<213> ORGANISM: Human immunodeficiency virus 1

<400> SEQUENCE: 61

```
tccttgatct gtggatctac cacacacaag gctacttccc tgattggcag aactacacac    60
cagggccagg gatcagatat ccactgacct ttggatggtg cttcaagtta gtaccagttg   120
aaccagagca agtagaagag gccaatgaag gagagaacaa cagcttgtta caccctatga   180
gccagcatgg gatggaggac ccggagggag aagtattagt gtggaagttt gacagcctcc   240
tagcatttcg tcacatggcc cgagagctgc atccggagta ctacaaagac tgctgacatc   300
gagctttcta caagggactt tccgctgggg acttccagg gaggtgtggc ctgggcggga   360
ctggggagtg gcgagccctc agatgctaca tataagcagc                        400
```

<210> SEQ ID NO 62
<211> LENGTH: 26
<212> TYPE: DNA
<213> ORGANISM: Human immunodeficiency virus 1

<400> SEQUENCE: 62

```
gagggctcgc cactccccag agctgc                                        26
```

<210> SEQ ID NO 63
<211> LENGTH: 25
<212> TYPE: DNA
<213> ORGANISM: Human immunodeficiency virus 1

<400> SEQUENCE: 63

```
cgctcccctg gtgtgtagtt ctgcc                                         25
```

<210> SEQ ID NO 64
<211> LENGTH: 46

```
<212> TYPE: DNA
<213> ORGANISM: Human immunodeficiency virus 1

<400> SEQUENCE: 64
agggctcgcc actccccagc ctggtgtgta gttctgccaa tcaggg          46

<210> SEQ ID NO 65
<211> LENGTH: 633
<212> TYPE: DNA
<213> ORGANISM: Human immunodeficiency virus 1

<400> SEQUENCE: 65
tggaagggct aatttggtcc caaaaaagac aagagatcct tgatctgtgg atctaccaca    60
cacaaggcta cttccctgat tggcagaact acacaccagg gccagggatc agatatccac   120
tgacctttgg atggtgcttc aagttagtac cagttgaacc agagcaagta gaagaggcca   180 ataaggaga gaagaacagc ttgttacacc ctatgagcca gcatgggatg gaggacccgg   240
agggagaagt attagtgtgg aagtttgaca gcctcctagc atttcgtcac atggcccgag   300
agctgcatcc ggagtactac aaagactgct gacatcgagc tttctacaag gactttccg    360 ctggggactt tccagggagg tgtggcctgg gcgggactgg ggagtggcga gccctcagat   420
gctacatata agcagctgct ttttgcctgt actgggtctc tctggttaga ccagatctga   480
gcctgggagc tctctggcta actagggaac ccactgctta agcctcaata aagcttgcct   540
tgagtgctca aagtagtgtg tgcccgtctg ttgtgtgact ctggtaacta gagatccctc   600 aacccttttta gtcagtgtgg aaaatctcta gca                              633

<210> SEQ ID NO 66
<211> LENGTH: 49
<212> TYPE: DNA
<213> ORGANISM: Human immunodeficiency virus 1

<400> SEQUENCE: 66
gccgagagct gcatccggag ctaagtttta cttcaagaac tgctgacat          49

<210> SEQ ID NO 67
<211> LENGTH: 23
<212> TYPE: DNA
<213> ORGANISM: Human immunodeficiency virus 1

<400> SEQUENCE: 67
atcagatatc cactgacctt tgg                                      23

<210> SEQ ID NO 68
<211> LENGTH: 23
<212> TYPE: DNA
<213> ORGANISM: Human immunodeficiency virus 1

<400> SEQUENCE: 68
cagcagttcg aagtactccc cgg                                      23

<210> SEQ ID NO 69
<211> LENGTH: 15
<212> TYPE: DNA
<213> ORGANISM: Human immunodeficiency virus 1

<400> SEQUENCE: 69
tccactgacc tttgg                                               15

<210> SEQ ID NO 70
```

```
<211> LENGTH: 16
<212> TYPE: DNA
<213> ORGANISM: Human immunodeficiency virus 1

<400> SEQUENCE: 70
atccactgac ctttgg                                                          16

<210> SEQ ID NO 71
<211> LENGTH: 24
<212> TYPE: DNA
<213> ORGANISM: Human immunodeficiency virus 1

<400> SEQUENCE: 71
gcgtttacgt gtgtgccaag tgtg                                                 24

<210> SEQ ID NO 72
<211> LENGTH: 30
<212> TYPE: DNA
<213> ORGANISM: Human immunodeficiency virus 1

<400> SEQUENCE: 72
gctatgagct gttctccagc cgctcgaagt                                           30

<210> SEQ ID NO 73
<211> LENGTH: 78
<212> TYPE: DNA
<213> ORGANISM: Human immunodeficiency virus 1

<400> SEQUENCE: 73
ctggggactt ccagggagg tgtggcctgg gcgggactgg ggggccagat gagagaacca           60
aggggaagtg acatagca                                                        78

<210> SEQ ID NO 74
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
ctggggactt ccagggagg cgtggcctgg gcgggacaag gggaagtgac atagca               56

<210> SEQ ID NO 75
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
ctggggactt ccagggagg cgtggcctgg gcgggacaag ggtaagtgac atagca               56

<210> SEQ ID NO 76
<211> LENGTH: 65
<212> TYPE: DNA
<213> ORGANISM: Human immunodeficiency virus 1

<400> SEQUENCE: 76
acgtggcccg agagctgcat ccggggatag atgtaaaaga caccaaggaa gccttagata         60
agata                                                                     65
```

```
<210> SEQ ID NO 77
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
acgtggcccg agagctgcac caaggaagcc ttagataaga ta                    42

<210> SEQ ID NO 78
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
acatggcccg agagctgccc aaggaagcct tagataagat a                     41

<210> SEQ ID NO 79
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
acgtggccag agagctgcca aggaagcctt agataagata                       40

<210> SEQ ID NO 80
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
acatggcccg agagctgcac caaggaagcc ttagataaga ta                    42

<210> SEQ ID NO 81
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
acgtggcccg agagctgcag gtgtgccacc atgcccagct agttttttgta ttttaccaag    60 gaagccttag aaaagata                                               78

<210> SEQ ID NO 82
<211> LENGTH: 233
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82
acatggcccg agagctgcca ggccggtgat gctctggtgg atcagggtgg cgtccagcac    60
```
ctctttggtg ctggtgtacc tcttccggtc gatggtggtg tcaaagtact tgaaggcggc    120
aggggctccc agattggtca gggtaaacag gtggatgata ttctcggcct gctctctgat    180
gggcttatcc cggtgcttgt tgtaggcgga ccaaggaagc cttagataag ata           233

<210> SEQ ID NO 83
<211> LENGTH: 328
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83
acgtggcccg agagctgcat ccggactgta ctgagtctct ctggttagac cagatctgag    60
cctgggagct ctctggctaa ctagggaacc cactgcttaa gcctcaataa agcttgcctt    120
gagtgcttca agtagtgtgt gcccgtctgt tgtgtgattc tggtaactag agatccctca    180
gaccctttta gtcagtgtgg aaaatctcta gcagggcccg tttaaacccg ctgatcagcc    240
tcgactgtgc cttctagtta ccagccatct gttgtttgcc cctcccccgt gccttccttg    300
accctgcaag gaagccttag ataagata                                       328

<210> SEQ ID NO 84
<211> LENGTH: 86
<212> TYPE: DNA
<213> ORGANISM: Human immunodeficiency virus 1

<400> SEQUENCE: 84
agctgcatcc ggagtactac aaagactgct gacatcgagc tttctggata gatgtaaaag    60
acaccaagga agccttagat aagata                                         86

<210> SEQ ID NO 85
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
agctgcatcc ggagtactac aaagactgct gacatcgagc tttctaccaa ggaagcctta    60
gataagata                                                            69

<210> SEQ ID NO 86
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
agctgcatcc ggagtactac aaagactgct gacatcgagc tttaccaagg aagccttaga    60
taagata                                                              67

<210> SEQ ID NO 87
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 87
agctgcatcc ggagtactac aaagactgct gacatcgagc tttctcacca aggaagcctt      60
agataagata                                                            70

<210> SEQ ID NO 88
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
agctgcatcc ggagtactac aaagactgct gacatcgagc tttctccaag gaagccttag      60
ataagata                                                              68

<210> SEQ ID NO 89
<211> LENGTH: 398
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89
agctgcatcc ggagctgtac tgggtctctc tggttagacc agatctgagc ctgggagctc      60
tctggctaac tagggaaccc actgcttaag cctcaataaa gcttgccttg agtgcttcaa     120
gtagtgtgtg cccgtctgtt gtgtgactct ggtaactaga gatccctcag acccttttag     180
tcagtgtgga aaatctctag cagagcccgt ttaaacccgc tgatcagcct cgactgtgcc     240
ttctagttgc cagccatctg ttgtttgccc ctcccccgtg ccttccttga ccctggaagg     300
tgccactccc actgtccttt cctaataaaa tgaggaaatt gcatcgcatt gtctgagtag     360
gtgtcattct attcaccaag gaagccttag ataagata                             398

<210> SEQ ID NO 90
<211> LENGTH: 225
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90
agctgcatcc ggagcactac aaagactgct gacatcgagc ttcactacaa agactgctga      60
catcgagctt taattcactc ccaaagaagt caagatctgc tttttgcctg tactgggtct     120
ctctggttag accagagtct ctctggttag accagatctg agcctgggag ctctctggct     180
aactagggaa cccactgctt aaccaaggaa gccttagata agata                     225
```